United States Patent
McGarrity et al.

(10) Patent No.: US 7,871,795 B2
(45) Date of Patent: *Jan. 18, 2011

(54) **TARGETED *TRANS*-SPLICING OF HIGHLY ABUNDANT TRANSCRIPTS FOR IN VIVO PRODUCTION OF RECOMBINANT PROTEINS**

(75) Inventors: Gerard J. McGarrity, Gaithersburgh, MD (US); Mariano A. Garcia-Blanco, Durham, NC (US)

(73) Assignee: VIRxSYS Corporation, Gaithersburg, MD (US)

( * ) Notice: Subject to any disclaimer, the term of this patent is extended or adjusted under 35 U.S.C. 154(b) by 457 days.

This patent is subject to a terminal disclaimer.

(21) Appl. No.: 11/245,907

(22) Filed: Oct. 7, 2005

(65) Prior Publication Data

US 2006/0172381 A1    Aug. 3, 2006

Related U.S. Application Data

(63) Continuation of application No. 11/141,447, filed on May 31, 2005, which is a continuation-in-part of application No. 11/041,155, filed on Jan. 21, 2005.

(60) Provisional application No. 60/617,324, filed on Oct. 8, 2004.

(51) Int. Cl.
C12P 21/06 (2006.01)
C07H 21/04 (2006.01)
C12N 9/00 (2006.01)

(52) U.S. Cl. .................. 435/69.1; 435/183; 435/320.1; 435/325; 536/23.2; 530/350

(58) Field of Classification Search ...................... 435/6, 435/91.1, 320.1, 325, 455, 183; 536/23.1, 536/23.2; 530/350
See application file for complete search history.

(56) References Cited

U.S. PATENT DOCUMENTS

| | | | |
|---|---|---|---|
| 4,980,286 A | 12/1990 | Morgan et al. | |
| 5,354,678 A | 10/1994 | Lebkowski et al. | |
| 5,585,362 A | 12/1996 | Wilson et al. | |
| 5,589,377 A | 12/1996 | Lebkowski et al. | |
| 5,616,326 A | 4/1997 | Spibey | |
| 5,670,488 A | 9/1997 | Gregory et al. | |
| 5,700,470 A | 12/1997 | Saito et al. | |
| 5,731,172 A | 3/1998 | Saito et al. | |
| 5,747,072 A | 5/1998 | Davidson et al. | |
| 5,756,283 A | 5/1998 | Wilson et al. | |
| 5,789,390 A | 8/1998 | Descamps et al. | |
| 5,820,868 A | 10/1998 | Mittal et al. | |
| 5,837,484 A | 11/1998 | Trempe et al. | |
| 5,843,742 A | 12/1998 | Natsoulis et al. | |
| 5,851,806 A | 12/1998 | Kovesdi et al. | |
| 5,858,351 A | 1/1999 | Podsakoff et al. | |
| 5,869,037 A | 2/1999 | Crystal et al. | |
| 5,871,982 A | 2/1999 | Wilson et al. | |
| 5,877,011 A | 3/1999 | Armentano et al. | |
| 5,885,808 A | 3/1999 | Spooner et al. | |
| 5,891,690 A | 4/1999 | Massie | |
| 5,919,676 A | 7/1999 | Graham et al. | |
| 5,922,576 A | 7/1999 | He et al. | |
| 5,928,944 A | 7/1999 | Seth et al. | |
| 5,932,210 A | 8/1999 | Gregory et al. | |
| 5,952,221 A | 9/1999 | Kurtzman et al. | |
| 5,962,311 A | 10/1999 | Wickham et al. | |
| 5,962,313 A | 10/1999 | Podsakoff et al. | |
| 5,998,205 A | 12/1999 | Hallenbeck et al. | |
| 6,013,487 A | 1/2000 | Mitchell | |
| 6,083,702 A | 7/2000 | Mitchell et al. | |
| 6,280,978 B1 | 8/2001 | Mitchell et al. | |
| 7,094,399 B2 | 8/2006 | Otto | |
| 7,399,753 B2 | 7/2008 | Mitchell | |
| 2006/0094110 A1 | 5/2006 | McGarrity | |
| 2006/0134658 A1 | 6/2006 | Garcia-Blanco | |
| 2006/0154257 A1 | 7/2006 | Mitchell | |
| 2006/0160182 A1 | 7/2006 | McGarrity | |
| 2006/0177933 A1 | 8/2006 | Puttaraju | |
| 2006/0194317 A1 | 8/2006 | Puttaraju | |
| 2006/0234247 A1 | 10/2006 | Puttaraju | |
| 2006/0246422 A1 | 11/2006 | Mitchell | |

FOREIGN PATENT DOCUMENTS

| | | |
|---|---|---|
| WO | WO 88/09810 | 12/1988 |
| WO | WO 89/10134 | 11/1989 |
| WO | WO 98/11241 | 3/1998 |
| WO | WO 00/09734 | 2/2000 |

OTHER PUBLICATIONS

U.S. Appl. No. 10/693,192, filed Oct. 23, 2003, "Screening Method for Identification of Efficient Pre-Trans-Splicing Molecules," Mitchell et al.

U.S. Appl. No. 10/434,727, filed May 8, 2003, "Use of Sliceosome Mediated RNA Trans-Splicing to Confer Cell Selective Replication to Adenoviruses," Otto et al.

(Continued)

*Primary Examiner*—Chih-Min Kam
(74) *Attorney, Agent, or Firm*—Konstantina M. Katcheves; Saul Ewing; VIRxSYS Corporation

(57) ABSTRACT

The present invention provides methods and compositions for generating novel nucleic acid molecules through RNA trans-splicing that target a highly expressed pre-mRNA and contain the coding sequence of a protein or polypeptide of interest. The compositions of the invention include pre-trans-splicing molecules (PTMs) designed to interact with the target precursor messenger RNA molecule (target pre-mRNA) that is abundantly expressed, and mediate a trans-splicing reaction resulting in the generation of novel chimeric RNA molecule (chimeric RNA) capable of encoding a protein or polypeptide of interest. The invention provides for the in vivo production of chimeric RNA molecules that encode and result in the production of a protein or polypeptide of interest.

10 Claims, 64 Drawing Sheets

OTHER PUBLICATIONS

U.S. Appl. No. 10/374,784, filed Feb. 25, 2003, "Trans-Splicing Mediated Imaging of Gene Expression," Mitchell et al.
U.S. Appl. No. 10/360,787, filed Jun. 5, 2002, "Spliceosome Mediated RNA Trans-Splicing for Correction of Factor VIII Genetic Defects," Mitchell et al.
U.S. Appl. No. 10/198,447, filed Jul. 17, 2002, "Spliceosome Mediated RNA Trans-Splicing for Correction of Skin Disorders," Mitchell et al.
U.S. Appl. No. 10/136,723, filed Apr. 30, 2002, "Transgenic Animal Model for Spliceosome-mediated RNA Trans-Splicing," Puttaraju et al.
U.S. Appl. No. 10/103,294, filed Mar. 20, 2002, "Spliceosome Mediated RNA Trans-Splicing," Mitchell et al.
U.S. Appl. No. 10/075,028, filed Feb. 12, 2002, "Methods and Compositions for Use in Spliceosome Mediated RNA Trans-Splicing," Mitchell et al.
U.S. Appl. No. 10/076,248, filed Feb. 12, 2002, "Methods and Compositions for Use in Spliceosome Mediated RNA Trans-Splicing," Mitchell et al.
U.S. Appl. No. 09/838,858, filed Apr. 20, 2001, "Methods and Compositions for Use in Spliceosome Mediated RNA Trans-Splicing," Mansfield et al.
U.S. Appl. No. 09/756,097, filed Jan. 8, 2001, "Methods and Compositions for Use in Spliceosome Mediated RNA Trans-Splicing," Mitchell et al.
U.S. Appl. No. 09/756,095, filed Jan. 8, 2001, "Methods and Compositions for Use in Spliceosome Mediated RNA Trans-Splicing," Mitchell et al.
U.S. Appl. No. 09/756,096, filed Jan. 8, 2001, "Methods and Compositions for Use in Spliceosome Mediated RNA Trans-Splicing," Mitchell et al.
Bhaumik et al., "Molecular Imaging of Gene Expression in Living Subjects by Splicesome-Mediated RNA Trans-Splicing," Jun. 8, 2004, Proc. Natl. Acad. Sci., 101:23:8693-8698.
Tahara et al., "Trans-Splicing Repair of CD40-Ligand Deficiency Results in Naturally Regulated Correction of A Mouse Model of Hyper-IgM X-Linked Immunodeficiency," Aug. 2004, Nature Medicine, 10:835-841.
Chao et al., "Phenotype Correction of Hemophilia A Mice by Spliceosome-Mediated RNA Trans-Splicing," Aug. 2003, Nature Medicine, 9:1-5.
Liu et al., "Partial Correction of Endogenous Δ508 CFTR in Human Cystic Fibrosis Airway Epithelia by Spliceosome-Mediated RNA Trans-Splicing," Jan. 2002, Nature Biotechnology, 20:47-52.
Kim et al., "Role of the Nonsense-Mediated Decay Factor hUpf3 in the Splicing Dependent Exon-Exon Junction Complex," Sep. 7, 2001, Science 293:1832-1836.
Kirn et al., "Replication-Selective Virotherapy for Cancer:Biological Principles, Risk Management and Future Directions," Jul. 2001, Nat. Med. 7:781-787.
Tian et al., "Strong RNA Splicing Enhancers Identified by a Modified Method of Cycled Selection Interact with SR Protein," Sep. 7, 2001, J. Biological Chemistry 276:33833-33839.
Mansfield et al., "Repair of CFTR mRNA by Splicesome-Mediated RNA Trans-Splicing," Jul. 28, 2000, Gene Therapy 7:1885-1895.
Tacke et al., "Determinants of SR Protein Specificity," 1999, Curr. Opin. Cell Biol. 11:358-362.
He et al. "A Simplified System for Generating Recombinant Adenoviruses," Mar. 1998, Proc. Natl. Acad. Sci., 95, 2509-2514.
Lan et al., "Ribozyme-Mediated Repair of Sickle β-Globin mRNAs in Erythrocyte Precursors" Jun. 5, 1998, Science 280:1593-1596.
Phylactou et al., "Ribozyme-Mediated Trans-Splicing of a Trinucleotide Repeat" Apr. 1998, Nature Genetics 18:378-381.
Staley et al., "Mechanical Devices of the Spliceosome: Motors, Clocks, Springs and Things," 1998, Cell 92:315-326.
Bellet et al., "Malignant Transformation of Nontrophoblastic Cells is Associated With the Expression of Chorionic Gonadotropin β Genes Normally Transcribed Introphoblastic Cells," Feb. 1, 1997, Cancer Res. 57:516-523.
Coolidge et al., "Functional Analysis of The Polypyrimidine Tract in Pre-mRNA Splicing," 1997, Nucleic Acids Res. 25:888-896.

Crouzet et al. "Recombinational Construction in *Escherichia coli* of Infectious Adenoviral Genomes," Feb. 1997, Proc. Natl. Acad. Sci., 94, 1414-1419.
Good et al., "Expression of Small, Therapeutic RNAs in Human Cell Nuclei," 1997, Gene Ther. 4:45-54.
Malek et al., "Evolution of Trans-Splicing Plant Mitochondrial Introns in Pre-Permian Times," Jan. 1997, Proc. Nat'l. Acad. Sci., 94:553-558.
Chartier, et al., "Efficient Generation of Recombinant Adenovirus Vectors by Homologous Recombination in *Escherichia coli*," Jul. 1996, Virol. 70, 4805-4810.
Hoon et al., "Detection of Metastatic Breast Cancer by β-hCG Polymerase Chain Reaction," 1996, Int J. Cancer 69:369-374.
Jones et al., "Tagging Ribozyme Reaction Sites to Follow Trans-Splicing in Mammalian Cells," Jun. 1996, Nature Medicine 2:643-648.
Krämer A., "The Structure and Function of Proteins Involved in Mammalian Pre-mRNA Splicing," 1996, Annu. Rev. Biochem. 65:367-409.
Miyake et al. "Efficient Generation of Recombinant Adenoviruses Using Adenovirus DNA-Terminal Protein Complex and A Cosmid Bearing the Full-Length Virus Genome," Feb. 1996, Proc. Natl. Acad. Sci., 93, 1320-1324.
Nilsson et al., "Multiple Affinity Domains for the Detection, Purification, and Immobilization of Recombinant Proteins," 1996, J. Mol. Recognition, 9:585-594.
Pasman et al., "The 5' and 3' Splice Sites Come Together Via a Three Dimensional Diffusion Mechanism," 1996, Nucleic Acids Res. 24(9):1638-1645.
Boelens et al., "Nuclear Retention of RNA as a Mechanism for Localization" 1995, RNA 1:273-283.
Bruzik et al., "Enhancer-Dependent Interaction Between 5' and 3' Splice Sites in Trans," 1995, Proc. Nat'l. Acad. Sci., 92:7056-7059.
Chiara et al., "A Two-Step Mechanism for 5' and 3' Splice-Site Pairing," Jun. 1995, Nature 375:510-513.
Davis et al., "RNA Trans-Splicing in Flatworms," Sep. 15, 1995, J. Biol. Chem. 270:21813-21819.
Eul et al., "Experimental Evidence for RNA Trans-Splicing in Mammalian Cells," 1995, EMBO. J. 14(13):3226-3235.
Xiang-Dong Fu, "The Superfamily of Arginine/Serine-Rich Splicing Factors," 1995, RNA 1:663-680.
Bett et al. "An Efficient and Flexible System for Construction of Adenovirus Vectors with Insertions or Deletions in Early Regions 1 and 3," Sep. 1994, Proc. Natl. Acad. Sci., 91,8802-8806.
Hollenberg et al., "Multiple Promoter Elements in the Human Chorionic Gonadotropin B Subunit Genes Distinguish their Expression from Luteinizing Hormone β Gene," 1994, Mol. Cell Endo., 106:111-119.
Ketner et al. "Efficient Manipulation of the Human Adenovirus Genome as an Infectious Yeast Artificial Chromosome Clone," Jun. 1994, Proc. Natl. Acad. Sci., 91, 6186-6190.
Sullenger et al., "Ribozyme-Mediated Repair of Defective mRNA by Targeted Trans-Splicing," Oct. 1994, Nature 371:619-622.
Goldspiel et al., "Human Gene Therapy," Jul. 1993, Clinical Pharmacy 12:488-505.
Kozarsky and Wilson et al., "Gene Therapy: Adenovirus Vectors," 1993, Current Opinion in Genetics and Development 3:499-503.
Miller and Rosman, "Use of Retroviral Vectors for Gene Transfer and Expression," 1993, Meth. Enzymol. 217:581-599.
Moore and Sharp, "Evidence for Two Active Sites in The Splicesome Provided by Stereochemistry of Pre-mRNA Splicing," Sep. 23, 1993, The Nature, 365:364-368.
Moore et al, "Splicing of Precursors to mRNA by The Spliceosome," 1993, RNA World, 303-357.
Morgan and Anderson, "Human Gene Therapy," 1993, Ann. Rev. Biochem. 62:191-217.
Mulligan, Richard C., "The Basic Science of Gene Therapy," May 14, 1993, Science 260:926-932.
Roscigno et al., "A Mutational Analysis of the Polypyrimidine Tract of Introns," May 25, 1993, J. Bio. Chem., 268:11222-11229.
Tolstoshev, Paul, "Gene Therapy, Concepts, Current Trials, and Future Directions," 1993, Ann. Rev. Pharmacol. Toxicol. 33:573-596.

Acevedo et al., "Human Chorionic Gonadotropin-Beta Subunit Gene Expression in Cultured Human Fetal and Cancer Cells of Different Types and Origins," Oct. 15, 1995, Cancer 76:1467-1475.

Bruzik et al., "Spliced Leader RNAs from Lower Eukaryotes are Trans-spliced in Mammalian Cells," Dec. 1992, Nature 360:692-695.

Vellard et al., "A Potential Splicing Factor is Encoded by the Opposite Strand of The Trans-Spliced C-myb Exon," 1992, Proc. Nat'l. Acad. Sci., 89:2511-2515.

Dingwall and Laskey, "Nuclear Targeting Sequences—A Consensus?" Dec. 1991, Trends in Biochem. Sci., 16:478-481.

Ghattas et al., "The Encephalomyocarditis Virus Internal Ribosome Entry Site Allows Efficient Coexpression of Two Genes from a Recombinant Provirus in Culture Cells and in Embryos," Dec. 1991, Mol. Cell Biol. 11:5848-5859.

Janknecht et al., "Rapid and Efficient Purification of Native Histidine-Tagged Protein Expressed by Recombinant Vaccinia Virus," Jul. 8, 1991, Proc. Natl. Acad. Sci., 88:8972-8976.

Rosenfeld et al. "Adenovirus-Mediated Transfer of a Recombinant $\alpha_1$ Antitrypsin Gene to the Lung Epithelium in Vivo," Apr. 19, 1991, Science, 252, 431-4.

Wu and Wu, "Delivery Systems for Gene Therapy," 1991, Biotherapy 3:87-95.

Gilardi et al. "Expression of Human $\alpha_1$-Anti-trypsin Using a Recombinant Adenovirus Vector," 1990, EBS Lett. 267, 60-62.

Rajkovic et al., "A Spliced Leader is Present on a Subset of mRNAs from the Human Parasite Schistosoma Mansoni" Nov. 1990, Proc. Nat'l. Acad. Sci., 87:8879-8883.

Schneider and Banes, "Building Blocks for Oligonucleotide Analogs with Dimethylene-Sulfide-Sulfoxide and Sulfone Groups Replacing Phosphodiester Linkages," 1990, Tet. Letters, 31:335-338.

Senapathy et al., "Splice Junctions, Branch Point Sites, and Exons-:Sequence Statistics, Identification, and Applications to Genome Project," 1990, Methods in Enzymology, 183:252-278.

Uhlmann and Peyman, "Antisense Oligonucleotides: A New Therapeutic Principle," Jun. 1990, Chemical Reviews, 90:543-584.

Kerem et al., "Identification of the Cystic Fibrosis Gene: Genetic Analysis," Sep. 8, 1989, Science, 245:1073-1080.

Letsinger et al., "Cholesteryl-Conjugated Oligonucleotide: Synthesis, Properties, and Activity as Inhibitors of Replication of Human Immunodeficiency Virus in Cell Culture," Sep. 1989, Proc. Natl. Acad. Sci., 86:6553-6556.

Reed, Robin, "The Organization of 3' Splice Sites Sequences in Mammalian Introns," 1989, Genes Dev. 3:2113-2123.

Riordan et al., "Identification of the Cystic Fibrosis Gene: Cloning and Characterization of Complementary DNA," 1989, Science, 245:1066-1073.

Rommens et al., "Identification of the Cystic Fibrosis Gene: Chromosome Walking and Jumping," Sep. 8, 1989, Science, 245:1059-1065.

Shimizu et al., "Immunoglobulin Double-Isotype Expression by Trans-mRNA In a Human Immunoglobulin Transgenic Mouse," Oct. 1989, Proc. Nat'l. Acad. Sci. 86:8020-8023.

Smith et al., "Scanning From an Independently Specified Branch Point Defines the 3' Splice Site of Mammalian Introns," 1989, Nature, 342:243-247.

Van der Krol et al., "Modulation of Eukaryotic Gene Expression by Complementary RNA or DNA Sequences," 1988, BioTechniques, 6:958-976.

Reed & Maniatis, "The Role of The Mammalian Branchpoint Sequence In the Pre-mRNA Splicing," 1988, Genes Dev. 2:1268.

Smith et al, "Single-Step Purification of Polypeptides Expressed in *Escherichia coli* as Fusions with Glutathione S-Transferase," 1988, Gene, 67:31.

Zon et al., "Oligonucleotide Analogues as Potential Chemotherapeutic Agents," 1988, Pharm. Res., 5:539-549.

Krause M et al., "A Trans-Spliced Leader Sequence on Actin mRNA in C. Elegans," 1987, Cell 49:753-761.

Lemaitre et al., "Specific Antiviral Activity of a Poly(L-lysine)-Conjugated Oligodeoxyribonucleotide Sequence Complementary to Vesicular Stomatitis Virus N Protein mRNA Initiation Site," 1987, Proc. Natl. Acad. Sci., 84:648-652.

Wu and Wu, "Receptor-Mediated in Vitro Gene Transformation by a Soluble DNA Carrier System," 1987, J. Biol. Chem., 262:429-4432.

Dingwall and Laskey, "Protein Import into the Cell Nucleus," 1986, Ann. Rev. Cell Biol. 2:367-390.

Murphy et al., "Identification of a Novel Y Branch Structure as an Intermediate in Trypanosome mRNA Processing: Evidence for Trans Splicing," 1986, Cell, 47:517.

Smith et al., "$M_r$ 26,000 Antigen of Schistosoma Japonicum Recognized by Resistant WEH1 129/J Mice is a Parasite Glutathione S-Transferase," 1986, Proc. Natl. Acad. Sci., 83:8703-8707.

Sutton et al., "Evidence for Trans Splicing in Trypanosomes," 1986, Cell 47:527-535.

Konarska et al., "Trans Splicing of mRNA Precursors In Vitro" 1985, Cell 46:165-171.

Solnick et al, "Trans Splicing of mRNA Precursors," 1985, Cell 42:157-164.

Talmadge et al., "Only Three of the Seven Human Chorionic Gonadotropin Beta Subunit Genes can be Expressed in the Placenta," 1984, Nucleic Acids Res. 12:8415.

Accession No. K01722, Corynebacteriophage beta diptheria toxin (DT) gene, Apr. 27, 1993.

Berkner, et al. "Generation of Adenovirus by Transfection of Plasmids," 1983, Nucleic Acids Res. 11, 6003-6020.

Greenfield, "Nucleotide Sequence of the Structural Gene for the Diptheria Toxin Carried by Corynebacteriophage β," 1983, Proc. Natl. Acad. Sci., 80:6853-6857.

Brinster et al., "Regulation of Metallothionein-Thymidine Kinase Fusion Plasmids Injected into Mouse Eggs," 1982, Nature 296:39-42.

Benoist et al., "In Vivo Sequence Requirements of the SV40 Early Promoter Region," 1981, Nature, 290:304-310.

Wagner et al., "Nucleotide Sequence of the Thymidine Kinase Gene of Herpes Simplex Virus Type 1," Mar. 1981, Proc. Natl. Acad. Sci., 78(3):1441-1445.

Yamamoto et al., "Identification of a Functional Promoter in the Long Terminal Repeat of Rous Sarcoma Virus," 1980, Cell, 22:787-797.

Mansfield, et al., Repair of CFTR mRNA by Spliceosome-Mediated RNA Trans-Splicing, Gene Therapy, 2000, vol. 7, 1885-1895.

Manzano, et al., "Failure to Generate Atheroprotective Apolipoprotein Al Phenotypes Using Synthetic RNA/DNA Oligonucleotides (chimeraplasts)", J. Gene Med., 2003, vol. 5, 795-802.

Parolini, et al., "Targeted Replacement of Mouse Apolipoprotein A-I with Human ApoA-I or the Mutant ApoA-I", J. Bio. Chem., 2003, vol. 278, 4740-4746.

Martinez-Sales, E., Internal Ribosome Entry Site Biology and Its Use In Expression Vectors, 1999, Current Opinion in Biology, 10:458-464.

Kikumori et al., "Promiscuity of Pre-mRNA Spliceosome-Meidated Trans Splicing: A Problem for Gene Therapy?," Jul. 20, 2001, Human Gene Therapy, 12:1429-1441.

U.S. Appl. No. 09/941,492 filed Aug. 29, 2001, "Methods and Compositions for Use in Spliceosome Mediated RNA Trans-Splicing," Mitchell et al.

U.S. Appl. No. 08/786,531 filed Jan. 21, 1997, "Vehicles For Stable Transfer of Green Fluorescent Protein Gene And Methods of Use For Same," Link. Jr., et al.

Berget et al., Spliced Segments at the 5' Terminus of Adenovirus 2 Late mRNA, 1977, Proc. Natl. Acad. Sci., 74(8):3171-3175.

Chow et al., "An Amazing Sequence Arrangement at the 5' Ends of Adenovirus 2 Messenger RNA," 1977, Cell 12:1-8.

Graham et al., "Characteristics of a Human Cell Line Transformed by DNA from Human Adenovirus Type 5," 1977, J. Gen. Virol. 36:59-72.

Uchida et al, "Diptheria Toxin and Related Proteins: Isolation and Properties of Mutant Proteins Related to Diptheria Toxin," 1973 J. Biol. Chem., 248:3838.

Puttaraju et al., Spliceosome-Mediated RNA Trans-Splicing as a Tool for Gene Therapy, Nat. Biotech., 1999, vol. 17, 246-252.

Voss et al., "Efficiency Assessment of the Gene Trap Approach", 1998, Development Dynamics, 212:171-180.

Puttaraju et al., "Messenger RNA Repair and Restoration of Protein Function by Spliceosome-Mediated mRNA Trans-Splicing", Mol. Therapy, 2001, vol. 4, 105-114.

Song et al., "Intramuscular Administration of Recombinant Adeno-Associated Virus 2 α-1 Antitrypsin (rAAV-SERPINA1) Vectors in a Nonhuman Primate Model: Safety and Immunologic Aspects", Sep. 3, 2002, Molecular Therapy 6:329-335.

Garcia-Blanco et al, "Spliceosome-Mediated RNA trans-Splicing in Gene Therapy and Genomics," Apr. 20, 2000, Gene Therapy and Regulation, 1:141-163.

Garcia-Blanco et al "Mending the Message", Nat. Biotech., 2003, vol. 21, No. 12, 1448-1449.

Liu et al., "Spliceosome-Mediated RNA trans-Splicing with Recombinant Adeno-Associated Virus Partially Restores Cystic Fibrosis Transmembrane Conductance Regulator Function to Polarized Human Cystic Fibrosis Airway Epithelial Cells," Sep. 2005 *Human Gene Therapy* 16:1116-1123.

Mansfield, et al. "5' Exon Replacement and Repair by Spliceosome-Mediated RNA trans-Splicing", RNA, 2003, vol. 9, 1290-1297.

*Anderson and Anderson, Molec. Cell. Proteomics 2002 1: 845*

Mouse albumin signal pre peptide

ATG AAG TGG GTA ACC TTT CGC CGA CTC CTC TTC GTC TCC GGC TCT GCT TTT

Pro-peptide → HPV-16 anti-E7 scFv (minus the first 7 nts)

TCC AGG GGT GTG TTT CGC CGA GAA GCA CAG GTC CAG CTG GAG TCA GGG
GCT GAG CTT GTG AAG CCT GGG GCT TCA GTG AAG CTG TCC TGC AAG GCT TCT
GGC TAC ACC TTC ACC AGC ATC TAC ATG CAC TGG GTG AAA CAG AGG CCT GGA
CAT GGC CTT GAG AAG TGG ATT GGA GAG ATT TTA CCT GGA AGT GGT AGT ACT ACT AAC   Heavy
TAC AAT GAG AAG TTC AAG CAA CTC ACT GCC AAG GCA TTC ACT GCA GAT ACA TCC TCC   chain
AAC ACA GCC TAC ATG CAA CTC AGC AGC CTG ACA TCT GAG GAC TCT GCC GTC
TAT TAC TGT GCA AGA AGG ACG TAC GGC TAC TGG TTT GCT TAC TGG GGC CAA
GGG ACC ACG GTC ACC GTC TCC TCA GGT GGA GGC GGT TCA GGC GGA GGT GGC   Linker
TCT GGC GGT GGC TCG GAG GGA TCG GAG ACC ATC GTC ACC TAC AGT CAG ATC ATG
GCT GCA TCT CCA AGC AAC TTG GCC ATT TCC CAG CAG GAA ACC TCC CCC   Light
ATA AGT TCC AGC ATT TAT GGC ACA TCC AAC CTG GCT TCT CTC GGA GTC CCT CGC   chain
AAA CCC TGG ATT TAT GGA TCT ACA AGC CTG GCT TCT CTC GGA GTC CCT CGC
TTC AGT GGC AGT GAT TCT GGG ACC TAT TAC TGT CAA CAG TGG AGT AGT TAC CCA
GAG GCT GAA GAT GCT GCT GGG ACC AAG CTG GAA ATA AAA CGG GAC TAC AAA GAC
CTC ACG TTC GGT GCT GGG ACC AAG CTG GAA ATA AAA CGG GAC TAC AAA GAC
GAT GAC GAC AAG TGA
           stop
           codon FLAG tag

SEQ ID NO. 31

Figure 10

Figure 21 SDS gel showing the production of human Apo A-I protein in 293 cells.

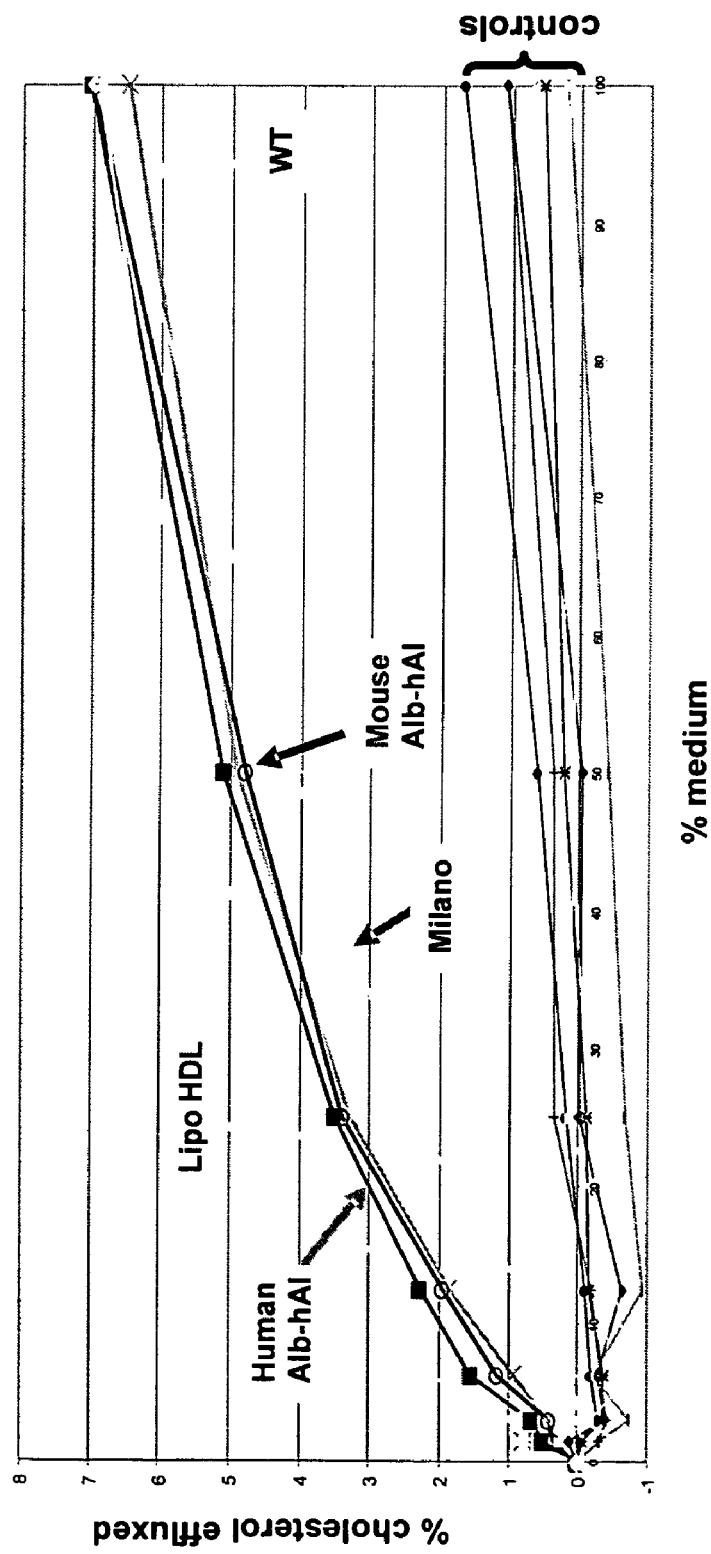
Figure 23 Cholesterol efflux from HeLa control and ABC1 cells with conditioned media from albumin-hApoAI expressing 293 cells.

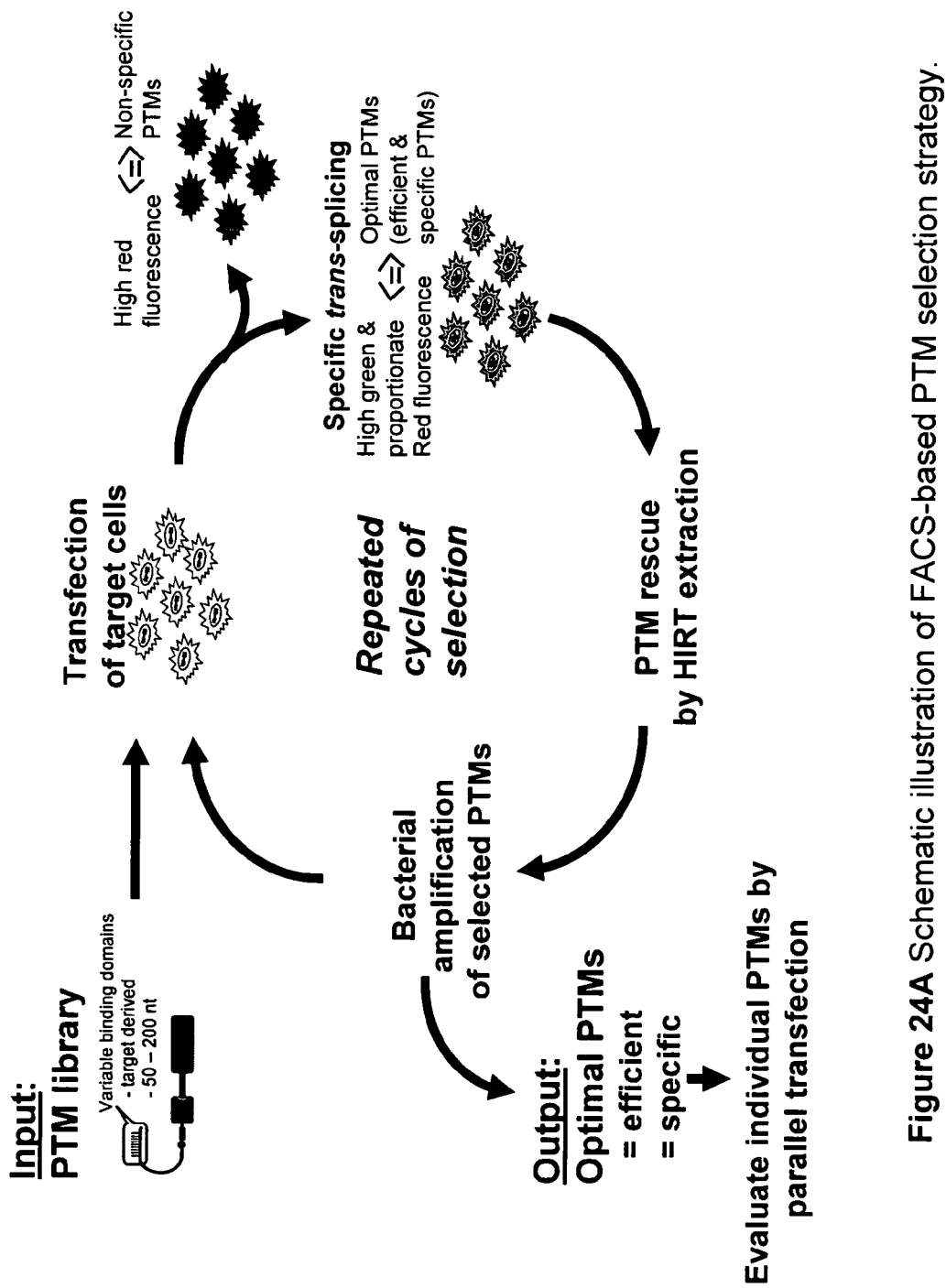
Figure 24A Schematic illustration of FACS-based PTM selection strategy.

Previous Protocol:

1. Library in pQC vector backbone (w/ Maz)
2. Cells collected as single fraction (mean $10^1$-$10^4$)
3. After first round, routinely tested 20-40 clones by parallel transfection
4. Selected the winner from these clones

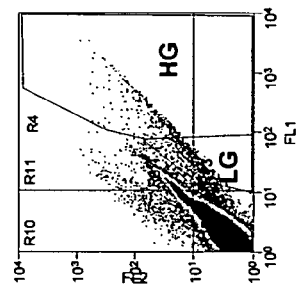

Current (modified) Protocol:

1. Library in pc3.1B vector backbone (pc3.1 with Maz to reduce cryptic cis-splicing to amp gene, and, is a high copy number plasmid).
2. Cells collected as two fractions, LG (mean $10^1$-$10^2$) and HG (mean $10^2$-$10^4$)
3. After first round, pre-tested 40 clones from each fraction and found that the HG fraction had higher (& brighter) GFP positive cells than LG fraction (2:1)
4. Tested ~100 PTMs from HG fraction by parallel transfection
5. Selected 20 PTMs for further analysis.
6. Also, tested the effect of target conc. to "better" discriminate the winner from the pool. Based on the results, reducing the target conc. that is comparable to stables produced better results.
7. The lead candidate BDs were selected from 140 clones.

Figure 24B Comparison between previously described HCS vs. the current HCS steps.

5'GFP-AlbIn1Ex2 Pre-mRNA Target Sequence

SEQ ID NO. 39

ATGGCTCAGTCAAAGCACGGTCTAACAAAAGAAATGACAATGAAATACCGTATGGAAGGGTGCGTCGATG
GACATAAATTTGTGATCACGGGAGAGGGGCATTGGATATCCGTTCAAAGGGAAACAGGCTATTAATCTGTG
TGTGGTCGAAGGTGGACCATTGCCATTTGCCGAAGACATATTGTCAGCTGCCTTTATGTACGGAAACAG/

5' splice junction

SEQ ID NO. 40

GTAAGAAATCCATTTTCTATTGTTCAACTTTTATTCTATTTCCCAGTAAAATAAAGTTTTAGTAAACT
CTGCATCTTTAAAGAATTATTTGGCATTTATTTCTAAATGGCATAGTATTTGTATTTGTGAAGTCTT
ACAAGGTTATCTTATTAATAAAATTCAAACATCCTAGGTAAAAAAAAAGGTCAGAATTGTTTAGTG
ACTGTAATTTTCTTTTGCGCACTAAGGAAAGTGCAAAGTAACTTAGAGTGACTGAAACTTCACAGAATAG
GGTTGAAGATTGAATTCATAACTATCCCAAAGACCTATCCATTGCACTATGCTTTATTTAAAAACCACAA
AACCTGTCGTGTTGATAGACACTAAAAGAGTATTAGATATTATCTAAGTTTGAATATAAGGCTATAACATATTAA
TTGCTGTTGATAGACACTAAAAGAGTATTAGATATTATCTAAGTTTGAATATAAGGCTATAATATTTAA
TAATTTTAAAATAGTATTCTTGGTAATTATTCTTCTGTTTAAAGGCAGAAGAAATAATTGAACA
TCATCCTGAGTTTTTCTGTAGGAATCAGAGCCCAATATTTGAAACAAATGCATAATCTAAGTCAAATGG
AAAGAAATATAAAAGTAACATTATTACTTCTTGTTTTCTTCAGTATTTAACAATCCTTTTTTTCTTCC

3' splice junction

SEQ ID NO. 41

CTTGCCCAG/ACAAGAGTGAGGTTGCTCATCGGTTTAAAGATTGGGAGAAGAAATTTCAAAGCCTT

Figure 25

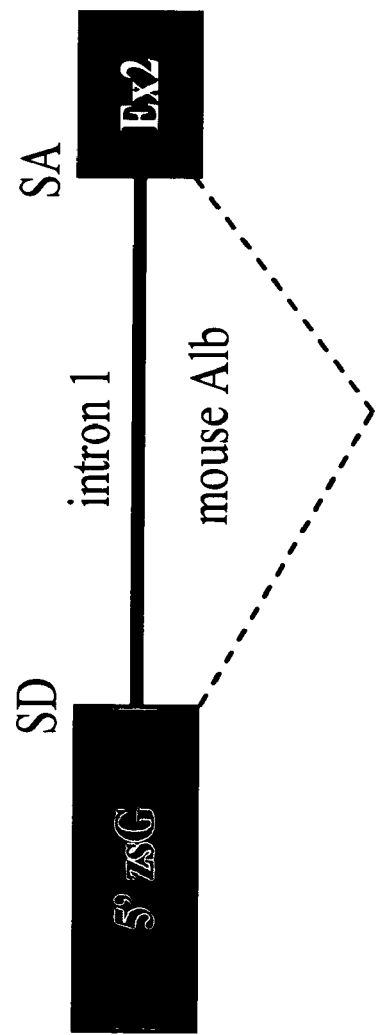
Figure 26 Schematic diagram of the pre-mRNA target used in the HCS. Abbreviations: SD, splice donor site; SA, splice acceptor site. Dotted lines indicate target cis-splicing.

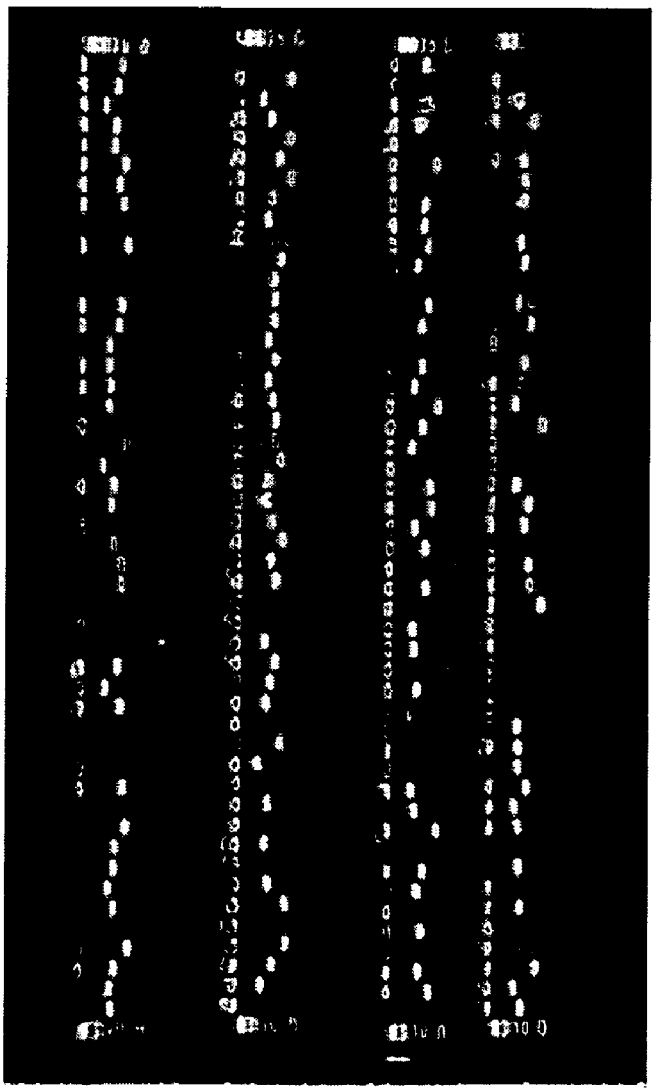
Figure 28 PCR screen showing the cloning efficiency and diversity of the mouse albumin BD library.

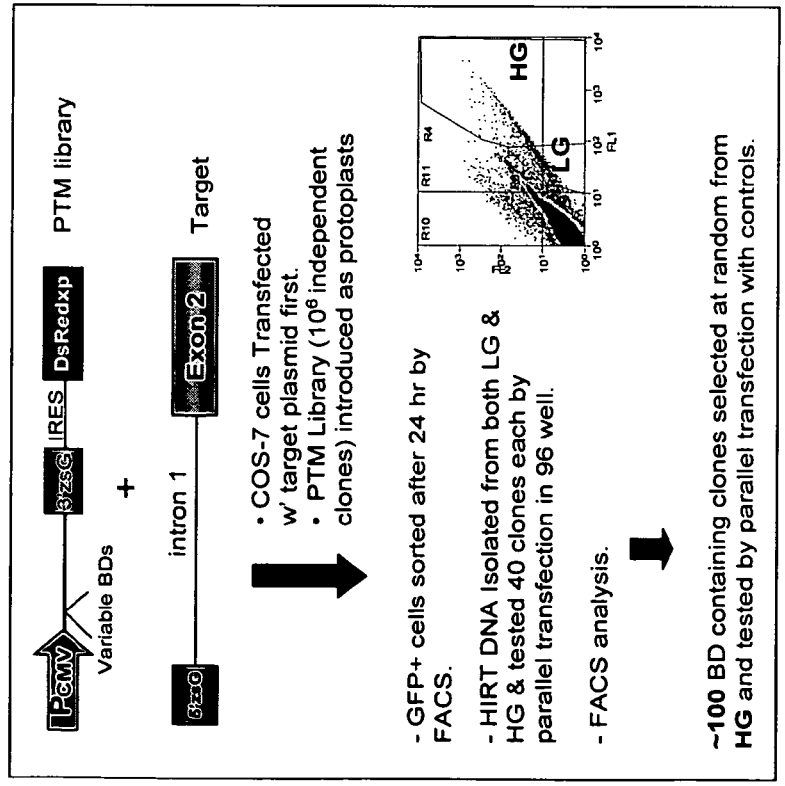
Figure 29 Schematic illustration of HCS steps.

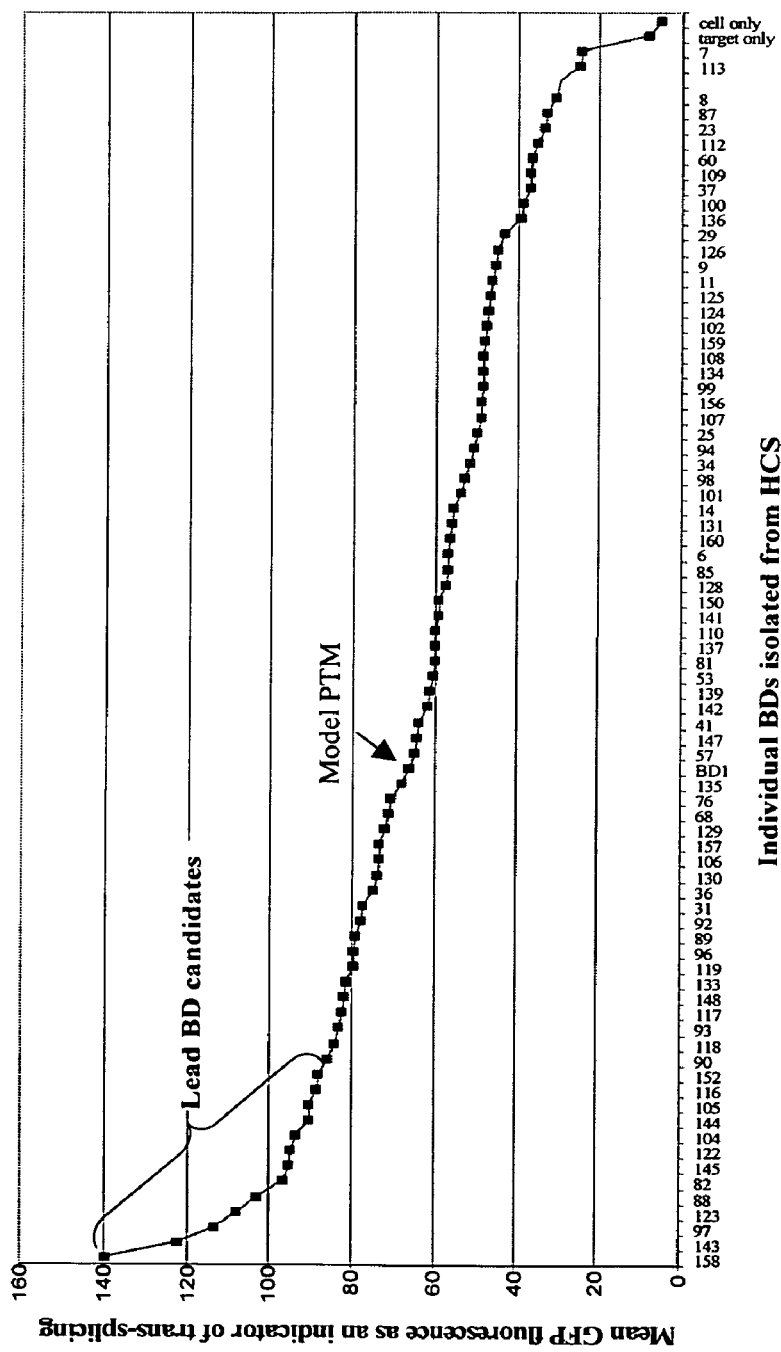
Figure 30 *Trans*-splicing efficiency of PTMs selected from HCS for mouse albumin target.

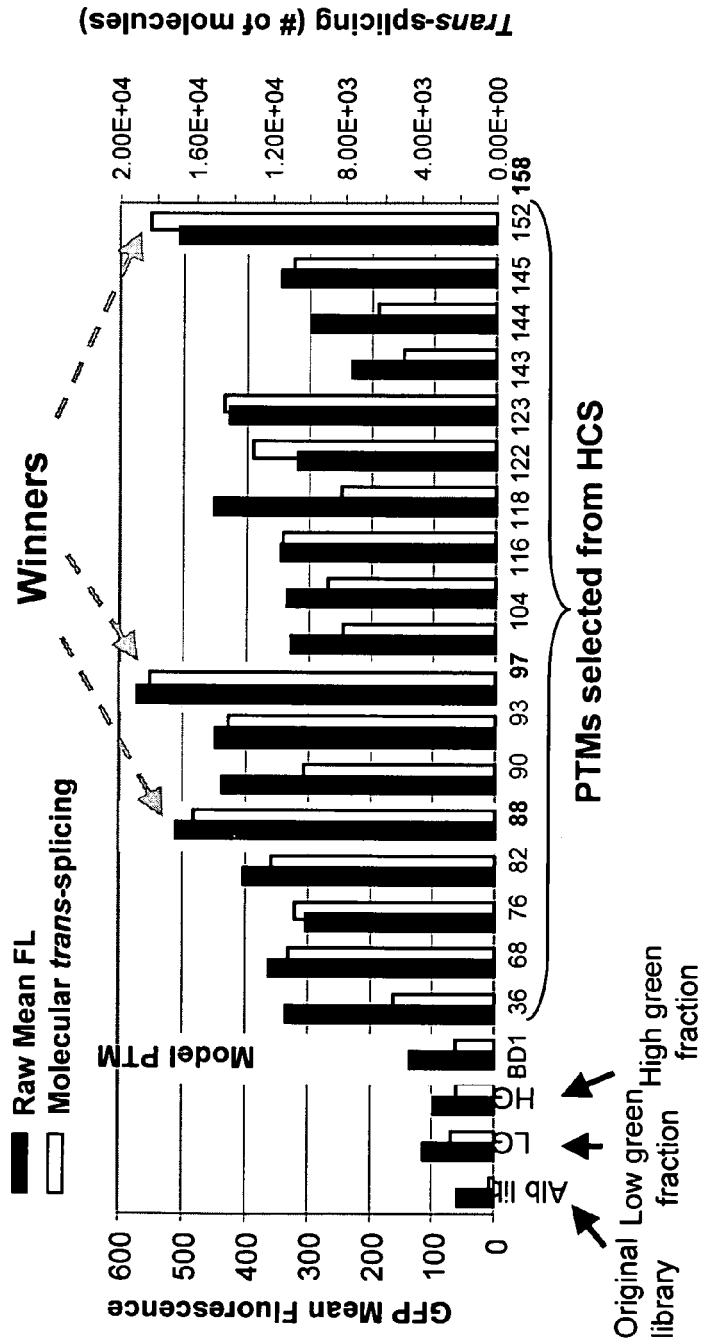
Figure 31 *Trans*-splicing efficiency of top 20 PTMs selected from the HCS assessed by FACS and qRT-PCR.

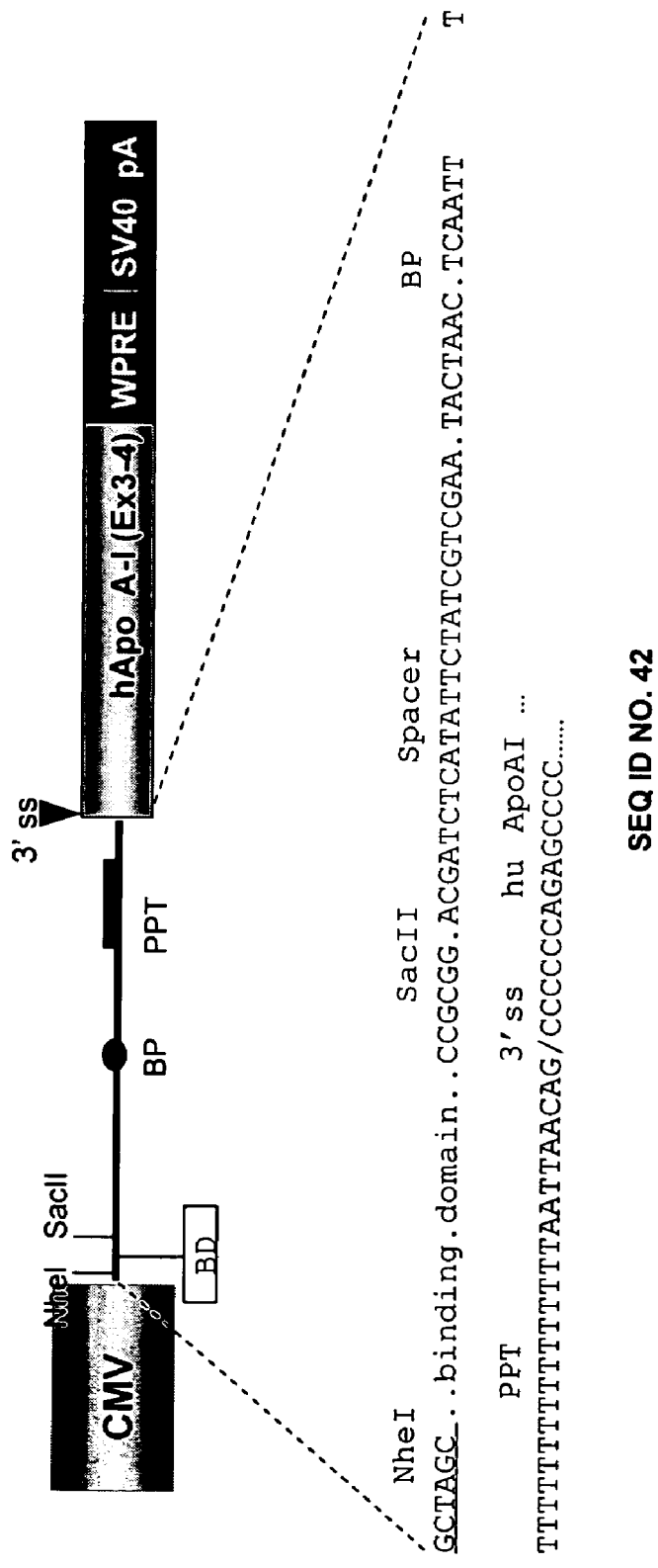
Figure 32 Schematic illustration of human Apo A-I PTM expression cassette used for *in vitr* POP studies.

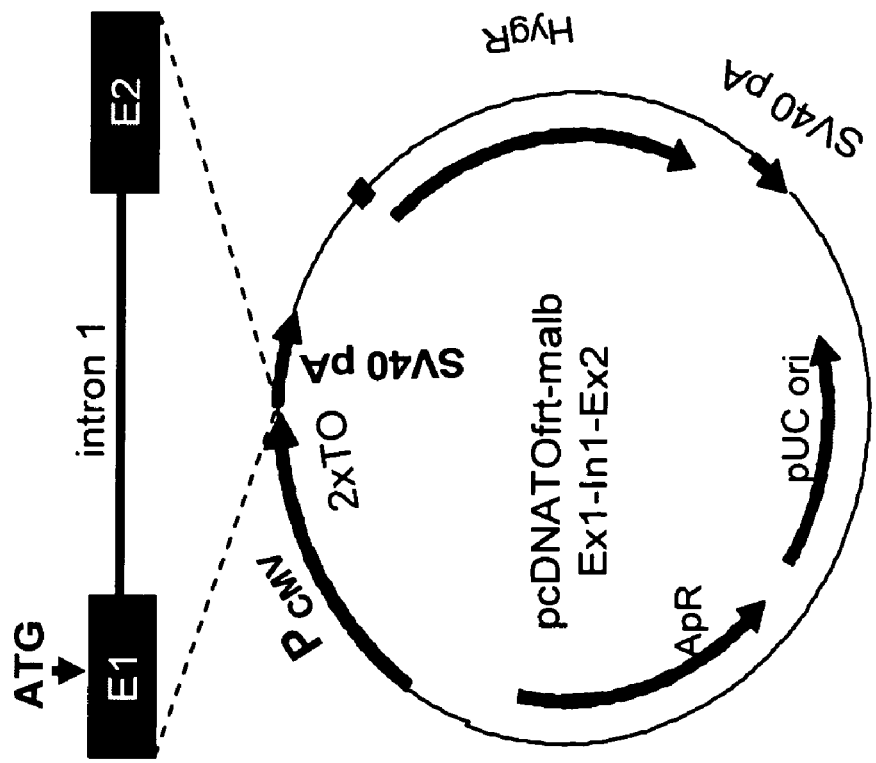
Figure 33 Schematic diagram of the mouse albumin mini-gene pre-mRNA target.

Nucleotide and amino acid sequences of ApoAI wild type

ApoAI wild type:

```
AGAGACTGCG AGAAGGAGGT CCCCCACGGC CCTTCAGG ATG AAA GCT GCG GTG CTG ACC TTG GCC GTG CTC TTC CTG ACG GGG AGC CAG GCT CGG CAT TTC TGG CAG
                                          m   k   a   a   v   l   t   l   a   v   l   f   l   t   g   s   q   a   r   h   f   w   q

CAA GAT GAA CCC CCC CAG AGC CCC TGG GAT CGA GTG AAG GAC CTG GCC ACT GTG TAC GTG GAT GTG CTC AAA GAC AGC GGC AGA GAC TAT GTG TCC CAG TTT
q   d   e   p   p   q   s   p   w   d   r   v   k   d   l   a   t   v   y   v   d   v   l   k   d   s   g   r   d   y   v   s   q   f

GAA GGC TCC GCC TTG GGA AAA CAG CTA AAC CTT GAC AAC TGG GAC AGC GTG ACC TCC ACC TTC AGC AAG CTG CGC GAA CAG CTC GGC CCT GTG
e   g   s   a   l   g   k   q   l   n   l   d   n   w   d   s   v   t   s   t   f   s   k   l   r   e   q   l   g   p   v

ACC CAG GAG TTC TGG GAT AAC CTG GAA AAG GAG ACA GAG GGC CTG AGG CAG GAG ATG AGC AAG GAT CTG GAG GAG GTG AAG GCC AAG GTG CAG CCC TAC CTG
t   q   e   f   w   d   n   l   e   k   e   t   e   g   l   r   q   e   m   s   k   d   l   e   e   v   k   a   k   v   q   p   y   l

GAC GAC TTC CAG AAG AAG TGG CAG GAG GAG ATG GAG CTC TAC CGG CAG AAG GTG GAG CCG CTG CGC GCA GAG CTC CAA GAG GGC GCG CGC CAG AAG CTG CAC
d   d   f   q   k   k   w   q   e   e   m   e   l   y   r   q   k   v   e   p   l   r   a   e   l   q   e   g   a   r   q   k   l   h nt 555 (C>T converts Wild type to Milano)
GAG CTG CAA GAG AAG CTG AGC CCA CTG GGC GAG GAG ATG CGC GAC CGC GCC CGC GCC CAT GTG GAC GCG CTG CGC ACG CAT CTG GCC CCC TAC AGC GAC GAG
e   l   q   e   k   l   s   p   l   g   e   e   m   r   d   r   a   r   a   h   v   d   a   l   r   t   h   l   a   p   y   s   d   e CTG CGC CAG CGC CTG GCC GCG CGC CTT GAG GCT CTC AAG GAG AAC GGC GGC GCC AGA CTG GCC GAG TAC CAC GCC AAG GCC ACC GAG CAT CTG AGC ACG CTC
l   r   q   r   l   a   a   r   l   e   a   l   k   e   n   g   g   a   r   l   a   e   y   h   a   k   a   t   e   h   l   s   t   l AGC GAG AAG GCC AAG CCC GCG CTC GAG GAC CTC CGC CAA GGC CTG CTG CCC GTG CTG GAG AGC TTC AAG GTC AGC TTC CTG AGC GCT CTC GAG GAG TAC ACT
s   e   k   a   k   p   a   l   e   d   l   r   q   g   l   l   p   v   l   e   s   f   k   v   s   f   l   s   a   l   e   e   y   t AAG AAG CTC AAC ACC CAG TGA GGGCCCCGCC GCCGCCCCCC TTCCCGGTGC TCAGAATAAA CGTTCCAAA GTGGG
k   k   l   n   t   q   stop
```

SEQ ID NO. 43

ApoAI-Milano: Molecular analysis have confirmed a <u>Arg</u> → Cys substitution at position 173 amino acid that converts the wild type apoAI into apoAI Milano variant.
At the nucleotide level, a single nucleotide substitution C → T was confirmed.

Figure 34

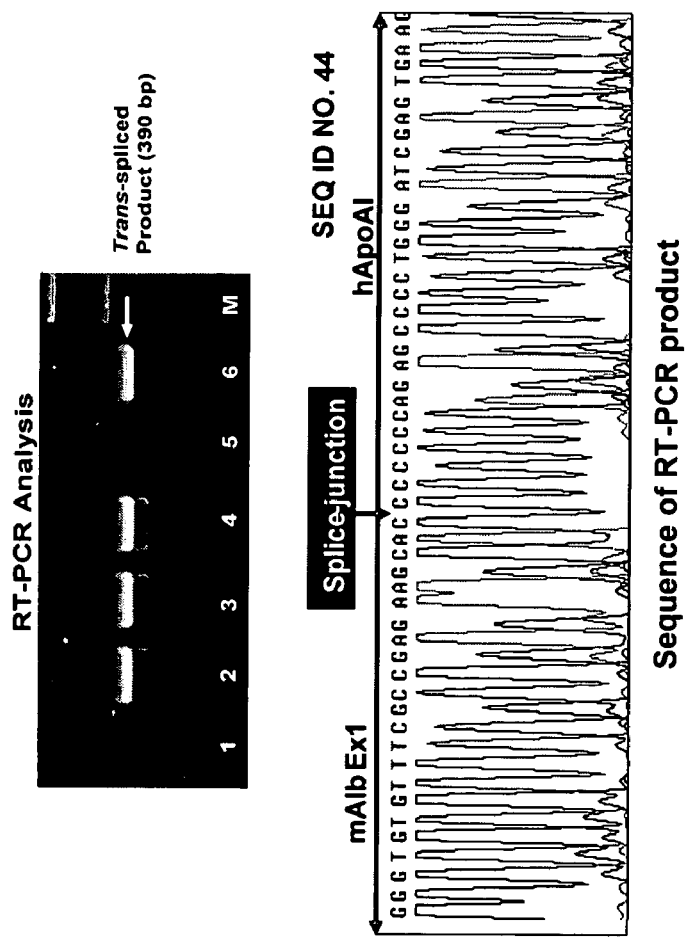
Figure 35 Evidence of precise *trans*-splicing of mAlbPTMs into albumin exon 1 in stable cells

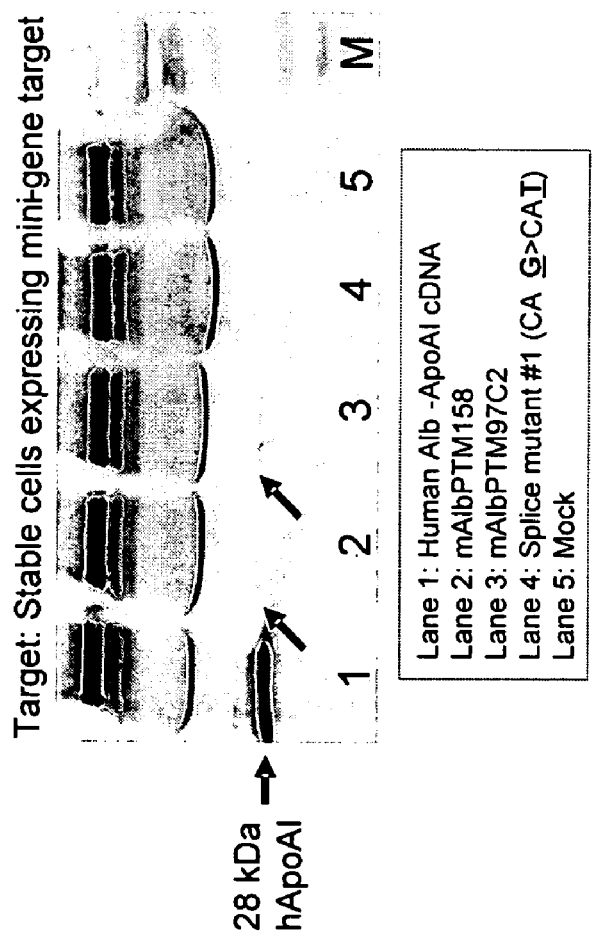
Figure 36 Detection of *trans*-spliced human Apo A-I protein by Western blot.

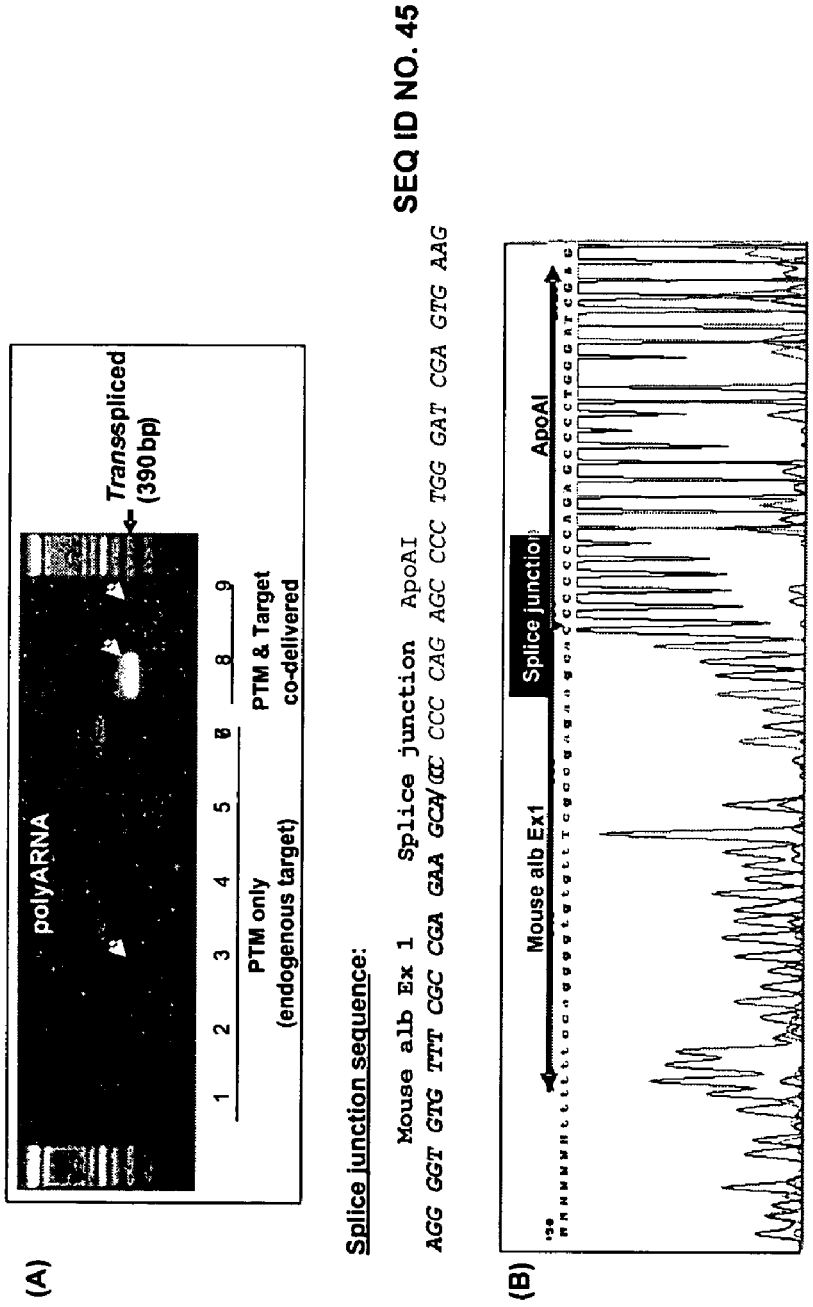
Figure 37 PTM mediated *trans*-splicing into endogenous albumin exon 1 in mice.

Strategies to eliminate albumin sequence in the final *trans*-spliced product.

PTM ApoAI sequences (human NP_000030. apolipoprotein A-I...[gi:4557321])
» SIGNAL PEPTIDE CLEAVAGE AT RER
« PRO PEPTIDE CLEAVAGE AT GOLGI Pre        Pro      Pro      hApoAI 1. MKWVTFISLLFLFSSAYS»RGVFRR«DAPRGVFRR«*DEPP*.....ApoAI sequence
   cDNA construct designed to include additional albumin propeptide (underlined) followed by the entire mature coding sequence for ApoAI. Proline (in bold) was used as a junction amino acid.

2. MKWVTFISLLFLFSSAYS»RGVFRR«DAPRHFWQQ«*DEPP*.....ApoAI sequence
   cDNA construct designed to include human ApoAI pro-peptide (underlined) in addition to albumin pro-peptide followed by the entire mature coding sequence for ApoAI. Proline (in bold) was used as a junction amino acid.

3. MKWVTFISLLFLFSSAYS»RGVFRR«DARHFWQQ«*DEPP*.....ApoAI sequence
   cDNA construct designed to include human ApoAI pro-peptide (underlined) in addition to albumin pro-peptide followed by the entire mature coding sequence for ApoAI. The additional ApoAI pro-peptide was linked directly into albumin sequence without Proline.

With the presence of a second pro-peptide (albumin or ApoAI), these chimeric proteins will now undergo a second cleavage resulting in the final trans-spliced product that is identical to the wild type ApoAI sequence i.e., without any albumin sequence.

Similarly, PTMs can also be engineer to include peptidase cleavage site(s) or signal peptides which after trans-splicing would be recognized and cleaved to release the final product that is identical to ApoAI sequence i.e., without any albumin sequence.

Figure 39. Schematic showing the strategies to eliminate albumin sequence in the final *trans*-spliced product.

Human ApoAI Produced in Mice
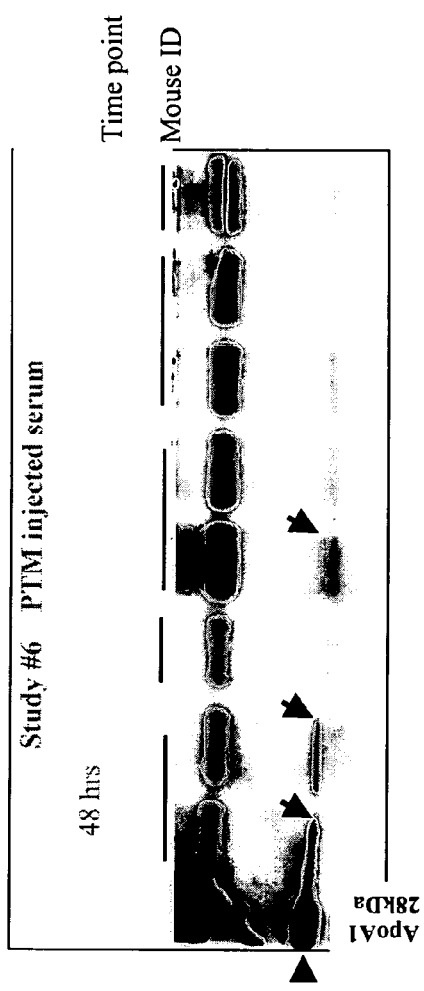
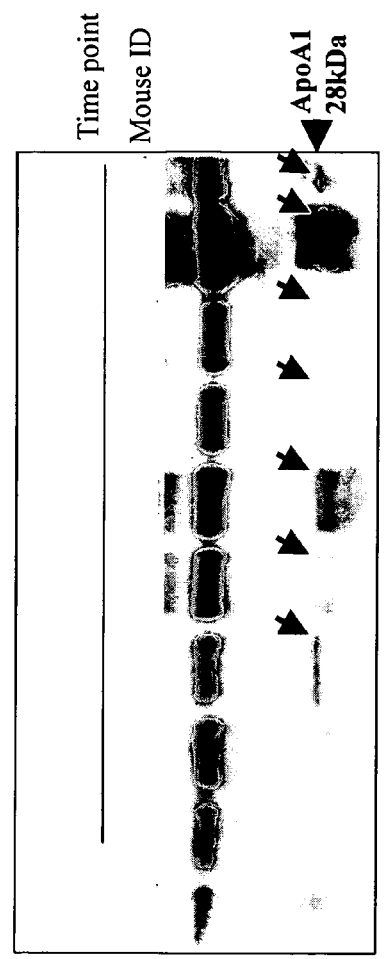
Study #6
- Minicircle-PTM (75 μg/mouse)
- Time point: 48-2 wks
- Mice: C57BL/6 males
- 50 μl serum immuno-precipitated using monoclonal antibody to human ApoA1 followed by Western w/ the same antibody.
Study #7
- Minicircle-PTM (75 μg/mouse)
- Time point: 48 hrs
- Mice: C57BL/6 females
- IP and Western conditions same as above.
Figure 43

Trans-spliced mAlb-E7scFv is translated and secreted
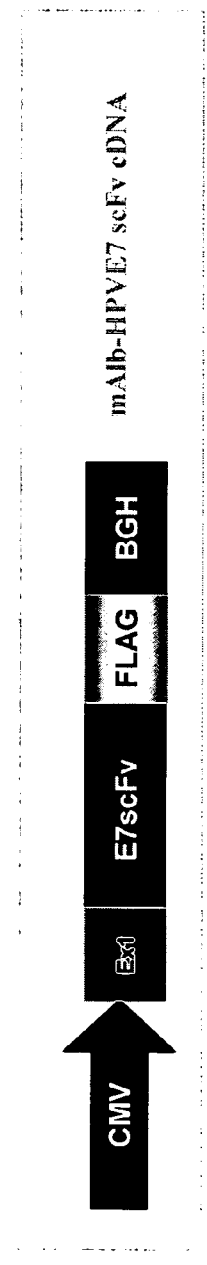
The mAlbEx1-E7scFv protein is expressed, processed and secreted properly in both hepatoma and COS-7 cells.
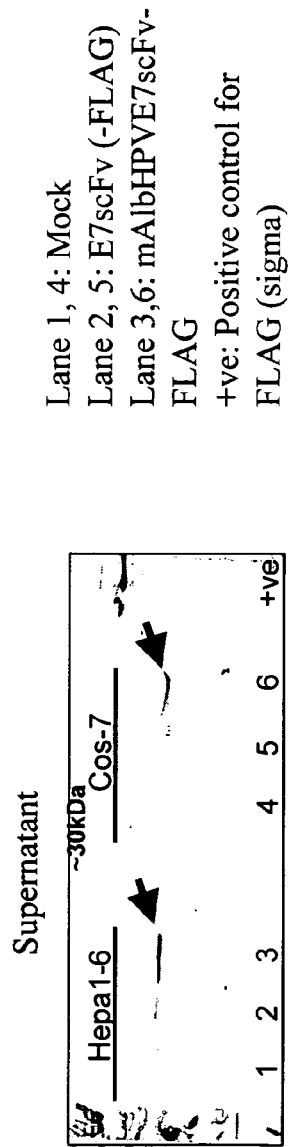
Lane 1, 4: Mock
Lane 2, 5: E7scFv (-FLAG)
Lane 3,6: mAlbHPVE7scFv-FLAG
+ve: Positive control for FLAG (sigma)
Figure 49

Trans-spliced Antibody Product is Functional

<u>Trans-spliced scFv protein is functional:</u>

➤ Cervical cancer cells, SiHa, or the matching control cells that do not express E7 oncoprotein was transfected with mAlb-E7scFv cDNA plasmid. Cells were grown for 5 days and assayed for cell survival by MTT assay.

➤ Results: ~70% cell killing was observed with SiHa cervical cancer cells compared to control cells which do not express E7 oncoprotein.

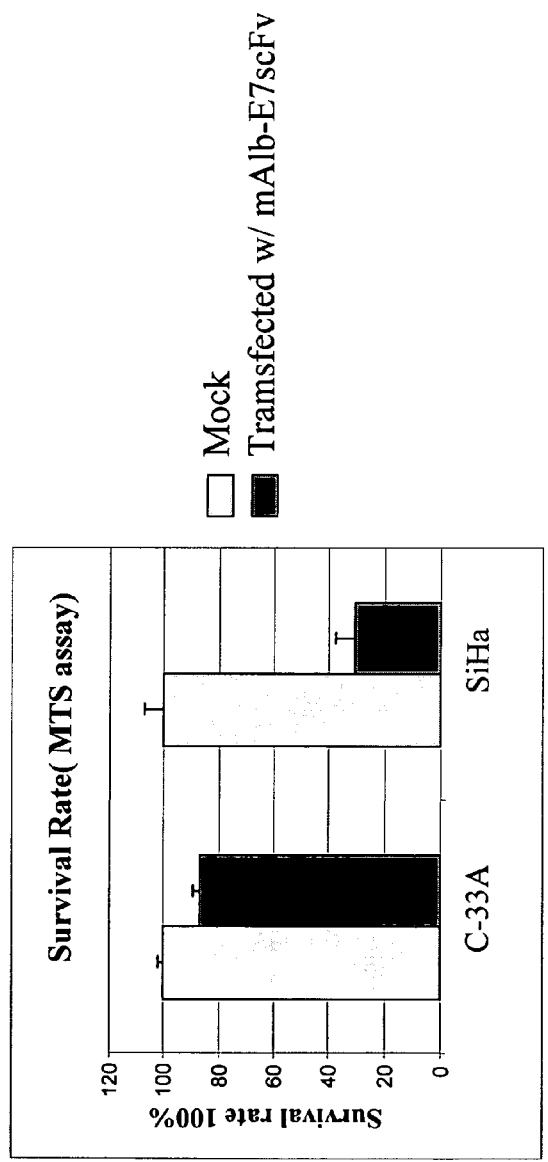

Figure 50

Levels of pre-mRNA in Mouse Liver: albumin is 270x Higher Than FVIII

| Target | Pre-mRNA | mRNA |
|---|---|---|
| | #molecules/50ng RNA | # molecules/50ng RNA |
| Albumin | $8.1 \times 10^4$ | $4.7 \times 10^7$ |
| Factor VIII | $3.0 \times 10^2$ | ND |

Figure 51

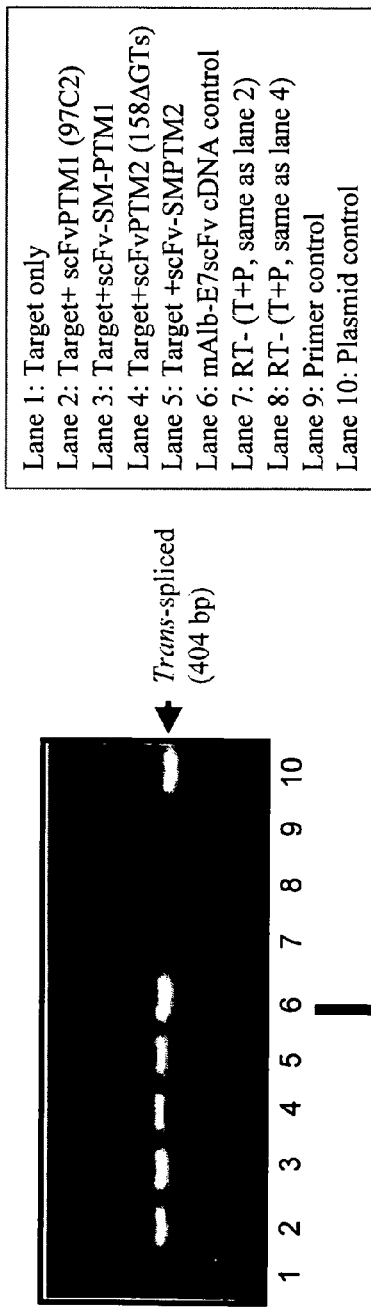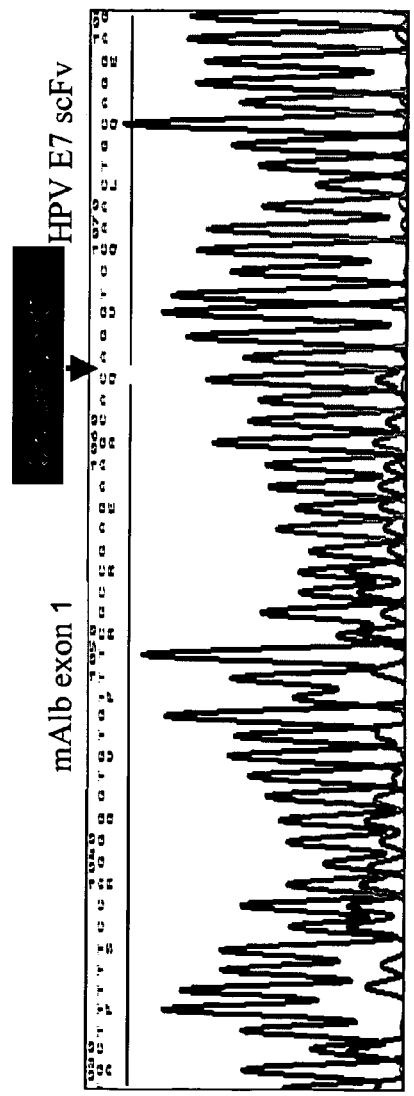
Figure 52

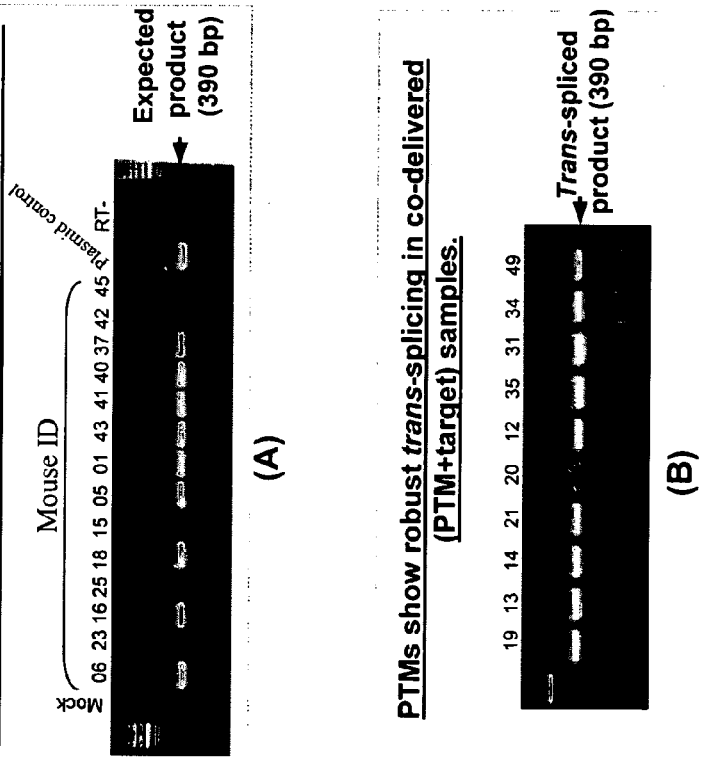
Fig. 56. RT-PCR results showing the presence of (A) mouse albumin-human Apo A-I mRNA and (B) *trans*-spliced mRNA in mice.

*In Vivo* POP Studies in Normal Mice - PCR Results
➤ PTM only samples analyzed for trans-splicing into endogenous albumin target pre-mRNA
➤ 10/13 mice were positive for trans-splicing.
• 03, 09, 22; questionable injection
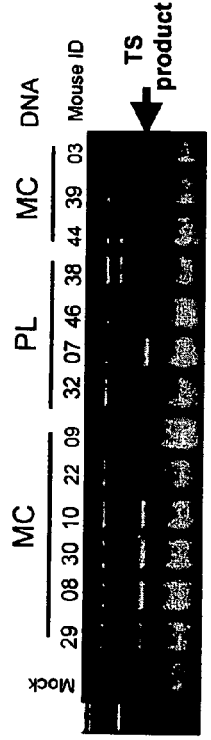
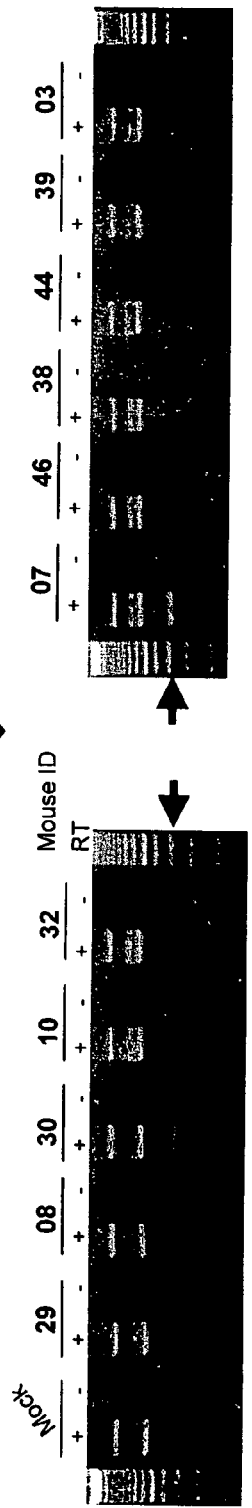
Re-analysis of positive samples along with RT(-) controls
Fig. 56C.

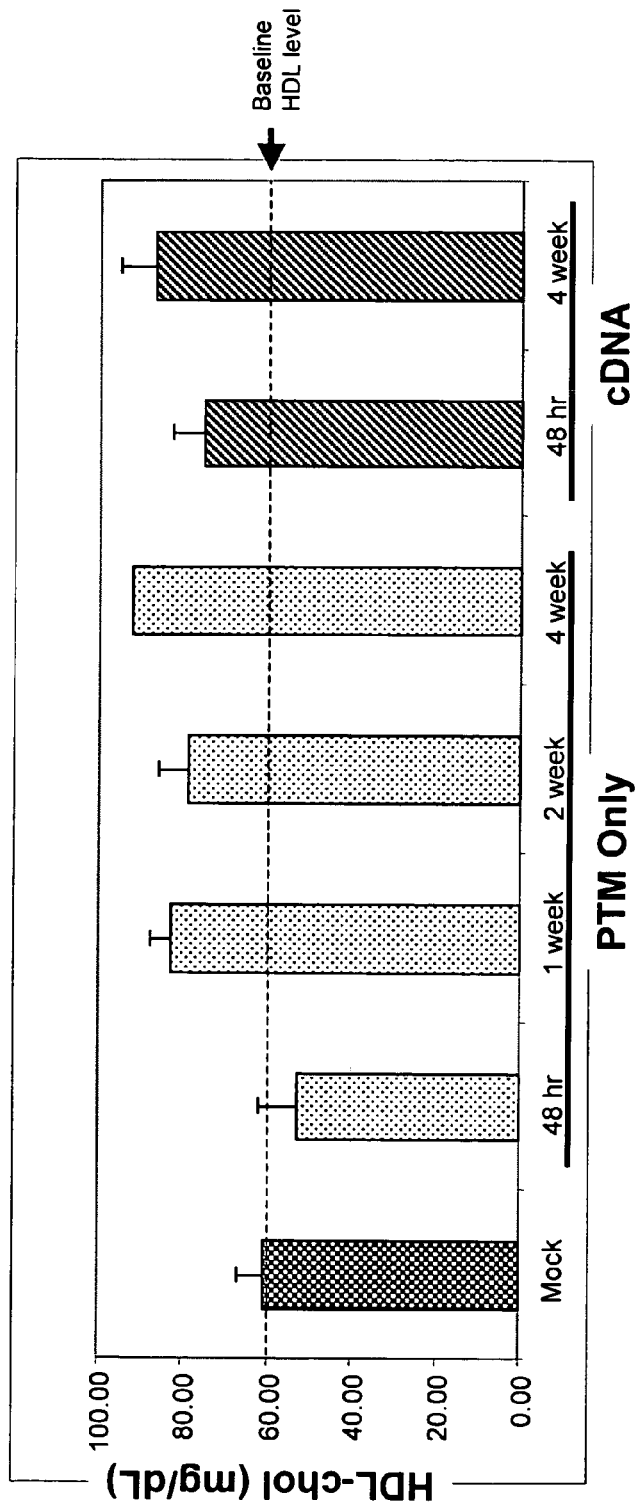
Fig. 59. HDL analysis of serum samples from mice injected with PTM and cDNA plasmids.

TARGETED *TRANS*-SPLICING OF HIGHLY ABUNDANT TRANSCRIPTS FOR IN VIVO PRODUCTION OF RECOMBINANT PROTEINS

CROSS REFERENCE TO RELATED APPLICATION

Benefit Under 35 U.S.C. §119 to U.S. Provisional Patent Application No. 60/617,324 filed on Oct. 8, 2004, the disclosure of which is hereby incorporated by reference in its entity, is claimed. This is a continuation of U.S. application Ser. No. 11/141,447 filed May 31, 2005 which is a continuation-in-part of U.S. patent application Ser. No. 11/041,155 filed Jan. 21, 2005 each of the disclosures are hereby incorporated by reference in their entireties.

INTRODUCTION

The present invention provides methods and compositions for generating novel nucleic acid molecules through RNA trans-splicing that target abundantly expressed precursor messenger RNA molecule (target pre-mRNA) and contain the coding sequence of a protein or polypeptide of interest. The compositions of the invention include pre-trans-splicing molecules (PTMs) designed to interact with the target pre-mRNA, and mediate a trans-splicing reaction, resulting in the generation of a novel chimeric RNA molecule (chimeric RNA) capable of encoding a protein or polypeptide of interest. In particular, the target pre-mRNA is albumin or casein pre-mRNA. The purpose of the invention is to develop in vivo production of chimeric RNA molecules comprising sequences that encode a protein or polypeptide of interest that may be of therapeutic, diagnostic or industrial importance in a host animal from which the protein can be recovered in bulk amounts. The present invention also provides methods for the large-scale production of proteins or polypeptides of interest.

The compositions of the invention further include recombinant vector systems capable of expressing the PTMs of the invention and cells expressing said PTMs. The methods of the invention encompass contacting the PTMs of the invention with the target pre-mRNA under conditions in which a portion of the PTM is trans-spliced to a portion of the target pre-mRNA to form a chimeric RNA molecule that would express a protein or polypeptide of interest.

BACKGROUND OF THE INVENTION

Production of Large Scale Recombinant Proteins

Recombinant protein production technology provides for the generation of large quantities of protein for function and structure analysis, industrial uses, drug design, diagnostics, therapy, and vaccines. Mammalian and insect expression systems have been employed to produce biologically active recombinant proteins in a short period of time with high yields. Bioreactors containing cells incubated under specific conditions have been fruitful in large-scale production of recombinant proteins.

Transgenic dairy cattle and transgenic goats offer alternatives to bioreactors as a high volume source of recombinant proteins. Recombinant proteins of interest are expressed in the milk of these transgenic animals, which can be collected and harvested for the recombinant protein of interest. Cattle can produce over 9000 liters of milk per years and are capable of producing large amounts of proteins in their milk, which is comparable to the amounts generated in bioreactors. Cattle can express complex proteins that cannot be produced economically by cell culture. Large-scale production of valuable therapeutic proteins, with flexible scale-up and significantly lower capital costs and risks are also possible. Cattle are also a safe and renewable source of recombinant proteins or polypeptides. It enables the manufacture of complex or unique molecules that cannot be produced efficiently by any other method.

Goats are also potential host animals for the production of large scale therapeutic proteins (Baldassarre et al., State of the art in the production of transgenic goats. Reprod Fertil Dev. 2004, 16:465-70). Goats have been shown to express various proteins in their milk, including, inter alia, human growth hormone, insulin, spider silk, antithrombin III, tissue plasminogen activator, and α1-antitrypsin. Genzyme Transgenics, for example, has expressed over 14 proteins in transgenic goats at greater than 1 g/L of milk (Rathin C. Das, Production of therapeutic proteins from transgenic animals. BioBusiness, February 2001, pp. 60-64).

RNA Splicing

DNA sequences in the chromosome are transcribed into pre-mRNAs that contain coding regions (exons) and generally also contain intervening non-coding regions (introns). Introns are removed from pre-mRNAs in a precise process called cis-splicing (Chow et al., 1977, *Cell* 12:1-8; and Berget, S. M. et al., 1977, *Proc. Natl. Acad. Sci. USA* 74:3171-3175). Splicing takes place as a coordinated interaction of several small nuclear ribonucleoprotein particles (snRNP's) and many protein factors that assemble to form an enzymatic complex known as the spliceosome (Moore et al., 1993, in The RNA World, R. F. Gestland and J. F. Atkins eds. (Cold Spring Harbor Laboratory Press, Cold Spring Harbor, N.Y.); Kramer, 1996, *Annu. Rev. Biochem.*, 65:367-404; Staley and Guthrie, 1998, *Cell* 92:315-326).

In most cases, the splicing reaction occurs within the same pre-mRNA molecule, which is termed cis-splicing. Splicing between two independently transcribed pre-mRNAs is termed trans-splicing. (See FIG. 1) Trans-splicing was first discovered in trypanosomes (Sutton & Boothroyd, 1986, *Cell* 47:527; Murphy et al., 1986, *Cell* 47:517) and subsequently in nematodes (Krause & Hirsh, 1987, *Cell* 49:753); flatworms (Rajkovic et al., 1990, *Proc. Nat'l. Acad. Sci. USA*, 87:8879; Davis et al., 1995, *J. Biol. Chem.* 270:21813) and in plant mitochondria (Malek et al., 1997, *Proc. Nat'l. Acad. Sci. USA* 94:553). In the parasite *Trypanosoma brucei*, all mRNAs acquire a splice leader (SL) RNA at their 5' termini by trans-splicing. A 5' leader sequence is also trans-spliced onto some genes in *Caenorhabditis elegans*. This mechanism is appropriate for adding a single common sequence to many different transcripts.

The mechanism of splice leader trans-splicing, which is nearly identical to that of conventional cis-splicing, proceeds via two phosphoryl transfer reactions. The first causes the formation of a 2'-5' phosphodiester bond producing a 'Y' shaped branched intermediate, equivalent to the lariat intermediate in cis-splicing. The second reaction, exon ligation, proceeds as in conventional cis-splicing. In addition, sequences at the 3' splice site and some of the snRNPs that catalyze the trans-splicing reaction, closely resemble their counterparts involved in cis-splicing.

Trans-splicing may also refer to a different process, where an intron of one pre-mRNA interacts with an intron of a second pre-mRNA, enhancing the recombination of splice sites between two conventional pre-mRNAs. This type of trans-splicing was postulated to account for transcripts encoding a human immunoglobulin variable region sequence linked to the endogenous constant region in a transgenic mouse (Shimizu et al., 1989, Proc. Nat'l. Acad. Sci. USA 86:8020). In addition, trans-splicing of c-myb pre-RNA has been demonstrated (Vellard, M. et al. Proc. Nat'l. Acad. Sci., 1992 89:2511-2515) and more recently, RNA transcripts from cloned SV40 trans-spliced to each other were detected in cultured cells and nuclear extracts (Eul et al., 1995, EMBO. J. 14:3226). However, naturally occurring trans-splicing of mammalian pre-mRNAs is thought to be a rare event (Flouriot G. et al., 2002 J. Biol. Chem: Finta, C. et al., 2002 J. Biol Chem 277:5882-5890).

In vitro trans-splicing has been used as a model system to examine the mechanism of splicing by several groups (Konarska & Sharp, 1985, Cell 46:165-171 Solnick, 1985, Cell 42:157; Chiara & Reed, 1995, Nature 375:510; Pasman and Garcia-Blanco, 1996, Nucleic Acids Res. 24:1638). Reasonably efficient trans-splicing (30% of cis-spliced analog) was achieved between RNAs capable of base pairing to each other, splicing of RNAs not tethered by base pairing was further diminished by a factor of 10. Other in vitro trans-splicing reactions not requiring obvious RNA-RNA interactions among the substrates were observed by Chiara & Reed (1995, Nature 375:510), Bruzik J. P. & Maniatis, T. (1992, Nature 360:692) and Bruzik J. P. and Maniatis, T., (1995, Proc. Nat'l. Acad. Sci. USA 92:7056-7059). These reactions occur at relatively low frequencies and require specialized elements, such as a downstream 5' splice site or exonic splicing enhancers.

In addition to splicing mechanisms involving the binding of multiple proteins to the precursor mRNA which then act to correctly cut and join RNA, a third mechanism involves cutting and joining of the RNA by the intron itself, by what are termed catalytic RNA molecules or ribozymes. The cleavage activity of ribozymes has been targeted to specific RNAs by engineering a discrete "hybridization" region into the ribozyme. Upon hybridization to the target RNA, the catalytic region of the ribozyme cleaves the target. It has been suggested that such ribozyme activity would be useful for the inactivation or cleavage of target RNA in vivo, such as for the treatment of human diseases characterized by production of foreign of aberrant RNA. In such instances small RNA molecules are designed to hybridize to the target RNA and by binding to the target RNA prevent translation of the target RNA or cause destruction of the RNA through activation of nucleases. The use of antisense RNA has also been proposed as an alternative mechanism for targeting and destruction of specific RNAs.

Using the Tetrahymena group I ribozyme, targeted trans-splicing was demonstrated in E. coli. (Sullenger B. A. and Cech. T. R., 1994, Nature 341:619-622), in mouse fibroblasts (Jones, J. T. et al., 1996, Nature Medicine 2:643-648), human fibroblasts (Phylacton, L. A. et al. Nature Genetics 18:378-381) and human erythroid precursors (Lan et al., 1998, Science 280:1593-1596). For a review of clinically relevant technologies to modify RNA, see Sullenger and Gilboa, 2002 Nature 418:252-8. The present invention relates to the use of targeted trans-splicing mediated by native mammalian splicing machinery, i.e., spliceosomes, to reprogram or alter the coding sequence of a targeted mRNA.

U.S. Pat. Nos. 6,083,702, 6,013,487 and 6,280,978 describe the use of PTMs to mediate a trans-splicing reaction by contacting a target precursor mRNA to generate novel chimeric RNAs. All references cited herein are hereby incorporated by reference in their entirety.

SUMMARY OF THE INVENTION

The present invention provides methods and compositions for generating novel nucleic acid molecules through RNA trans-splicing that target an abundantly expressed precursor messenger RNA molecule (target pre-mRNA) and contain the coding sequence of a protein or polypeptide of interest. The compositions of the invention include pre-trans-splicing molecules (PTMs) designed to interact with the abundantly expressed target pre-mRNA, and mediate a trans-splicing reaction resulting in the generation of novel chimeric RNA molecule (chimeric RNA) capable of encoding a protein or polypeptide of interest. The abundantly expresses target pre-mRNA may be selected from those coding for albumin, casein, myosin and fibroin, with albumin being preferred. The purpose of the invention is to develop in vivo production of chimeric RNA molecule comprising sequences that encode a protein or polypeptide of interest that may be of therapeutic, diagnostic or industrial importance in a host animal from which the polypeptide or protein can be recovered in bulk amounts.

The compositions of the invention further include recombinant vector systems capable of expressing the PTMs of the invention and cells expressing said PTMs. The methods of the invention encompass contacting the PTMs of the invention with the target pre-mRNA under conditions in which a portion of the PTM is trans-spliced to a portion of the target pre-mRNA to form a chimeric RNA molecule that would express a protein or polypeptide of interest.

The present invention provides for methods of large scale bulk productions of proteins or polypeptides of interest.

BRIEF DESCRIPTION OF THE DRAWINGS

FIG. 10 shows a nucleotide sequence of the trans-spliced mouse albumin-HPV16 anti-E7 scFv mRNA.

Indicates point mutation (deletion) that result in premature termination. No full-length protein was detected on Western blot.

Figure 21:
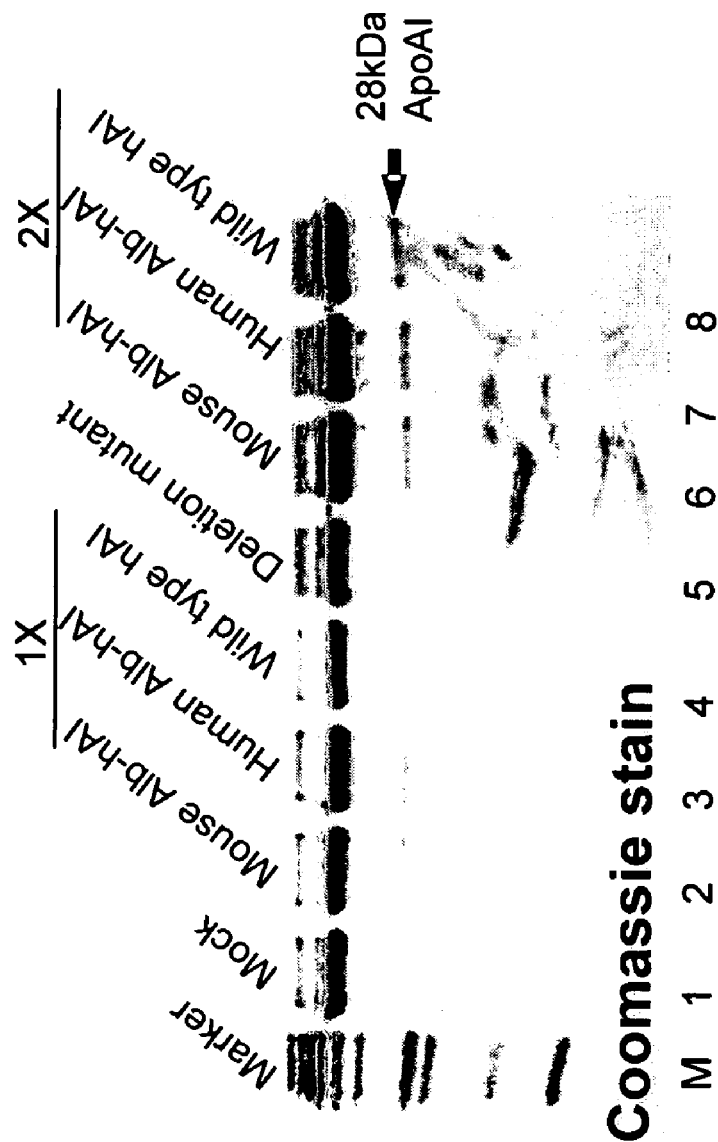

FIG. 21 SDS gels showing human Apo A-1 expression in 293 cells.

Figure 22:
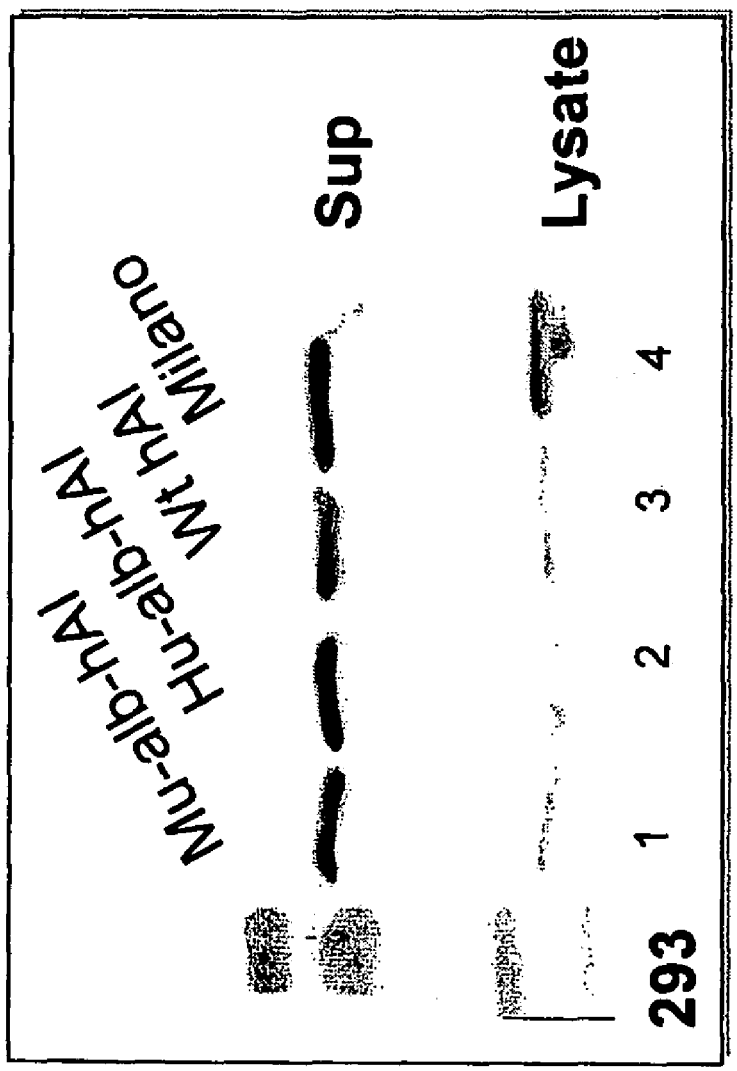

FIG. 22 Western blot showing the expression and secretion of mature human Apo A-I protein in 293 cells. Lane 1, mouse Alb-hAI; lane 2, human Alb-hAI; lane 3, wt Apo A-I and lane 4, milano variant. Upper panel, protein in supernatant and lower panel, protein in cell lysate.

FIG. 23 Cholesterol efflux in 293 cells demonstrating the expression of functional human Apo A-1 protein.

FIG. 24A Schematic of FACS-based PTM selection strategy.

FIG. 24B Comparison of high capacity screening (HCS) protocols.

Figure 5:
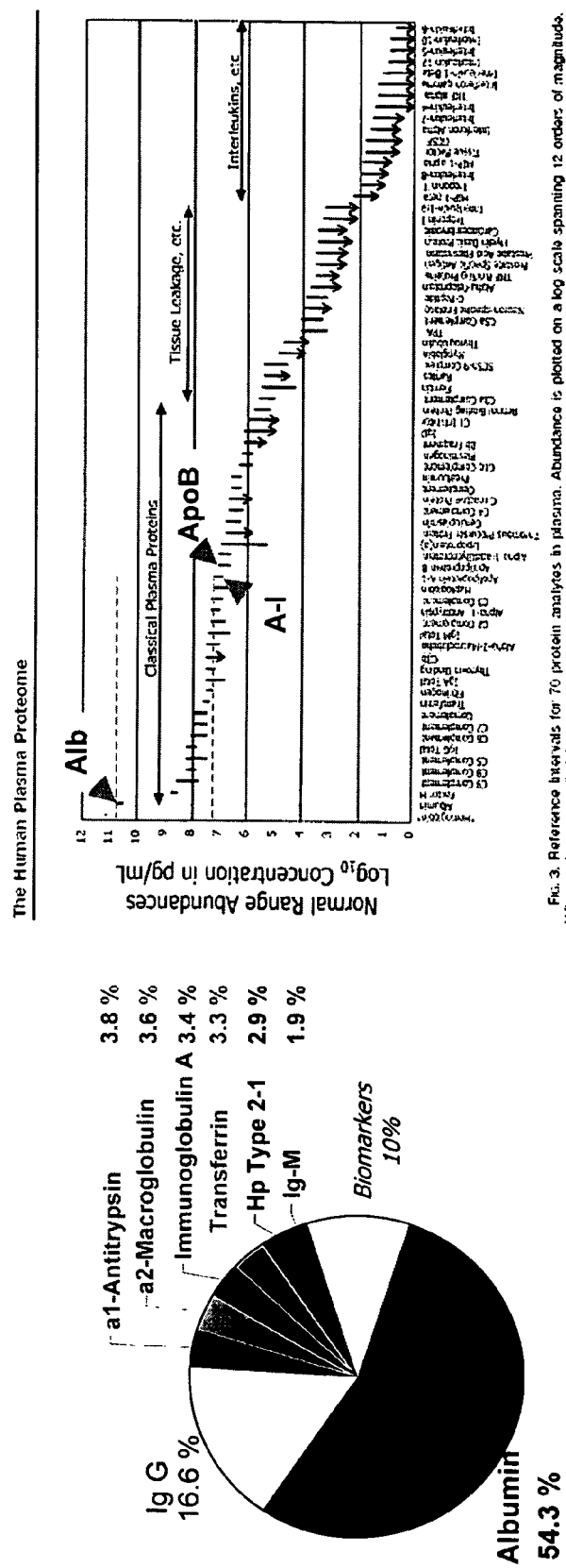
FIG. 5 shows the components of human plasma.

FIG. 25 5' GFP-Albln1Ex2 Pre-mRNA Target Sequence. Nucleotide sequence of 5' GFP-Albln1Ex2 gene for in vitro studies. Sequences shown in italics indicate first half of the coding sequence for GFP fluorescent protein followed by human albumin intron 1 and exon 2 sequences (underlined). "/" indicates 5' and 3' splice junctions.

FIG. 26 schematic diagram of the pre-mRNA target used in the HCS (SD, splice donor site; SA, splice acceptor site. Dotted lines indicate target cis-splicing).

Figure 27:
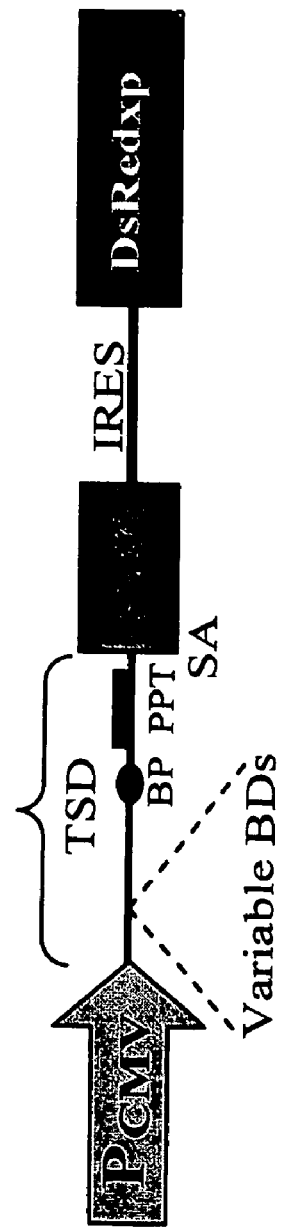

FIG. 27 Schematic illustration of the PTM cassette used in the HCS. PTM cassette consists of a trans-splice domain including (TSD): variable BDs, short spacer, BP, PPT, 3' half of the coding sequence for zsG, IRES followed by the full length coding sequence for second reporter DsRedExpress. Abbreviations: 3'zsG, 3' half of the zsGreen fluorescent protein coding sequence; IRES, internal ribosome entry site, BD, binding domain; BP, branch point; PPT, polypyrimidine tract. SA, splice acceptor site.

FIG. 28 is a PCR analysis showing the cloning efficiency and diversity of the mouse albumin binding domain (BD) library.

FIG. 29 illustrates the high capacity screening (HCS) method.

FIG. 30 Trans-splicing efficiency of PTMs selected from HCS for mouse albumin target.

FIG. 31 Bar graph showing trans-splicing efficiency and GFP fluorescence of various PTMs selected from HCS.

FIG. 32 Schematic showing the human Apo A-1 PTM expression cassette used for proof of principle in vitro studies.

FIG. 33 shows a schematic diagram of the mouse albumin mini-gene pre-mRNA target.

FIG. 34 shows the nucleotide and amino acid sequence of wild type ApoA-1.

FIG. 35 shows trans-splicing of mAlbPTMs into albumin exon 1 in stable cells.

FIG. 36 Western blot analysis of trans-spliced human Apo A-1 protein.

FIG. 37 PTM-mediated trans-splicing into endogenous albumin exon 1 in mice.

Figure 38:
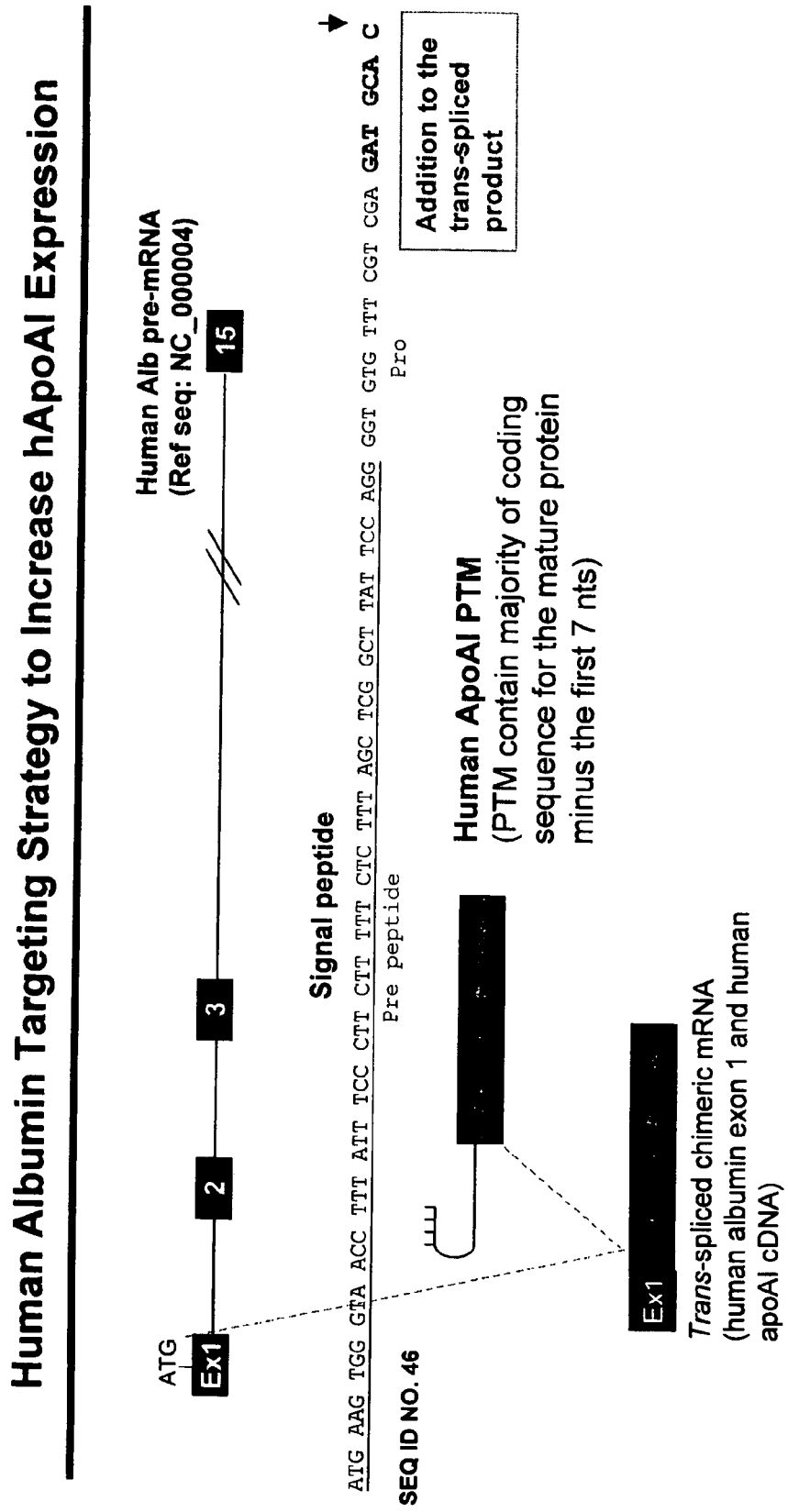

FIG. 38 shows a schematic diagram showing a human albumin targeting strategy to increase ApoA1 expression. Nucleotides in bold, indicate the human albumin sequence (7 nts) that are added to final trans-spliced product.

FIG. 39 shows the strategies to eliminate albumin sequence in the final trans-spliced product.

Figure 40:
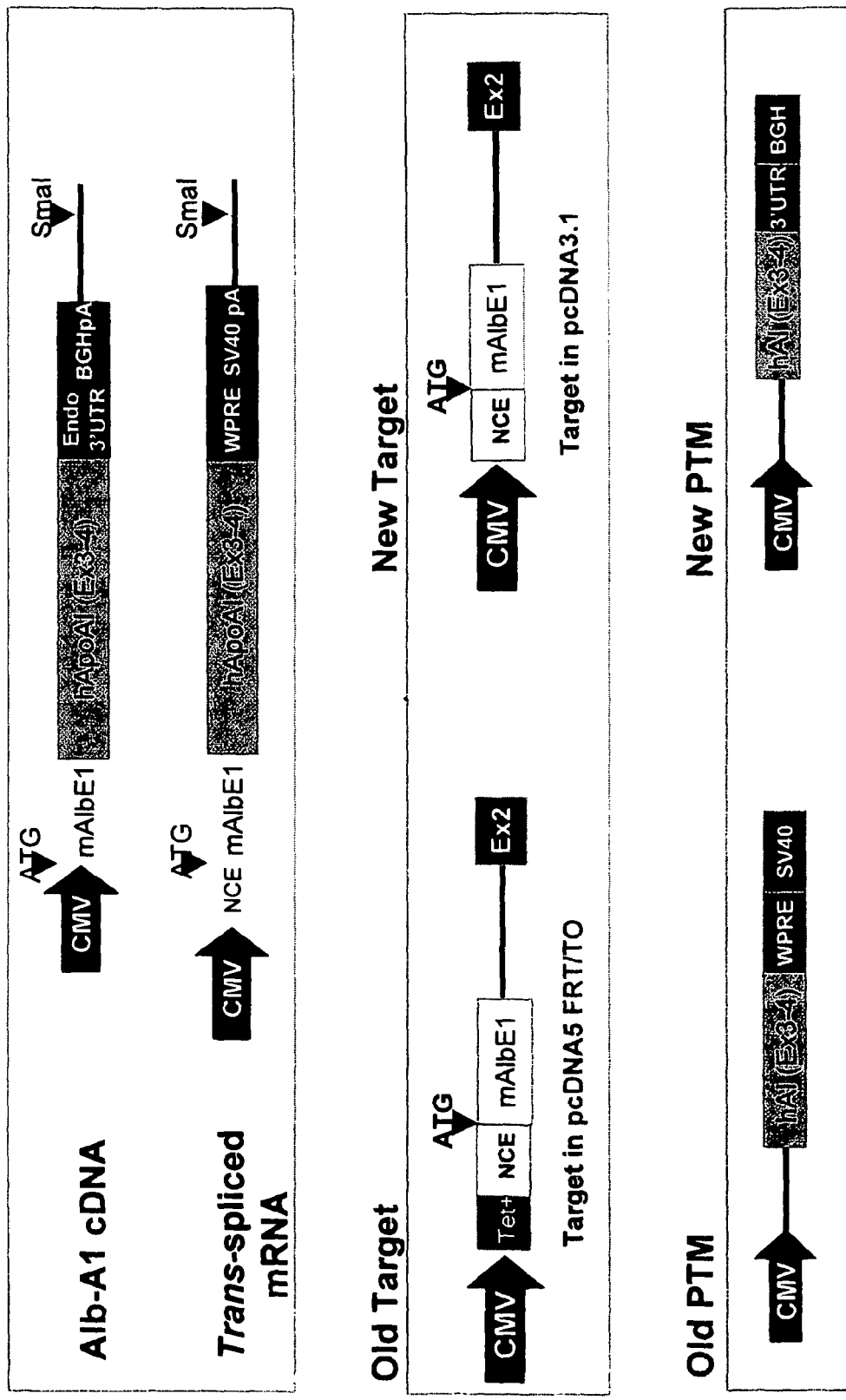

FIG. 40 shows albumin-human Apo A-I cDNA, trans-spliced mRNA, old and new PTM and targets that may be used according to the present invention (NCE, non-coding exon; hAI, human Apo A-I and Ex, exon).

Figure 41:
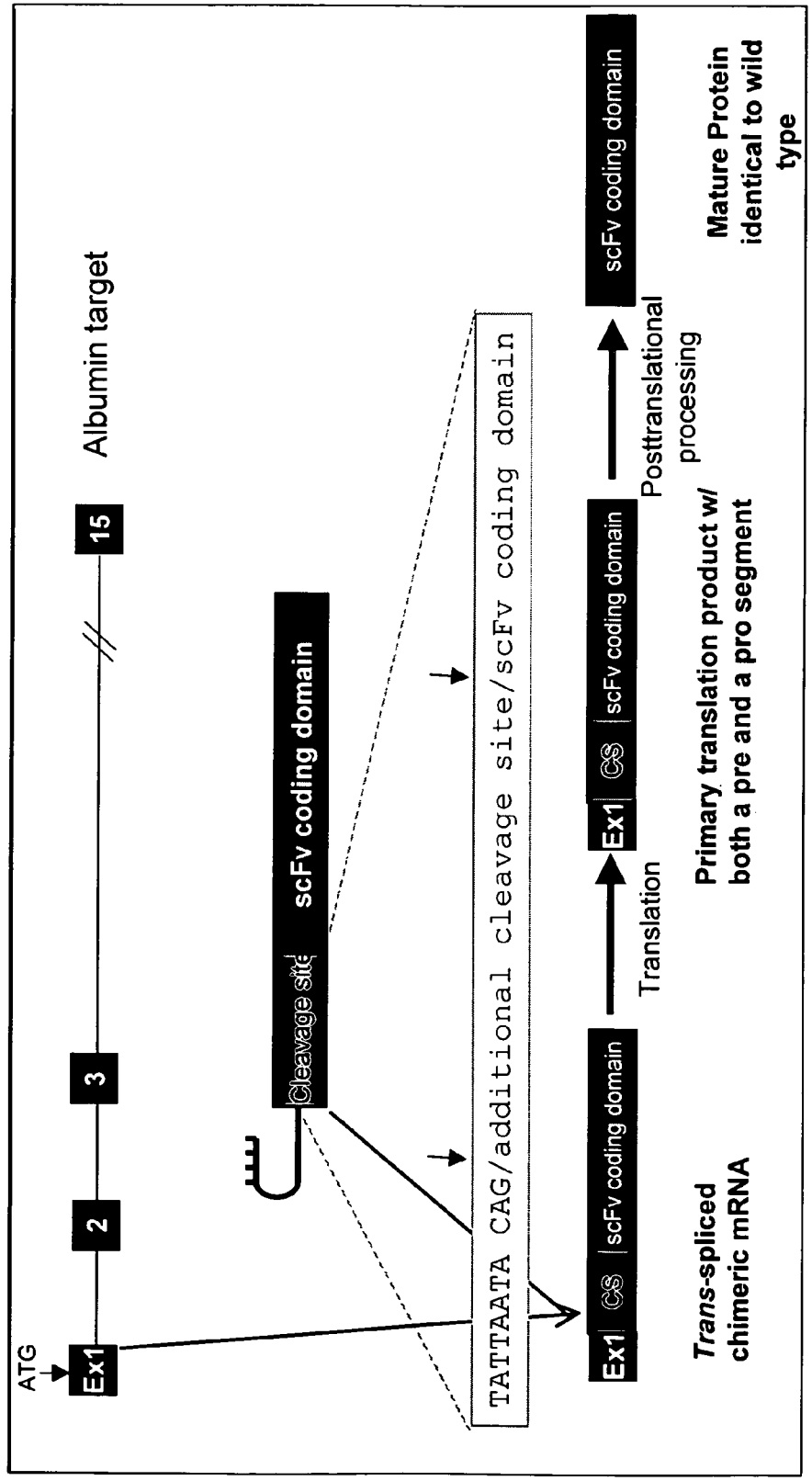

FIG. 41 shows a schematic illustration of trans-splicing strategy to eliminate albumin sequence in the final product. Ex1, exon 1 of albumin; CS, additional cleavage site.

Figure 42:
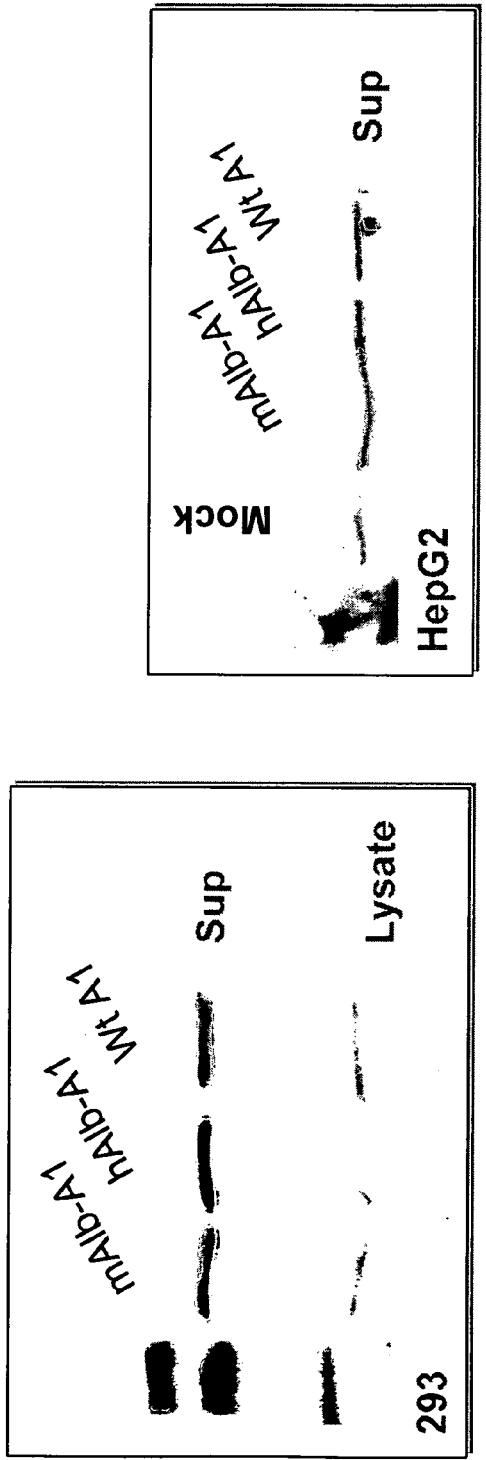

FIG. 42 shows western analysis of mouse and human Alb-hApoA1 trans-spliced protein.

FIG. 43 shows the identification of ApoA-I by Western blot analysis.

Figure 44:
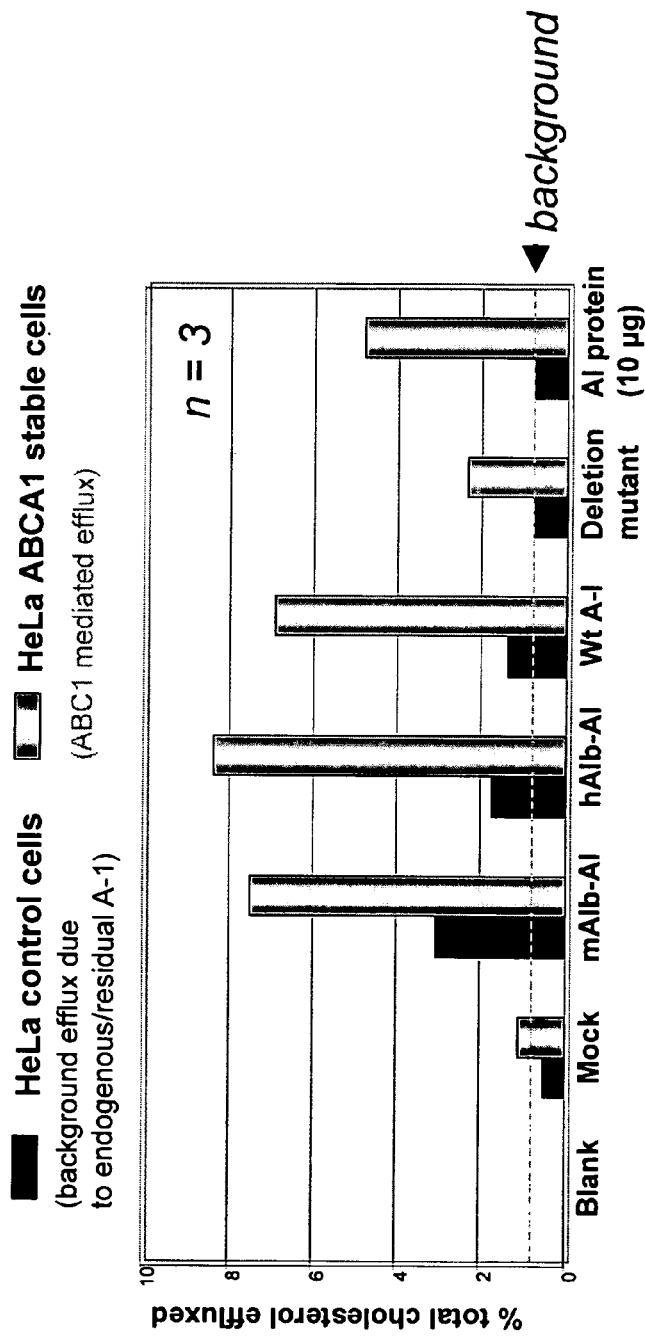

FIG. 44 shows the functionality of ApoA-I as determined by cholesterol efflux assays.

Figure 45:
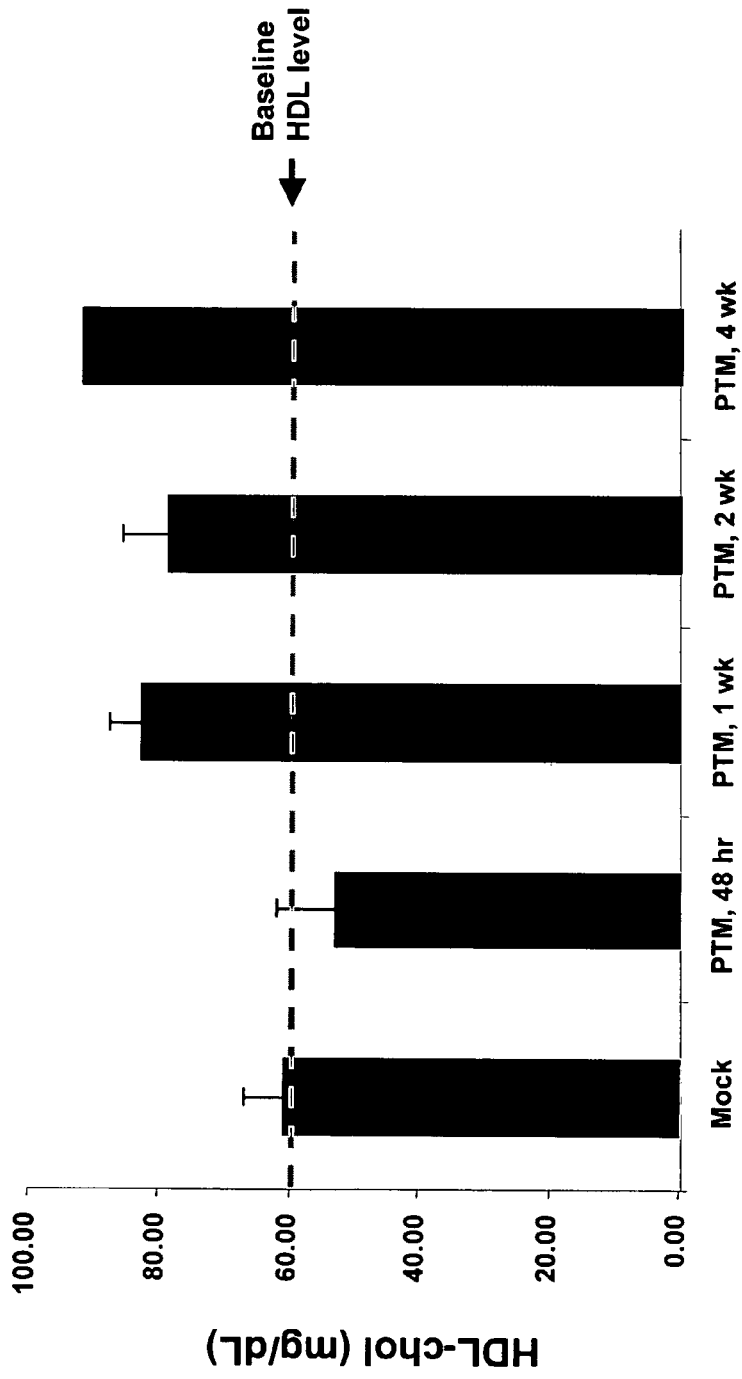

FIG. 45 demonstrates the use of plasmid-based delivery system for long-term production of human HDL in mice.

Figure 46:
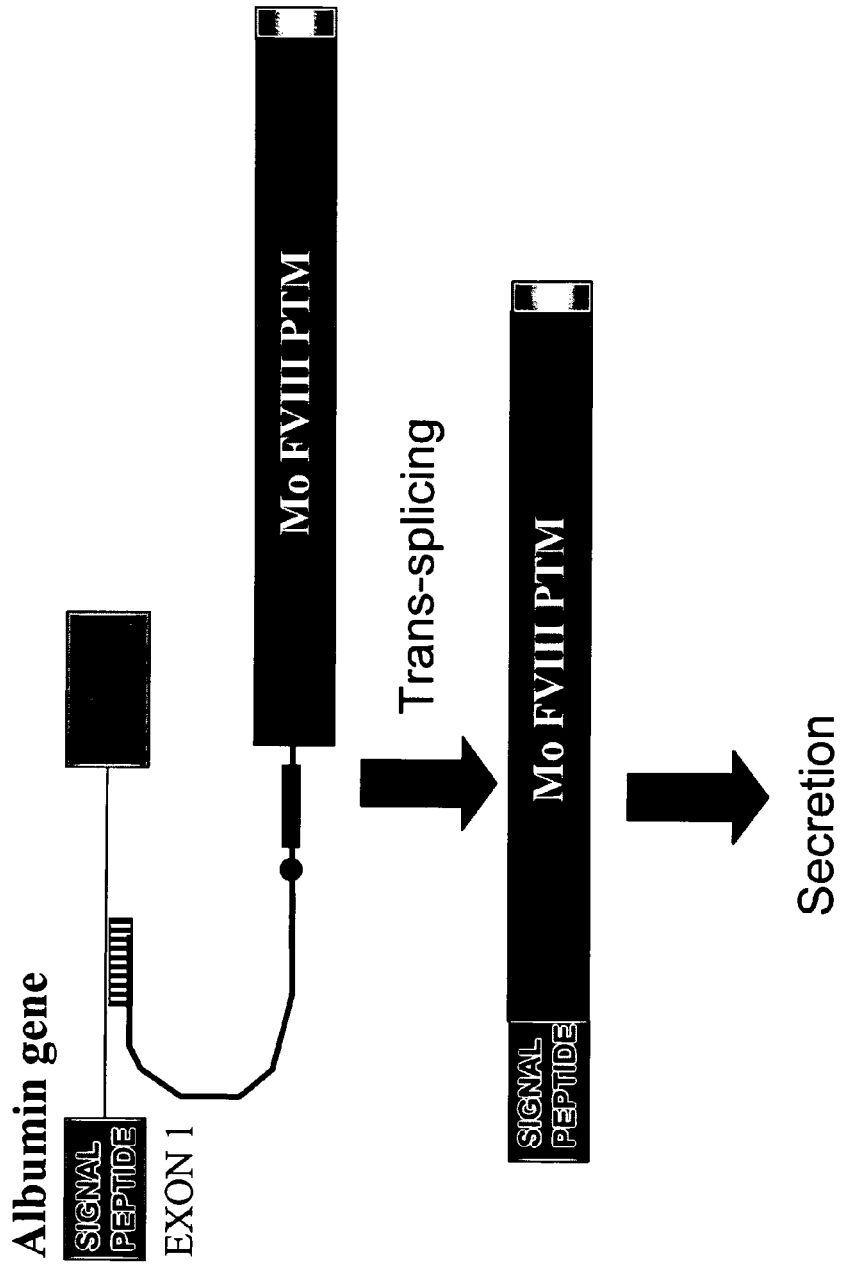

FIG. 46 shows the generation of secreted FVIII through trans-splicing to exon 1 of albumin.

Figure 47:
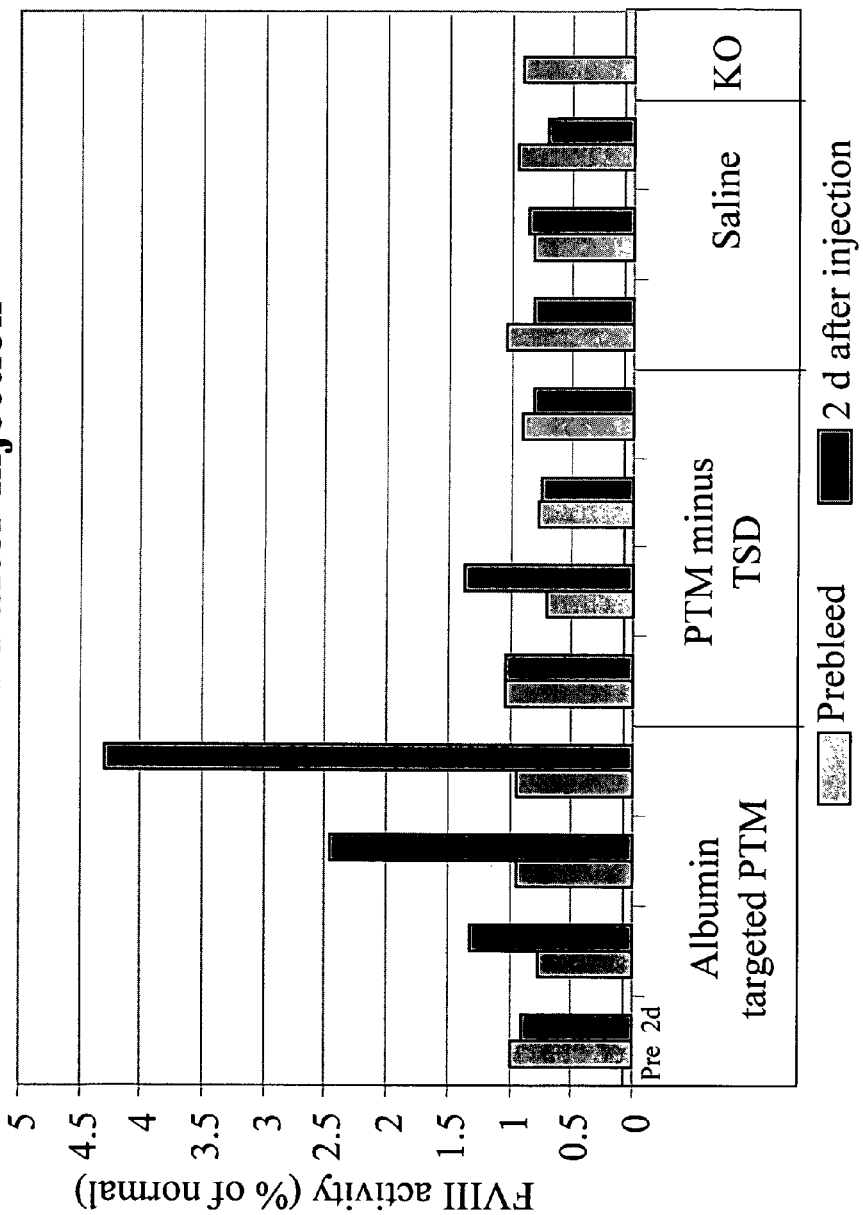

FIG. 47 shows that uninoculated controls as well as animals that received a PTM that were defective in splicing showed no Factor VIII.

Figure 48:
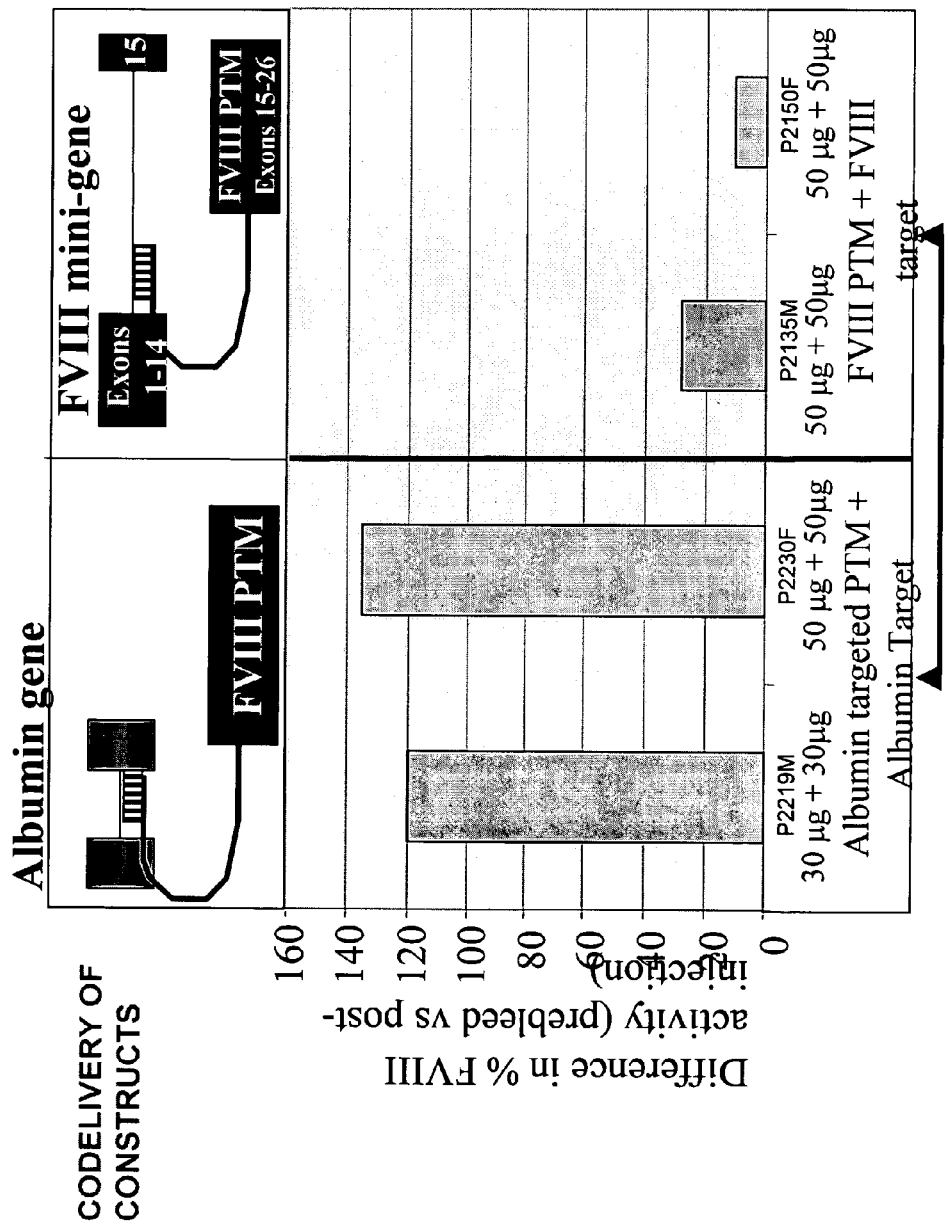

FIG. 48 shows that animals inoculated with both albumin minigene target and the PTM encoding Factor VIII demonstrated significant plasma levels of Factor VIII.

FIG. 49 shows the utilization of a single chain monoclonal antibody directed against E7 of human papillomavirus (HPV).

FIG. 50 demonstrates that in vivo trans-spliced product was effective in inhibiting the growth of HPV-infected cells.

FIG. 51 demonstrates the validity of trans-splicing into a highly abundant transcript.

FIG. 52 shows that the PTM encoding the single chain monoclonal antibody trans-splices specifically into the precise nucleotide sequence in mouse albumin pre-mRNA.

Figure 53:
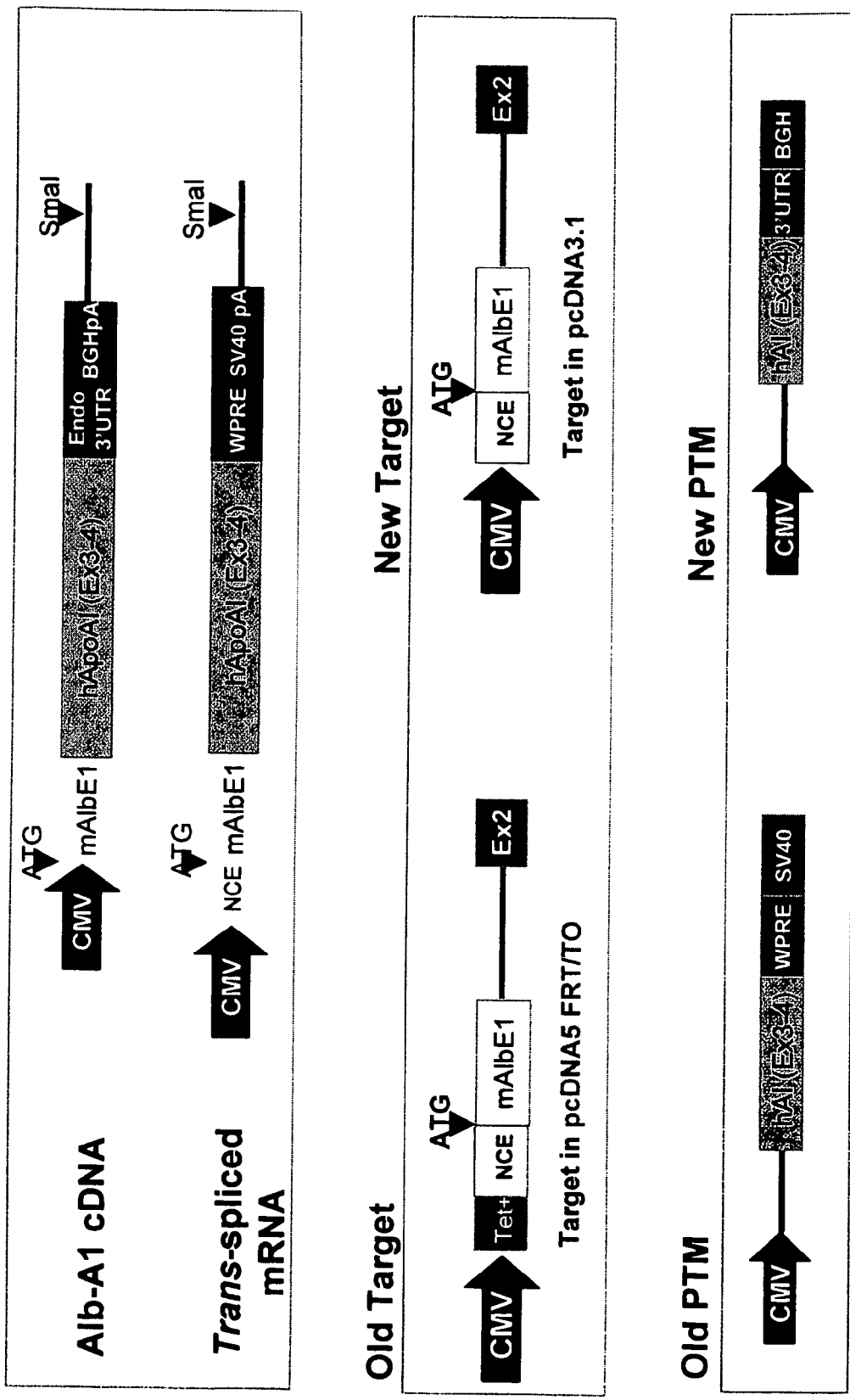

FIG. 53 Schematic drawings of mouse albumin-human apoAI (mAlb-hapoAI) cDNA, trans-spliced mRNA, old and new PTM and targets. NCE, non-coding exon; hAI, human apoAI and Ex, exon.

Figure 54:
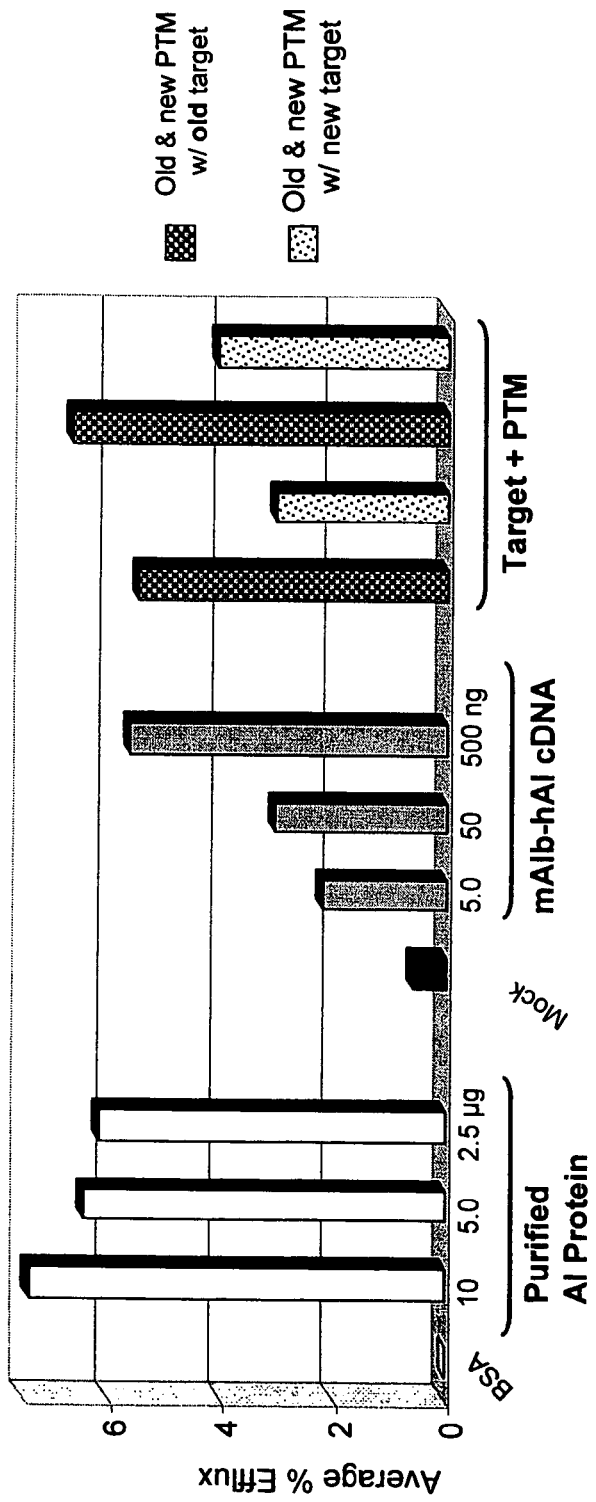

FIG. 54 Trans-splicing between target and PTM plasmids produces functional protein in 293 cells. 293 cells transfected with different concentrations of mAlb-hapoAI cDNA or PTM+target plasmids. 48 hrs post-transfection, media was collected, processed and assayed (efflux potential) for activity as described before.

Figure 55:
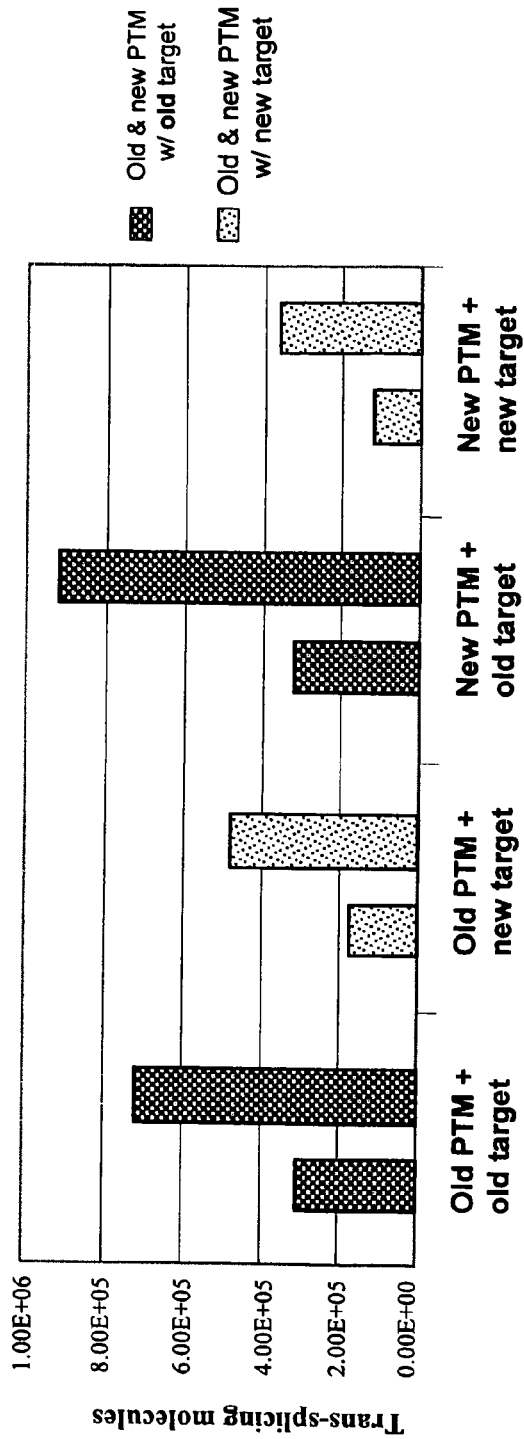

FIG. 55 Trans-splicing efficiency of the new and old PTMs in 293 cells. 293 cells transfected with different concentrations of PTM+target plasmids. 48 hrs post-transfection, total RNA isolated and trans-splicing efficiency was quantified by qRT-PCR using specific primers.

FIG. 56A RT-PCR results showing the presence of mouse mAlb-hapoAI mRNA

FIG. 56B RT-PCR results showing the presence of trans-spliced mRNA in mice.

FIG. 56C RT-PCR results showing trans-splicing of human apoAI PTM into endogenous mouse albumin pre-mRNA in mice. MC, minicircles, PL, plasmid DNA; RT, reverse transcription and +/− indicate RT+ and RT− reactions.

Figure 57A:
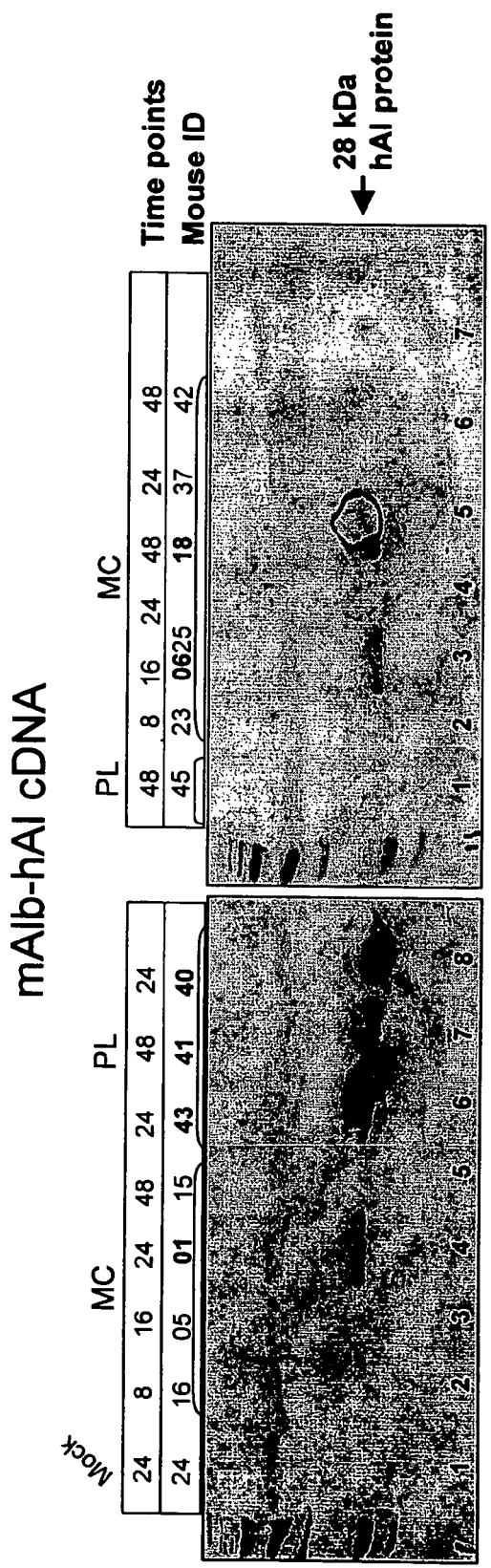

FIG. 57A Western blot analysis of serum samples from mice injected with mAlb-hapoAI cDNA. 20 µl serum passed through Proto-Blue column (to deplete albumin+IgG) and analyzed by Western blot using human apoAI specific antibody. MC, minicircles and PL, plasmid DNA RT.

Figure 57B:
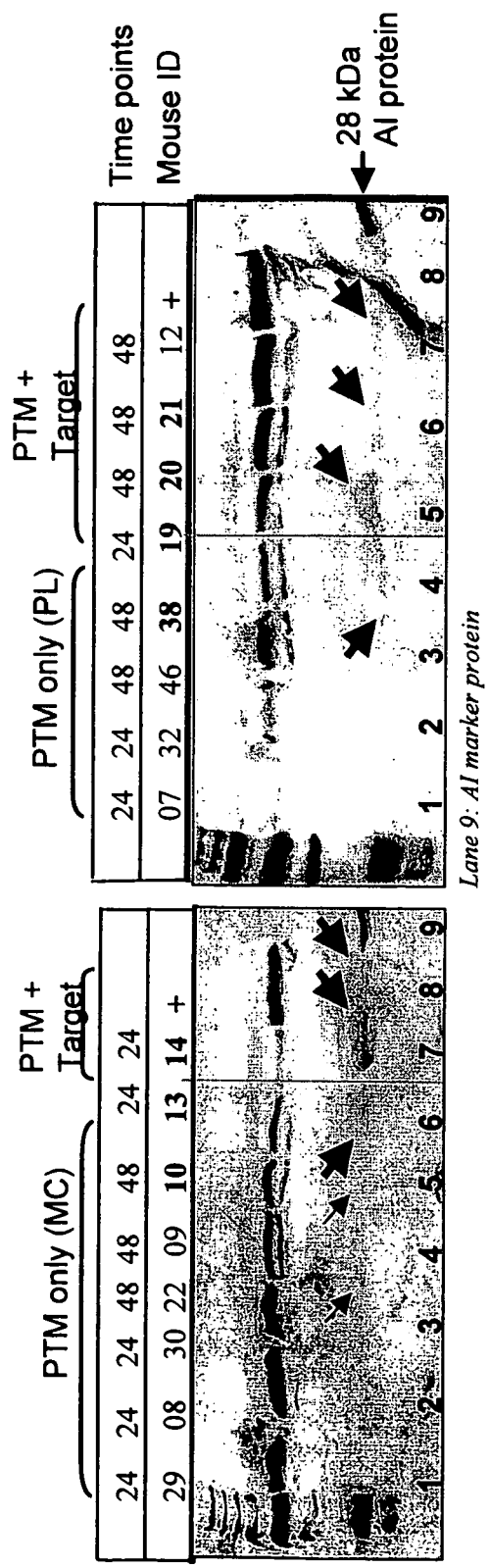

FIG. 57B Western blot analysis of serum samples from mice injected with PTM only and PTM+Target plasmids. 20-50 µl serum passed through Proto-Blue column (to deplete albumin+IgG) and analyzed by Western blot using human apoAI specific antibody. MC, minicircles and PL, plasmid DNA.

Figure 58A:
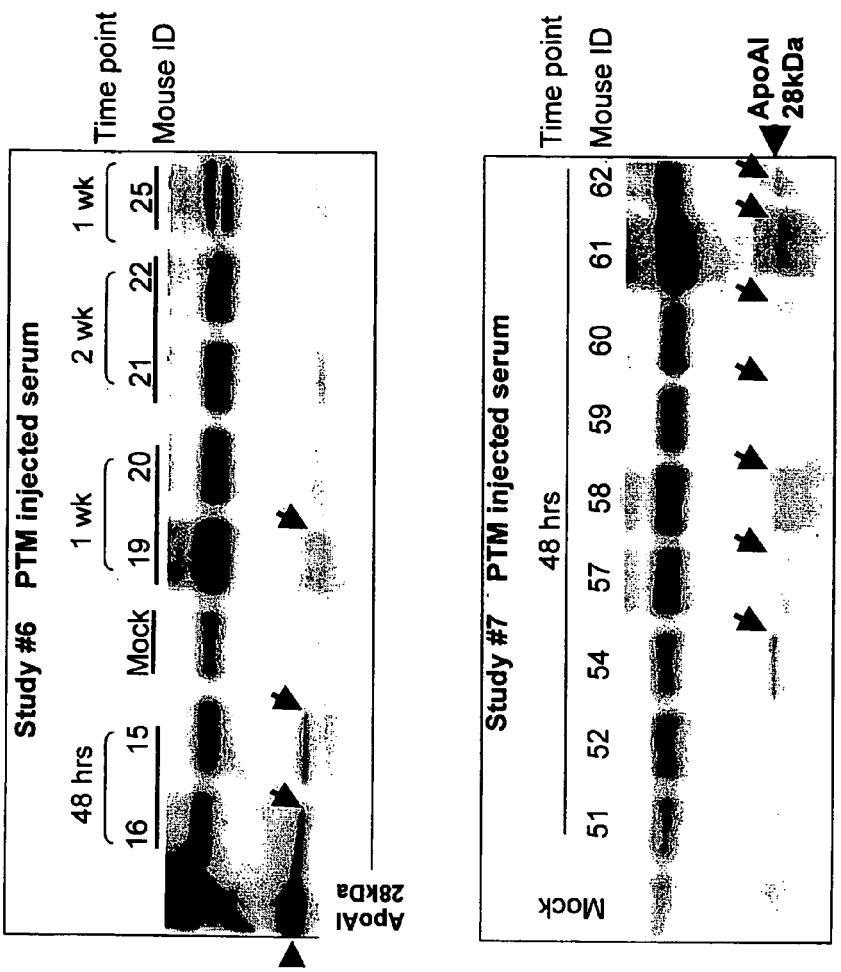

FIG. 58A Western blot analysis of serum samples from mice injected with PTM plasmid. 50 µl serum was immunoprecipitated and analyzed by Western blot using human apoAI specific antibody. Arrows indicate 28 kDa human apoAI protein.

Figure 58B:
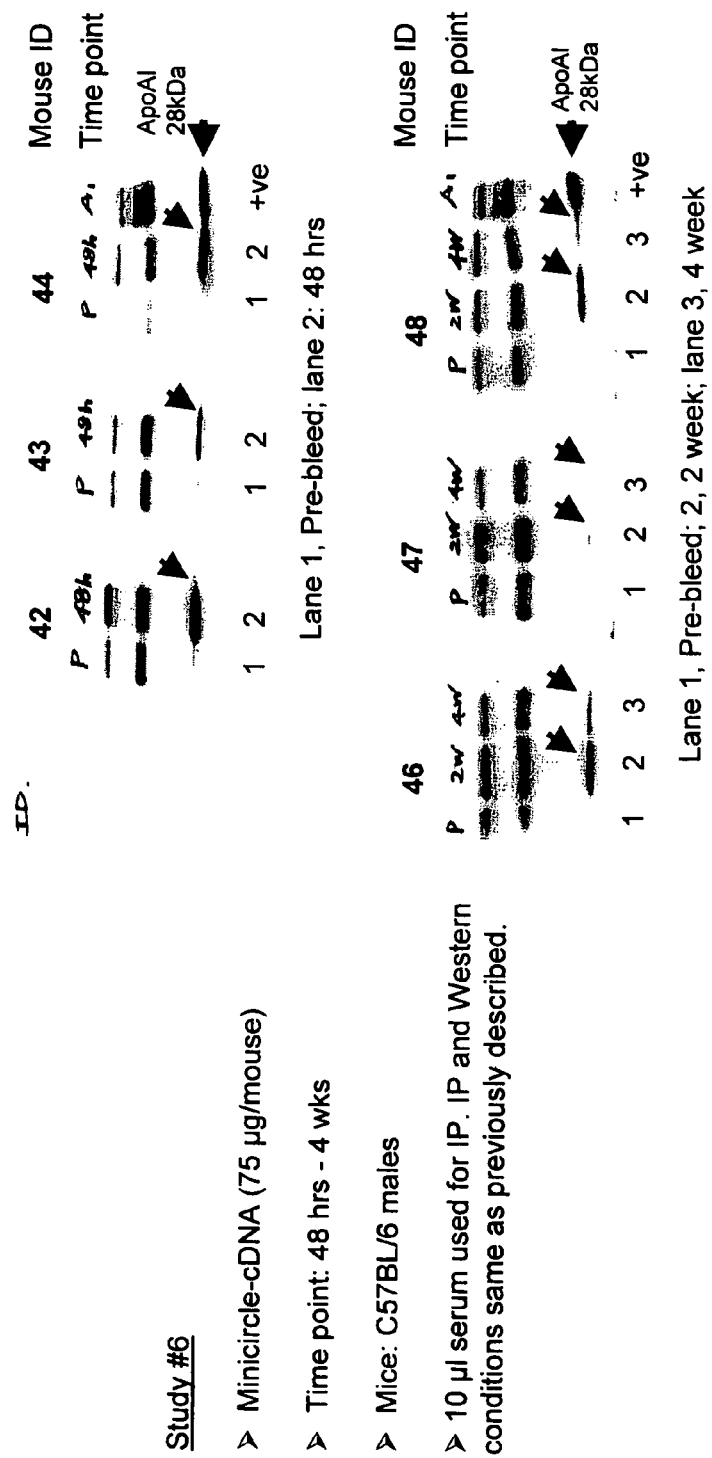

FIG. 58B Western blot analysis of serum samples from mice injected with cDNA plasmid. 10 µl serum was immunoprecipitated and analyzed by Western blot using human apoAI specific antibody.

FIG. 59 HDL analysis of serum samples from mice injected with PTM and mAlb-hapoAI cDNA plasmids.

DETAILED DESCRIPTION OF THE INVENTION

The present invention relates to novel compositions comprising pre-trans-splicing molecules (PTMs), designed for spliceosome mediated trans-splicing, and the use of such molecules for generating a novel chimeric RNA molecule comprising sequences encoding a protein or polypeptide of interest. The PTMs are used for large-scale production of the protein or polypeptide of interest. The methods of the present invention provide for the large-scale production of protein or polypeptide of interest that may be of therapeutic, diagnostic or industrial importance. In additional embodiments, the present invention may be used to produce a protein or polypeptide of interest in vitro, for example by producing the chimeric RNA and translating it in cell culture.

Figure 1:
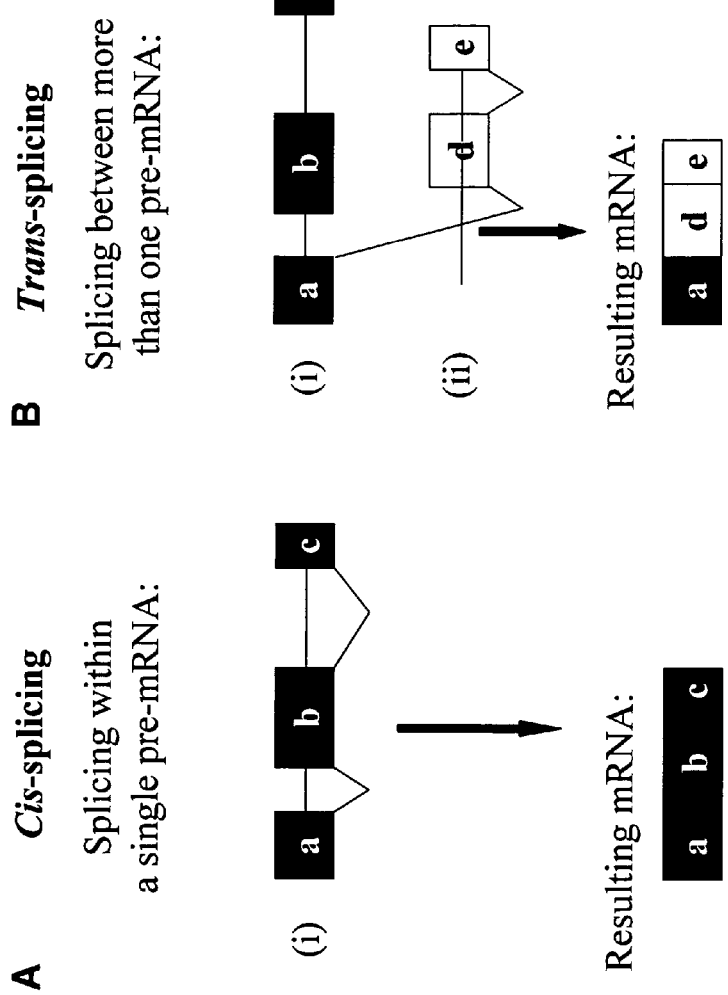
FIG. 1 shows a schematic representation of cis versus trans-splicing reactions.
Figure 2:
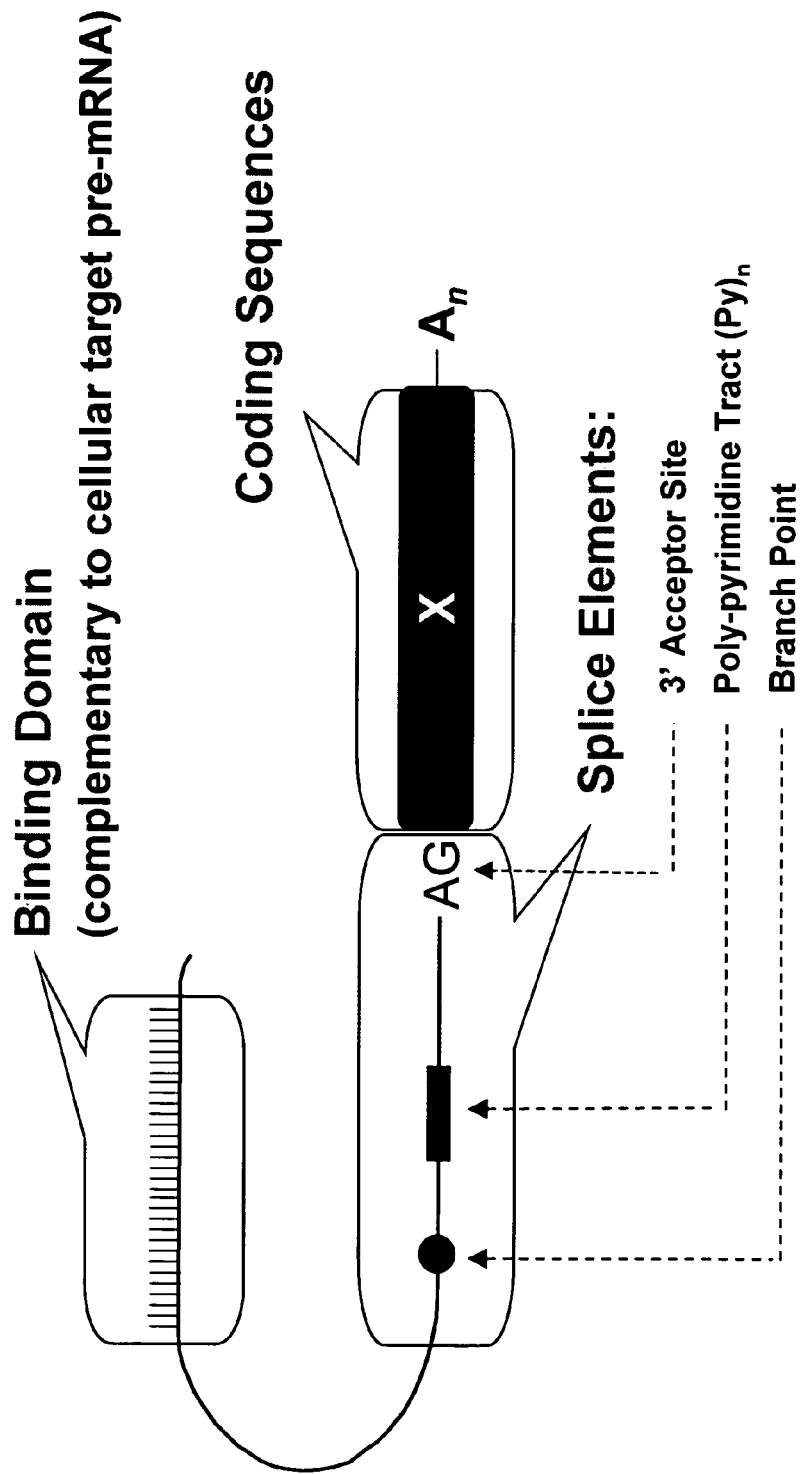
FIG. 2 shows a schematic representation of pre-trans-splicing molecules (PTMs).

The PTMs of the invention, for use in spliceosome mediated trans-splicing, comprise (i) one or more target binding domains that are designed to specifically bind to target pre-mRNA, (ii) a 3' splice region that includes a 3' splice acceptor site and/or a 5' splice donor site; and (iii) nucleotide sequences encoding a protein or polypeptide of interest. The PTM may further comprise a branchpoint, a pyrimidine tract and one or more spacer regions that separate the splice sites from the target-binding domain. (See FIG. 2)

Figure 3:
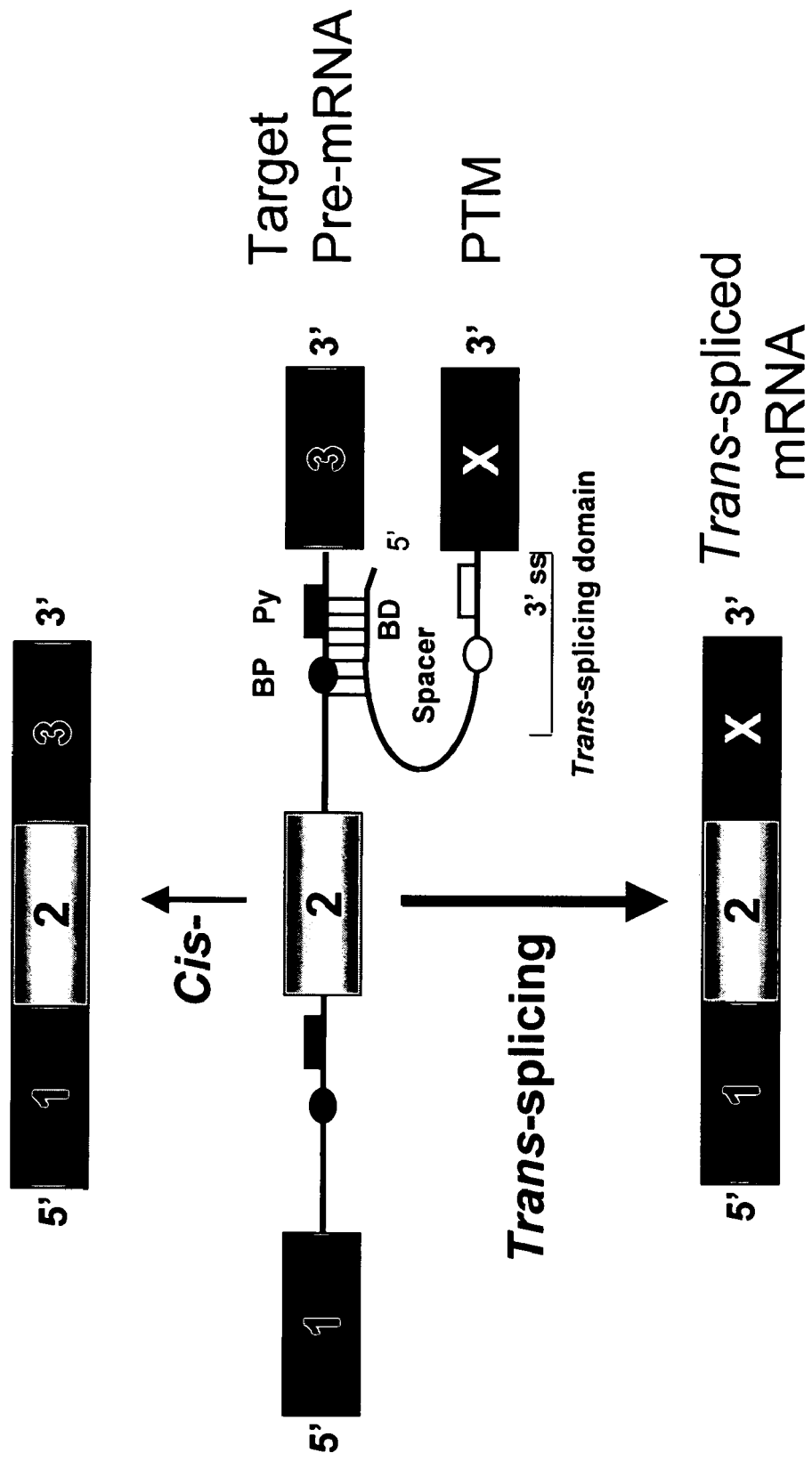
FIG. 3 shows a schematic representation of a trans-splicing reaction between the target 5' splice site and PTM's 3' splice site and 3' exon replacement.

The methods of the invention encompass contacting the PTMs of the invention with an abundantly expressed target pre-mRNA, under conditions in which a portion of the PTM is trans-spliced to a portion of the target pre-mRNA to form a novel chimeric RNA molecule comprising sequences encoding the protein or polypeptide of interest. (See FIG. 3)

As an abundantly expressed pre-mRNA, the RNA encoding albumin may be selected as the primary target, because it is a highly expressed pre-mRNA. However, other transcripts that are also expressed in high abundance could also be selected, such as, but not limited to, casein transcripts in breast tissue that are abundantly expressed in milk in humans and other animals. Additional abundantly expressed transcripts include those coding for myosin (in muscle cells) and fibroin.

Figure 4:
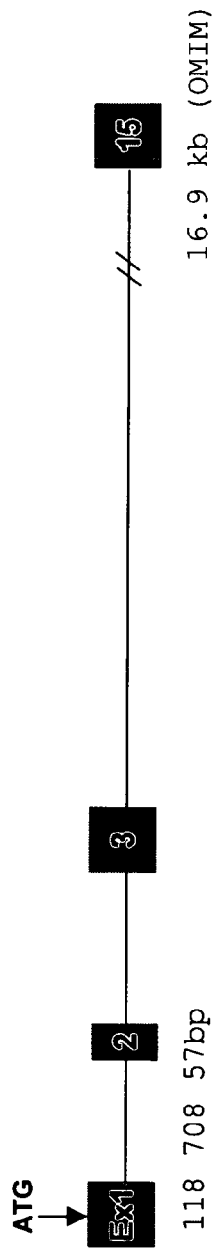
FIG. 4 shows the rationale for selecting albumin transcripts as the target pre-mRNA.

Albumin pre-mRNA may be chosen, because serum concentration of albumin is sufficiently high, i.e. in the range of between 45-50 mg/ml. (See FIG. 4). For example, Trans-splicing antibody sequences into albumin pre-mRNA will result in high concentrations of expressed immunoglobulin molecules into the blood. Even a moderate 5% conversion of albumin pre-mRNA target will result in the production of significantly high antibody concentration, i.e., therapeutic concentration in the blood.

The invention provides for methods of large scale bulk productions of a protein or polypeptide of interest comprising administering to a mammal the PTMs of the present invention, contacting the PTM with the target pre-mRNA under conditions in which a portion of the PTM is trans-spliced to a portion of the abundantly expressed target pre-mRNA to form a chimeric RNA molecule that expresses the protein or polypeptide of interest, collecting the bodily fluid from the mammal, and treating the fluid to obtain the protein or polypeptide of interest.

Structure of the Pre-Trans-Splicing Molecules

The present invention provides compositions for use in generating novel chimeric nucleic acid molecules through targeted trans-splicing. The PTMs of the invention comprise (i) one or more target binding domains that targets binding of the PTM to target pre-mRNA (ii) a 3' splice region that includes a 3' splice acceptor site and/or 5' splice donor site; and (iii) nucleotide sequences encoding a protein or polypeptide of interest.

The PTMs of the invention may also include at least one of the following features: (a) binding domains targeted to intron sequences in close proximity to the 3' or 5' splice signals of the target intron, (b) mini introns, and (c) ISAR (intronic splicing activator and repressor) consensus binding sites. The PTMs of the invention may further comprise one or more spacer regions to separate the RNA splice site from the target binding domain.

The general design, construction and genetic engineering of PTMs and demonstration of their ability to successful mediate spliceosome mediated trans-splicing reactions within the cell are described in detail in U.S. Pat. Nos. 6,083,702, 6,013,487 and 6,280,978, as well as U.S. patent application Ser. Nos. 09/756,095, 09/756,096, 09/756,097, 09/838,858, 10/076,248 and 09/941,492, the disclosures of which are incorporated by reference in their entireties herein.

The target binding domain of the PTM endows the PTM with a binding affinity for a target pre-mRNA. As used herein, a target binding domain is defined as any molecule, i.e., nucleotide, protein, chemical compound, etc., that confers specificity of binding and anchors the target pre-mRNA closely in space to the PTM so that the spliceosome processing machinery of the nucleus can trans-splice a portion of the synthetic PTM to a portion of the albumin pre-mRNA.

The target binding domain of the PTM may contain multiple binding domains that are complementary to and in anti-sense orientation to the targeted region of target pre-mRNA. The target binding domains may comprise up to several thousand nucleotides. In preferred embodiments of the invention the binding domains may comprise at least 10 to 30 and up to several hundred or more nucleotides. The specificity of the PTM may be increased significantly by increasing the length of the target binding domain. For example, the target binding domain may comprise several hundred nucleotides or more. Absolute complementarity, although preferred, is not required. A sequence "complementary" to a portion of an RNA, as referred to herein, means a sequence having sufficient complementarity to be able to hybridize with the target pre-mRNA, forming a stable duplex. The ability to hybridize will depend on both the degree of complementarity and the length of the nucleic acid (See, for example, Sambrook et al., 1989, Molecular Cloning, A Laboratory Manual, 2d Ed., Cold Spring Harbor Laboratory Press, Cold Spring Harbor, N.Y.). Generally, the longer the hybridizing nucleic acid, the more base mismatches with an RNA it may contain and still form a stable duplex. One skilled in the art can ascertain a tolerable degree of mismatch or length of duplex by use of standard procedures to determine the stability of the hybridized complex.

In a specific embodiment, the binding domain of the PTM targets specific sequences in the target pre-mRNA so as to reduce the number of sequences derived from the target pre-mRNA. For example, targeting intron sequences of the target pre-mRNA minimizes the number of sequences derived from the target pre-mRNA in the chimeric RNA molecule.

Binding may also be achieved through other mechanisms, for example, through triple helix formation, aptamer interactions, antibody interactions or protein/nucleic acid interactions such as those in which the PTM is engineered to recognize a specific RNA binding protein, i.e., a protein bound to a specific target pre-mRNA.

The abundantly expressed target pre-mRNA according to the present invention may be any abundant transcript. (See, e.g., FIG. 5) Preferably, the target pre-mRNA is an albumin or casein pre-mRNA. However, the target could similarly be an abundant transcript in plants, such as chlorophyll II binding protein.

Figure 6:
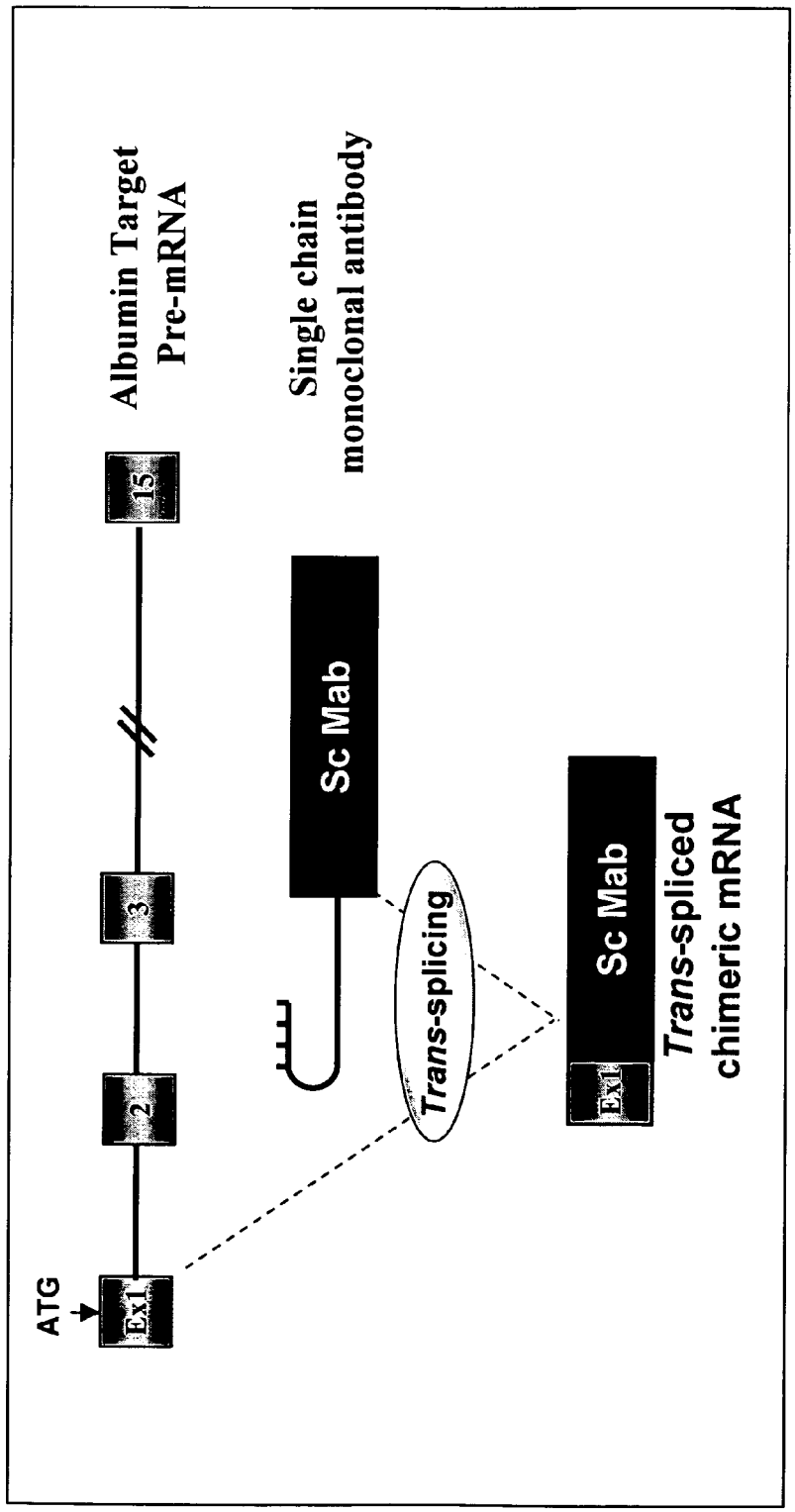
FIG. 6 shows trans-splicing into the albumin target pre-mRNA.

In a specific embodiment of the invention, the target binding domain is complementary and in anti-sense orientation to sequences of the apoA-1, apoB, or albumin target pre-mRNA, which hold the PTM in close proximity to the target for trans-splicing. For example, a target binding domain may be defined as any molecule, i.e., nucleotide, protein, chemical compound, etc., that confers specificity of binding and anchors the apoA-1, or apoB or albumin pre-mRNA closely in space to the PTM so that the spliceosome processing machinery of the nucleus can trans-splice a portion of the PTM to a portion of the apoA-1, or apoB, or albumin pre-mRNA. (See, e.g., FIG. 6).

In another specific embodiment of the invention, the target binding domain is complementary and in anti-sense orientation to sequences of the alpha (s1) casein, alpha (s2) casein, beta casein or kappa casein target pre-mRNA, which hold the PTM in close proximity to the target for trans-splicing. For example, a target binding domain may be defined as any molecule, i.e., nucleotide, protein, chemical compound, etc., that confers specificity of binding and anchors the alpha (s1) casein, alpha (s2) casein, beta casein or kappa casein target pre-mRNA closely in space to the PTM so that the spliceosome processing machinery of the nucleus can trans-splice a portion of the PTM to a portion of the alpha (s1) casein, alpha (s2) casein, beta casein or kappa casein target pre-mRNA.

The PTM molecule also contains a 3' splice region that includes a 3' splice acceptor AG site and/or a 5' splice donor site. The 3' splice region may further comprise a branchpoint and a polypyrimidine tract. Consensus sequences for the 5' splice donor site and the 3' splice region used in RNA splicing are well known in the art (See, Moore, et al., 1993, The RNA World, Cold Spring Harbor Laboratory Press, p. 303-358). In addition, modified consensus sequences that maintain the ability to function as 5' donor splice sites and 3' splice regions may be used in the practice of the invention. Briefly, the 5' splice site consensus sequence is AG/GURAGU (where A=adenosine, U=uracil, G=guanine, C=cytosine, R=purine and /=the splice site) (SEQ ID NO.:1). The 3' splice site consists of three separate sequence elements: the branchpoint or branch site, a polypyrimidine tract and the 3' consensus sequence (YAG). The branch point consensus sequence in mammals is YNYUR<u>A</u>C (Y=pyrimidine; N=any nucleotide) (SEQ ID NO.:2). The underlined A is the site of branch formation. A polypyrimidine tract is located between the branch point and the splice site acceptor and is important for different branch point utilization and 3' splice site recognition. Recently, pre-mRNA introns beginning with the dinucleotide AU and ending with the dinucleotide AC have been identified and referred to as U12 introns. U12 intron sequences, as well as any sequences that function as splice acceptor/donor sequences, may also be used to generate the PTMs of the invention.

One or more spacer region(s) to separate the RNA splice site from the target binding domain may also be included in the PTM. The spacer region may be designed to include features, such as (i) stop codons which would function to block translation of any unspliced PTM and/or (ii) sequences that enhance trans-splicing to the target pre-mRNA.

A nucleotide sequence encoding a protein or polypeptide of interest is also included in the PTM of the invention. The PTMs of the invention may contain exon sequences which when trans-spliced to the target pre-mRNA will result in the formation of a chimeric RNA capable of encoding a functional protein or polypeptide of interest. The PTM may be engineered to contain the exon sequences of various recombinant proteins or polypeptides. The proteins or polypeptides of interest may be selected from the group consisting of cytokines, growth factors, such as epogen, insulin, human growth factor, hormones, enzymes and antibody polypeptides. In addition, the encoded protein or polypeptide of interest may be a therapeutic protein that is expensive to produce commercially, such as ApoA1 or ApoA1 milano variant.

Figure 7:
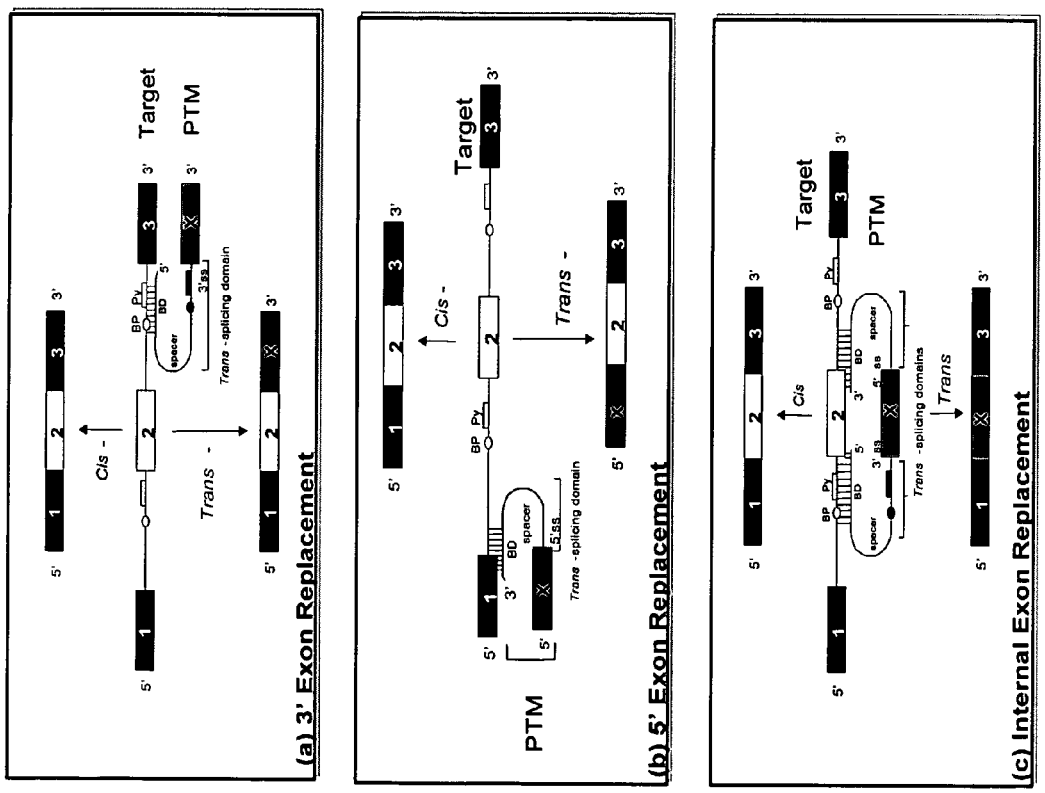
FIG. 7 shows a schematic representation of different trans-splicing reactions. (a) trans-splicing reactions between the target 5' splice site and PTM's 3' splice site, (b) trans-splicing reactions between the target 3' splice site and PTM's 5' splice site and (c) replacement of an internal exon by a double trans-splicing reaction in which the PTM carries both 3' and 5' splice sites. BD, binding domain; BP, branch point sequence; PPT, polypyrimidine tract; and ss, splice sites.

The PTM's of the invention may be engineered to contain a single exon sequence, multiple exon sequences, or alternatively the complete set of exon sequences encoding the antigen of interest. The number and identity of the sequences to be used in the PTMs will depend on the type of trans-splicing reaction, i.e., 5' exon replacement, 3' exon replacement or internal exon replacement that will occur (See FIG. 7).

In an embodiment of the invention, a "safety" is also incorporated into the spacer, binding domain, or elsewhere in the PTM to prevent non-specific trans-splicing. This is a region of the PTM that covers elements of the 3' and/or 5' splice site of the PTM by relatively weak complementarity, preventing non-specific trans-splicing. The PTM is designed in such a way that upon hybridization of the binding/targeting portion(s) of the PTM, the 3' and/or 5' splice site is uncovered and becomes fully active.

Such "safety" sequences comprises one or more complementary stretches of cis-sequence (or could be a second, separate, strand of nucleic acid) which binds to one or both sides of the PTM branch point, pyrimidine tract, 3' splice site and/or 5' splice site (splicing elements), or could bind to parts of the splicing elements themselves. This "safety" binding prevents the splicing elements from being active (i.e. block U2 snRNP or other splicing factors from attaching to the PTM splice site recognition elements). The binding of the "safety" may be disrupted by the binding of the target binding region of the PTM to target pre-mRNA, thus exposing and activating the PTM splicing elements (making them available to trans-splice into target pre-mRNA).

A nucleotide sequence capable of forming a stem-loop structure may also be included in the PTM of the invention.

The present invention further provides PTM molecules wherein the coding region of the PTM is engineered to contain mini-introns. The insertion of mini-introns into the coding sequence of the PTM is designed to increase definition of the exon and enhance recognition of the PTM donor site. Mini-intron sequences to be inserted into the coding regions of the PTM include small naturally occurring introns or, alternatively, any intron sequences, including synthetic mini-introns, which include 5' consensus donor sites and 3' consensus sequences which include a branch point, a 3' splice site and in some instances a pyrimidine tract.

The mini-intron sequences are preferably between about 60-150 nucleotides in length, however, mini-intron sequences of increased lengths may also be used. In a preferred embodiment of the invention, the mini-intron comprises the 5' and 3' end of an endogenous intron. In preferred embodiments of the invention the 5' intron fragment is about 20 nucleotides in length and the 3' end is about 40 nucleotides in length.

In a specific embodiment of the invention, an intron of 528 nucleotides comprising the following sequences may be utilized. Sequence of the intron construct is as follows:

```
5' fragment sequence: (SEQ ID NO: 3)
Gtagttcttttgttcttcactattaagaacttaatttggtgtccatgtct
ctttttttttctagtttgtagtgctggaaggtattttggagaaattctt
acatgagcattaggagaatgtatgggtgtagtgtcttgtataatagaaat
tgttccactgataatttactctagttttttcctcatattattttcagtgg
cttttcttccacatctttatattttgcaccacattcaacactgtagcgg
ccgc.

3' fragment sequence: (SEQ ID NO: 4)
Ccaactatctgaatcatgtgccccttctctgtgaacctctatcataatac
ttgtcacactgtattgtaattgtctcttttacttccccttgtatcttttg
tgcatagcagagtacctgaaacaggaagtattttaaatattttgaatcaa
atgagttaatagaatctttacaaataagaatatacacttctgcttaggat
gataattggaggcaagtgaatcctgagcgtgatttgataatgacctaata
atgatgggtttatttccag
```

In yet another specific embodiment of the invention, consensus ISAR sequences are included in the PTMs of the invention (Jones et al., NAR 29:3557-3565). Proteins bind to the ISAR splicing activator and repressor consensus sequence which includes a uridine-rich region that is required for 5' splice site recognition by U1 SnRNP. The 18 nucleotide ISAR consensus sequence comprises the following sequence: GGGCUGAUUUUUCCAUGU (SEQ ID NO:5). When inserted into the PTMs of the invention, the ISAR consensus sequences are inserted into the structure of the PTM in close proximity to the 5' donor site of intron sequences. In an embodiment of the invention the ISAR sequences are inserted within 100 nucleotides from the 5' donor site. In a preferred embodiment of the invention, the ISAR sequences are inserted within 50 nucleotides from the 5' donor site. In a more preferred embodiment of the invention the ISAR sequences are inserted within 20 nucleotides of the 5' donor site.

The compositions of the invention further comprise PTMs that have been engineered to include cis-acting ribozyme sequences. The inclusion of such sequences is designed to reduce PTM translation in the absence of trans-splicing or to produce a PTM with a specific length or defined end(s). The ribozyme sequences that may be inserted into the PTMs include any sequences that are capable of mediating a cis-acting (self-cleaving) RNA splicing reaction. Such ribozymes include but are not limited to hammerhead, hairpin and hepatitis delta virus ribozymes (see, Chow et al. 1994, *J Biol Chem* 269:25856-64).

In an embodiment of the invention, splicing enhancers such as, for example, sequences referred to as exonic splicing enhancers may also be included in the structure of the synthetic PTMs. Transacting splicing factors, namely the serine/arginine-rich (SR) proteins, have been shown to interact with such exonic splicing enhancers and modulate splicing (See, Tacke et al., 1999, *Curr. Opin. Cell Biol.* 11:358-362; Tian et al., 2001, *J. Biological Chemistry* 276:33833-33839; Fu, 1995, RNA 1:663-680). Nuclear localization signals may also be included in the PTM molecule (Dingwell and Laskey, 1986, *Ann. Rev. Cell Biol.* 2:367-390; Dingwell and Laskey, 1991, *Trends in Biochem. Sci.* 16:478-481). Such nuclear localization signals can be used to enhance the transport of synthetic PTMs into the nucleus where trans-splicing occurs.

Additional features can be added to the PTM molecule, such as polyadenylation signals to modify RNA expression/stability, or 5' splice sequences to enhance splicing, additional binding regions, "safety"-self complementary regions, additional splice sites, or protective groups to modulate the stability of the molecule and prevent degradation. Stop codons may be included in the PTM structure to prevent translation of unspliced PTMs. Elements, such as a 3' hairpin structure, circularized RNA, nucleotide base modification, or synthetic analogs, can be incorporated into PTMs to promote or facilitate nuclear localization and spliceosomal incorporation, and intracellular stability.

To facilitate collection of the protein or polypeptide of interest that is produced as a result of trans-splicing, sequence tags may be incorporated into the PTMs. The tags promote affinity purification of the expressed protein or polypeptide of interest product of the chimeric RNA molecule.

The PTMs may be further engineered to incorporate cleavage sites to facilitate isolation of the mature biologically active protein or polypeptide of interest from the expressed protein product of the chimeric RNA molecule.

Secretory signaling sequences could be incorporated to increase secretion of the expressed protein or polypeptide of interest.

In addition to the PTM molecules described above, which are designed for spliceosome-mediated trans-splicing reactions, nucleic acid molecules may also be designed for ribozyme-mediated (group I and group II) or tRNA endonuclease mediated trans-splicing reactions.

When specific PTMs are to be synthesized in vitro (synthetic PTMs), such PTMs can be modified at the base moiety, sugar moiety, or phosphate backbone, for example, to improve stability of the molecule, hybridization to the target mRNA, transport into the cell, etc. For example, modification of a PTM to reduce the overall charge can enhance the cellular uptake of the molecule. In addition, modifications can be made to reduce susceptibility to nuclease or chemical degradation. The nucleic acid molecules may be synthesized in such a way as to be conjugated to another molecule such as a peptides (e.g., for targeting host cell receptors in vivo), or an agent facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci.* 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, *BioTechniques* 6:958-976) or intercalating agents (see, e.g., Zon, 1988, *Pharm. Res.* 5:539-549). To this end, the nucleic acid molecules may be conjugated to another molecule, e.g., a peptide, hybridization triggered cross-linking agent, transport agent, hybridization-triggered cleavage agent, etc.

It may be necessary in certain cases to cleave amino acids originating from albumin to obtain the purified biologically active protein of interest. This can be achieved by standard methods such as engineering a protease site in the junction between portions originating from albumin and the recombinant protein of interest. One example is the TEV protease. Another method is to tag peptides with, for example, calmodulin binding domain. These methods have been widely used to obtain only those amino acids in the protein of interest and no amino acids derived from albumin or other target.

Various other well-known modifications to the nucleic acid molecules can be introduced as a means of increasing intracellular stability and half-life. Possible modifications include, but are not limited to, the addition of flanking sequences of ribonucleotides to the 5' and/or 3' ends of the molecule. In some circumstances where increased stability is desired, nucleic acids having modified internucleoside linkages such as 2'-0-methylation may be preferred. Nucleic acids containing modified internucleoside linkages may be synthesized using reagents and methods that are well known in the art (see, Uhlmann et al., 1990, *Chem. Rev.* 90:543-584; Schneider et al., 1990, *Tetrahedron Lett.* 31:335 and references cited therein).

The PTMs of the present invention are preferably modified in such a way as to increase their stability in the cells. Since RNA molecules are sensitive to cleavage by cellular ribonucleases, it may be preferable to use as the competitive inhibitor a chemically modified oligonucleotide (or combination of oligonucleotides) that mimics the action of the RNA binding sequence but is less sensitive to nuclease cleavage. In addition, the synthetic PTMs can be produced as nuclease resistant circular molecules with enhanced stability to prevent degradation by nucleases (Puttaraju et al., 1995, *Nucleic Acids Symposium Series No.* 33:49-51; Puttaraju et al., 1993, *Nucleic Acid Research* 21:4253-4258). Other modifications may also be required, for example to enhance binding, to enhance cellular uptake, to improve kinetics or to improve other desirable characteristics.

Modifications, which may be made to the structure of the synthetic PTMs include but are not limited to backbone modifications such as use of:

(i) phosphorothioates (X or Y or W or Z=S or any combination of two or more with the remainder as O). e.g. Y=S (Stein, C. A., et al., 1988, *Nucleic Acids Res.*, 16:3209-3221), X=S (Cosstick, R., et al., 1989, *Tetrahedron Letters*, 30, 4693-4696), Y and Z=S (Brill, W. K.-D., et al., 1989, *J. Amer. Chem. Soc.*, 111:2321-2322); (ii) methylphosphonates (e.g. Z=methyl (Miller, P. S., et al., 1980, *J. Biol. Chem.*, 255:9659-9665); (iii) phosphoramidates (Z=N-(alkyl)$_2$ e.g. alkyl methyl, ethyl, butyl) (Z=morpholine or piperazine) (Agrawal, S., et al., 1988, *Proc. Natl. Acad. Sci. USA* 85:7079-7083) (X or W=NH) (Mag, M., et al., 1988, *Nucleic Acids Res.*, 16:3525-3543); (iv) phosphotriesters (Z=O-alkyl e.g. methyl, ethyl, etc) (Miller, P. S., et al., 1982, *Biochemistry*, 21:5468-5474); and (v) phosphorus-free linkages (e.g. carbamate, acetamidate, acetate) (Gait, M. J., et al., 1974, *J. Chem. Soc. Perkin I*, 1684-1686; Gait, M. J., et al., 1979, *J. Chem. Soc. Perkin I*, 1389-1394).

In addition, sugar modifications may be incorporated into the PTMs of the invention. Such modifications include the use of: (i) 2'-ribonucleosides (R=H); (ii) 2'-O-methylated nucleosides (R=OMe)) (Sproat, B. S., et al., 1989, *Nucleic Acids Res.*, 17:3373-3386); and (iii) 2'-fluoro-2'-riboxynucleosides (R=F) (Krug, A., et al., 1989, *Nucleosides and Nucleotides*, 8:1473-1483).

Further, base modifications that may be made to the PTMs, including but not limited to use of: (i) pyrimidine derivatives substituted in the 5-position (e.g. methyl, bromo, fluoro etc) or replacing a carbonyl group by an amino group (Piccirilli, J. A., et al., 1990, *Nature*, 343:33-37); (ii) purine derivatives lacking specific nitrogen atoms (e.g., 7-deaza adenine, hypoxanthine) or functionalized in the 8-position (e.g., 8-azido adenine, 8-bromo adenine) (for a review see Jones, A. S., 1979, *Int. J. Biolog. Macromolecules*, 1:194-207).

In addition, the PTMs may be covalently linked to reactive functional groups, such as: (i) psoralens (Miller, P. S., et al., 1988, *Nucleic Acids Res.*, Special Pub. No. 20, 113-114), phenanthrolines (Sun, J-S., et al., 1988, *Biochemistry*, 27:6039-6045), mustards (Vlassov, V. V., et al., 1988, *Gene*, 72:313-322) (irreversible cross-linking agents with or without the need for co-reagents); (ii) acridine (intercalating agents) (Helene, C., et al., 1985, *Biochimie*, 67:777-783); (iii) thiol derivatives (reversible disulphide formation with proteins) (Connolly, B. A., and Newman, P. C., 1989, *Nucleic*

*Acids Res.*, 17:4957-4974); (iv) aldehydes (Schiff's base formation); (v) azido, bromo groups (UV cross-linking); or (vi) ellipticines (photolytic cross-linking) (Perrouault, L., et al., 1990, *Nature,* 344:358-360).

In an embodiment of the invention, oligonucleotide mimetics in which the sugar and internucleoside linkage, i.e., the backbone of the nucleotide units, are replaced with novel groups can be used. For example, one such oligonucleotide mimetic which has been shown to bind with a higher affinity to DNA and RNA than natural oligonucleotides is referred to as a peptide nucleic acid (PNA) (for review see, Uhlmann, E. 1998, Biol. Chem. 379:1045-52). Thus, PNA may be incorporated into synthetic PTMs to increase their stability and/or binding affinity for the target pre-mRNA.

In another embodiment of the invention, the PTMs may be covalently linked to lipophilic groups or other reagents capable of improving uptake by cells. For example, the PTM molecules may be covalently linked to: (i) cholesterol (Letsinger, R. L., et al., 1989, *Proc. Natl. Acad. Sci. USA,* 86:6553-6556); (ii) polyamines (Lemaitre, M., et al., 1987, *Proc. Natl. Acad. Sci, USA,* 84:648-652); other soluble polymers (e.g. polyethylene glycol) to improve the efficiently with which the PTMs are delivered to a cell. In addition, combinations of the above identified modifications may be utilized to increase the stability and delivery of PTMs into the target cell. The PTMs of the invention can be used in methods designed to produce a novel chimeric RNA in a target cell.

The methods of the present invention comprise delivering to the target cell a PTM which may be in any form used by one skilled in the art, for example, an RNA molecule, or a DNA vector which is transcribed into a RNA molecule corresponding to the PTM of the present invention, wherein said PTM binds to target pre-mRNA and mediates a trans-splicing reaction resulting in formation of a chimeric mRNA that expresses a protein or polypeptide of interest.

Synthesis of the Trans-Splicing Molecules

The nucleic acid molecules of the invention can be RNA or DNA or derivatives or modified versions thereof, single-stranded or double-stranded. By nucleic acid is meant a PTM molecule, a ribozyme or t-RNA endonuclease based nucleic acid molecule, or a nucleic acid molecule encoding a PTM molecule, a ribozyme or t-RNA endonuclease based nucleic acid molecule, whether composed of deoxyribonucleotides or ribonucleosides, and whether composed of phosphodiester linkages or modified linkages. The term nucleic acid also specifically includes nucleic acids composed of bases other than the five biologically occurring bases (adenine, guanine, thymine, cytosine and uracil). In addition, the PTMs of the invention may comprise, DNA/RNA, RNA/protein or DNA/RNA/protein chimeric molecules that are designed to enhance the stability of the PTMs.

The PTMs of the invention can be prepared by any method known in the art for the synthesis of nucleic acid molecules. For example, the nucleic acids may be chemically synthesized using commercially available reagents and synthesizers by methods that are well known in the art (see, e.g., Gait, 1985, *Oligonucleotide Synthesis. A Practical Approach,* IRL Press, Oxford, England).

Alternatively, synthetic PTMs can be generated by in vitro transcription of DNA sequences encoding the PTM of interest. Such DNA sequences can be incorporated into a wide variety of vectors downstream from suitable RNA polymerase promoters such as the T7, SP6, or T3 polymerase promoters. Consensus RNA polymerase promoter sequences include the following:

| T7: | TAATACGACTCACTATAGGGAGA | (SEQ ID NO: 6) |
|---|---|---|
| SP6: | ATTTAGGTGACACTATAGAAGNG | (SEQ ID NO: 7) |
| T3: | AATTAACCCTCACTAAAGGGAGA. | (SEQ ID NO: 8) |

The base in bold is the first base incorporated into RNA during transcription. The underline indicates the minimum sequence required for efficient transcription.

RNAs may be produced in high yield via in vitro transcription using plasmids such as SPS65 and Bluescript (Promega Corporation, Madison, Wis.). In addition, RNA amplification methods such as Q-β amplification can be utilized to produce the PTM of interest.

The PTMs may be purified by any suitable means, as are well known in the art. For example, the PTMs can be purified by gel filtration, affinity or antibody interactions, reverse phase chromatography or gel electrophoresis. Of course, the skilled artisan will recognize that the method of purification will depend in part on the size, charge and shape of the nucleic acid to be purified.

The PTMs of the invention, whether synthesized chemically, in vitro, or in vivo, can be synthesized in the presence of modified or substituted nucleotides to increase stability, uptake or binding of the PTM to a target pre-mRNA. In addition, following synthesis of the PTM, the PTMs may be modified with peptides, chemical agents, antibodies, or nucleic acid molecules, for example, to enhance the physical properties of the PTM molecules. Such modifications are well known to those of skill in the art.

In instances where a nucleic acid molecule encoding a PTM is utilized, cloning techniques known in the art may be used for cloning of the nucleic acid molecule into an expression vector. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

The DNA encoding the PTM of interest may be recombinantly engineered into a variety of host vector systems that also provide for replication of the DNA in large scale and contain the necessary elements for directing the transcription of the PTM. The use of such a construct to transfect target cells in the patient will result in the transcription of sufficient amounts of PTMs that will form complementary base pairs with the endogenously expressed pre-mRNA targets, and thereby facilitate a trans-splicing reaction between the complexed nucleic acid molecules. For example, a vector can be introduced in vivo such that is taken up by a cell and directs the transcription of the PTM molecule. Such a vector can remain episomal or become chromosomally integrated, as long as it can be transcribed to produce the desired RNA, i.e., PTM. Such vectors can be constructed by recombinant DNA technology methods standard in the art.

Vectors encoding the PTM of interest can be plasmid, viral, or others known in the art, used for replication and expression in mammalian cells. Expression of the sequence encoding the PTM can be regulated by any promoter/enhancer sequences known in the art to act in mammalian, preferably human cells. Such promoters/enhancers can be inducible or constitutive. Such promoters include but are not limited to: the SV40 early promoter region (Benoist, C. and Chambon, P. 1981, *Nature* 290:304-310), the promoter contained in the 3' long terminal repeat of Rous sarcoma virus (Yamamoto et al., 1980, *Cell* 22:787-797), the herpes thymidine kinase promoter (Wagner et al., 1981, *Proc. Natl. Acad. Sci. U.S.A.* 78:14411445), the regulatory sequences of the metallothionein gene (Brinster et al., 1982, *Nature* 296:39-42), the viral CMV promoter, the human chorionic gonadotropin-β promoter (Hollenberg et al., 1994, *Mol. Cell. Endocrinology* 106:111-119), etc.

Any type of plasmid, cosmid, YAC or viral vector can be used to prepare the recombinant DNA construct, which can be introduced directly into the tissue site. Alternatively, viral vectors can be used which selectively infect the desired target cell. Vectors for use in the practice of the invention include any eukaryotic expression vectors, including but not limited to, viral expression vectors, such as those derived from the class of retroviruses, adenoviruses or adeno-associated viruses.

A number of selection systems can also be used, including but not limited to selection for expression of the herpes simplex virus thymidine kinase, hypoxanthine-guanine phosphoribosyltransterase and adenine phosphoribosyl transferase protein in tk-, hgprt- or aprt-deficient cells, respectively. Also, anti-metabolic resistance can be used as the basis of selection for dihydrofolate transferase (dhfr), which confers resistance to methotrexate; xanthine-guanine phosphoribosyl transferase (gpt), which confers resistance to mycophenolic acid; neomycin (neo), which confers resistance to aminoglycoside G-418; and hygromycin B phosphotransferase (hygro) which confers resistance to hygromycin. In a preferred embodiment of the invention, the cell culture is transformed at a low ratio of vector to cell, such that there will be only a single vector, or a limited number of vectors, present in any one cell.

Use and Administration of Trans-Splicing Molecules

The compositions and methods of the present invention are designed to generate novel chimeric RNA molecules containing sequences that express a protein or polypeptide of interest. Specifically, targeted spliceosome mediated trans-splicing, including double-trans-splicing reactions, 3' exon replacement and/or 5' exon replacement can be used to generate such chimeric RNAs. Additionally, ribozyme or t-RNA mediated targeted trans-splicing reactions may be utilized to form chimeric RNAs. A chimeric RNA molecule containing sequences that express a protein or polypeptide of interest of the present invention is translated to generate a protein product comprising the protein or polypeptide of interest. Preferably, the protein or polypeptide of interest is produced in a large scale quantity in the bodily fluid of the host mammal.

Various delivery systems are known and can be used to transfer the compositions of the invention into cells, e.g. encapsulation in liposomes, microparticles, microcapsules, recombinant cells capable of expressing the composition, receptor-mediated endocytosis (see, e.g., Wu and Wu, 1987, *J. Biol. Chem.* 262:4429-4432), construction of a nucleic acid as part of a retroviral, adenoviral, adeno-associated viral or other vector, injection of DNA, electroporation, calcium phosphate mediated transfection, etc.

One or more PTM(s) and the delivery system would constitute the product which could be administered to mammals by conventional administration methods, such as intravenous or intraportal injection. In a specific embodiment of the invention, the chimeric RNA molecule may be distributed throughout the circulation, but would be active in specific cells that express the abundantly expressed target pre-mRNA target, such as hepatocytes, site of albumin synthesis, mammary epithelia, site of casein synthesis and muscle cells, the site of myosin synthesis. The PTM would be active in its RNA form, the binding domain of the PTM adhering to the targeted sequence in the abundantly expressed target pre-mRNA. Following trans-splicing, the coding domain of the PTM would be inserted or trans-spliced to a defined sequence of the target, resulting in a chimeric mRNA that expresses a product comprising the protein or polypeptide of interest.

The albumin gene is highly expressed in the liver, and provides abundant target pre-mRNA. By targeting albumin, the serum concentration of the expressed protein product of interest may be expressed at physiologically, biologically increased or therapeutic levels. Albumin has a serum concentration on the order of 45-50 mg/ml in large mammals, such as cows. Given a moderate trans-splicing efficiency of 5%, large quantities of the expressed protein product of interest can be produced in vivo. Based on a plasma concentration of 45 mg/ml of albumin and a moderate trans-splicing efficiency of 5%, 2.5 mg/ml of the product is generated. The product, which comprises the protein or polypeptide of interest, is generally present at between 2-5 mg/ml in the serum of the animal. With higher efficiency of the splicing reaction, the yield of recombinant protein would be greater. These yields support the concept of using PTMs to generate large scale amounts of recombinant proteins and polypeptides.

The use of casein peptides as the target pre-mRNA also facilitates the goal of producing recombinant proteins and polypeptides in large amounts. Casein proteins represent over 80% of milk proteins. The expressed protein product of the chimeric RNA molecule can be secreted and harvested from the milk obtained from mammals, such as cows.

Delivery of the PTM into a host may be either direct, in which case the host is directly exposed to the PTM or PTM encoding nucleic acid molecule, or indirect, in which case, host cells are first transformed with the PTM or PTM encoding nucleic acid molecule in vitro, then transplanted into the host. These two approaches are known, respectively, as in vivo or ex vivo gene delivery.

In a specific embodiment, the nucleic acid is directly administered in vivo, where it is expressed to produce the PTM. This can be accomplished by any of numerous methods known in the art, e.g., by constructing it as part of an appropriate nucleic acid expression vector and administering it so that it becomes intracellular, e.g. by infection using a defective or attenuated retroviral or other viral vector (see U.S. Pat. No. 4,980,286), or by direct injection of naked DNA, or by use of microparticle bombardment (e.g., a gene gun; Biolistic, Dupont, Bio-Rad), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, *J. Biol. Chem.* 262:4429-4432).

In a specific embodiment, a viral vector that contains the PTM can be used. For example, a retroviral vector can be utilized that has been modified to delete retroviral sequences that are not necessary for packaging of the viral genome and integration into host cell DNA (see Miller et al., 1993, *Meth. Enzymol.* 217:581-599). Retroviral vectors also include lentiviral vectors. Alternatively, adenoviral or adeno-associated viral vectors can be used for gene delivery to cells or tissues. (See, Kozarsky and Wilson, 1993, *Current Opinion in Genetics and Development* 3:499-503 for a review of adenovirus-based gene delivery).

In a preferred embodiment of the invention an adeno-associated viral vector may be used to deliver nucleic acid molecules capable of encoding the PTM. The vector is designed so that, depending on the level of expression desired, the promoter and/or enhancer element of choice may be inserted into the vector.

Another approach to gene delivery into a cell involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. The resulting recombinant cells can be delivered to a mammal by various methods known in the art. In a preferred embodiment, the cell used for gene delivery is autologous to the host's cell.

The present invention also provides for compositions comprising an effective amount of a PTM or a nucleic acid encoding a PTM effective for obtaining production of the protein or polypeptide of interest, and a acceptable carrier. In a specific embodiment, the carrier is a pharmaceutical carrier, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Examples of suitable pharmaceutical carriers are described in "Remington's Pharmaceutical sciences" by E. W. Martin.

Many methods standard in the art can be thus employed, including but not limited to hybridization assays to detect formation of chimeric mRNA expression by detecting and/or visualizing the presence of chimeric mRNA (e.g., Northern assays, dot blots, in situ hybridization, and Reverse-Transcription PCR, etc.), etc.

In a specific embodiment, the compositions of the invention may be administered locally. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Other control release drug delivery systems, such as nanoparticles, matrices such as controlled-release polymers, and hydrogels.

The PTM will be administered in amounts which are effective to produce the desired amounts of chimeric RNA molecule containing sequences encoding recombinant proteins or polypeptides. Effective dosages of the PTMs can be determined through procedures well known to those in the art which address such parameters as biological half-life, bioavailability and toxicity. The amount of the composition of the invention can be determined by standard clinical techniques. Such techniques include analysis of samples to determine if the level of protein or polypeptide of interest has been achieved. In addition, in vitro assays may optionally be employed to help identify optimal dosage ranges.

The present invention also provides a pack or kit comprising one or more containers filled with one or more of the ingredients of the compositions of the invention optionally associated with such container(s) can be a notice in the form prescribed by a governmental agency regulating the manufacture, use or sale of products, which notice reflects approval by the agency of manufacture for use or sale in mammals.

The present invention further provides for methods of large scale bulk productions of a protein or polypeptide of interest comprising administering to a mammal the PTMs of the present invention, contacting the PTM with the abundantly expressed target pre-mRNA under conditions in which a portion of the PTM is trans-spliced to a portion of the target pre-mRNA to form a chimeric RNA molecule that expresses the protein or polypeptide of interest, collecting the bodily fluid from the mammal, and treating the fluid to obtain the protein or polypeptide of interest. The invention can also be used in invertebrates, such as silkworms that express a highly abundant transcript responsible for silk production.

Various mammals are appropriate hosts for large scale bulk production. They include ruminants, such as cattle, goats, deer, sheep, giraffes, and camel. These animals have been domesticated, and produce milk and an abundance of serum. Cattle are preferred.

The protein or polypeptide of interest can be produced in large quantities as long as its presence in the mammal does not trigger an immune response. To minimize such an effect, the mammals may be treated with various immunosuppressive techniques well known to one of skill in the art.

In an embodiment of the invention, the expressed protein product is found circulating in the serum of the mammal. Alternatively, the expressed protein product is in the milk of the mammal.

For the serum, blood is collected from the mammal and centrifuged to separate the serum from the remaining cellular components. The protein can be concentrated and purified by standard methodologies. A similar concentration/purification procedure can be used for other materials, such as milk.

Separation of the protein or polypeptide of interest can be performed using various protein purification techniques well known to one of skill in the art. See, e.g., Scopes, R. K., Protein Purification Principles and Practices, 2d ed. (Springer-Verlag, 1987), Methods in Enzymology (S. Colowick and No. Kaplan, eds., Academic Press, Inc.), Sambrook et al., Molecular Cloning: A Laboratory Manual, 2d ed., Cold Spring Harbor Press, Cold Spring Harbor, N.Y., 1989, Handbook of Experimental Immunology, Vols. I-IV (D. M. Weir and C. C. Blackwell, eds., 1986, Blackwell Scientific Publications); House, Modern Synthetic Reactions, 2d ed., Benjamin/Cummings, Menlo Park, Calif., 1972.

The following examples are meant to exemplify the present invention and as such are not intended or to be interpreted as limiting the scope of the invention.

Example 1

Figure 8:
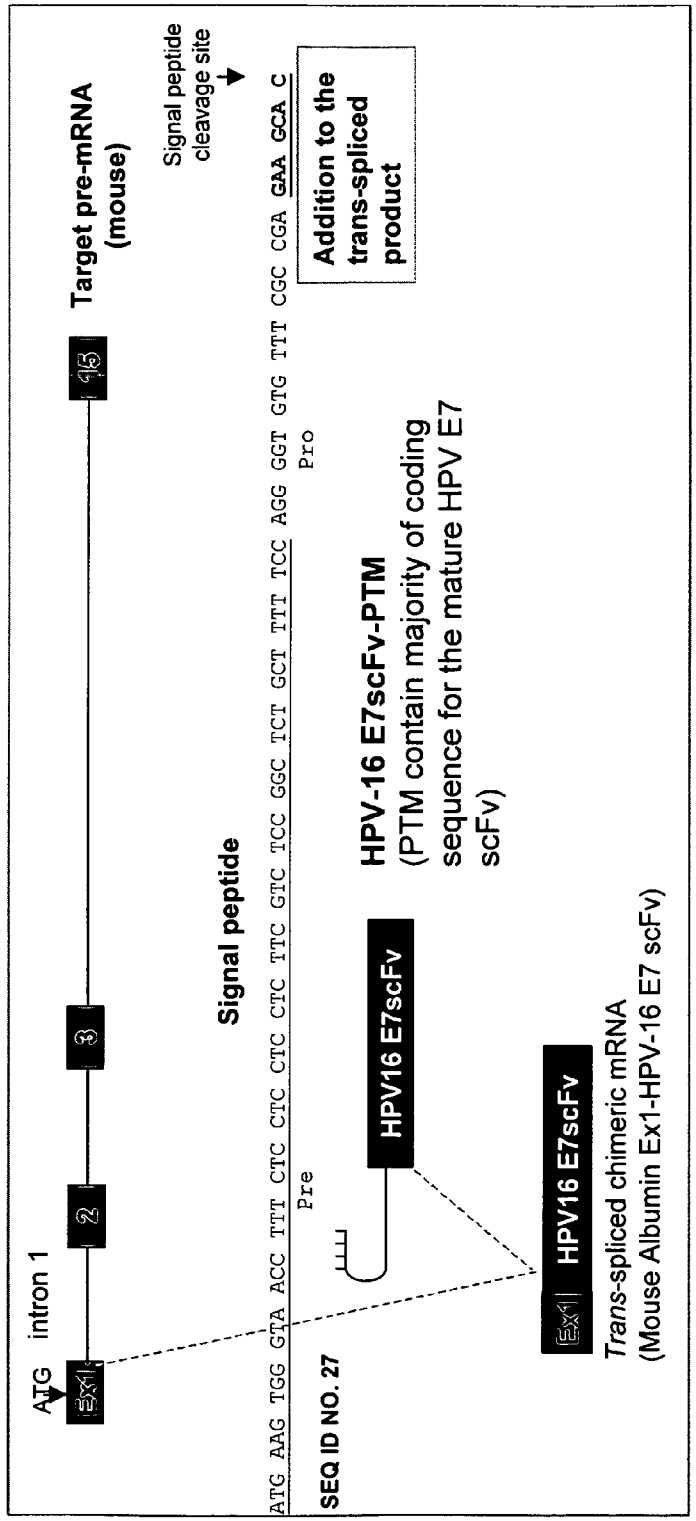
FIG. 8 shows the present invention applied to trans-splicing mediated HPV-16 E7 single chain antibody production strategy.

In Vivo Trans-Spliced Albumin-HPV-16 Anti-E7 Single Chain Antibody (mAlb-HPV-16 Anti-E7 scFv) cDNA The albumin targeting strategy shown in FIG. 8 has been evaluated for the production of human papilloma virus type 16 (HPV-16) anti-E7 single chain antibody in vivo. The concept involves targeted trans-splicing of HPV-16 anti-E7 scFv sequence into albumin pre-mRNA target. Albumin has been selected as a target because of its elevated expression in the liver to provide high albumin pre-mRNA concentration for abundant trans-splicing targets. The present study evaluated the effect of albumin sequences on expression, secretion and function of HPV-16 anti-E7 scFv in vivo.

Figure 9:
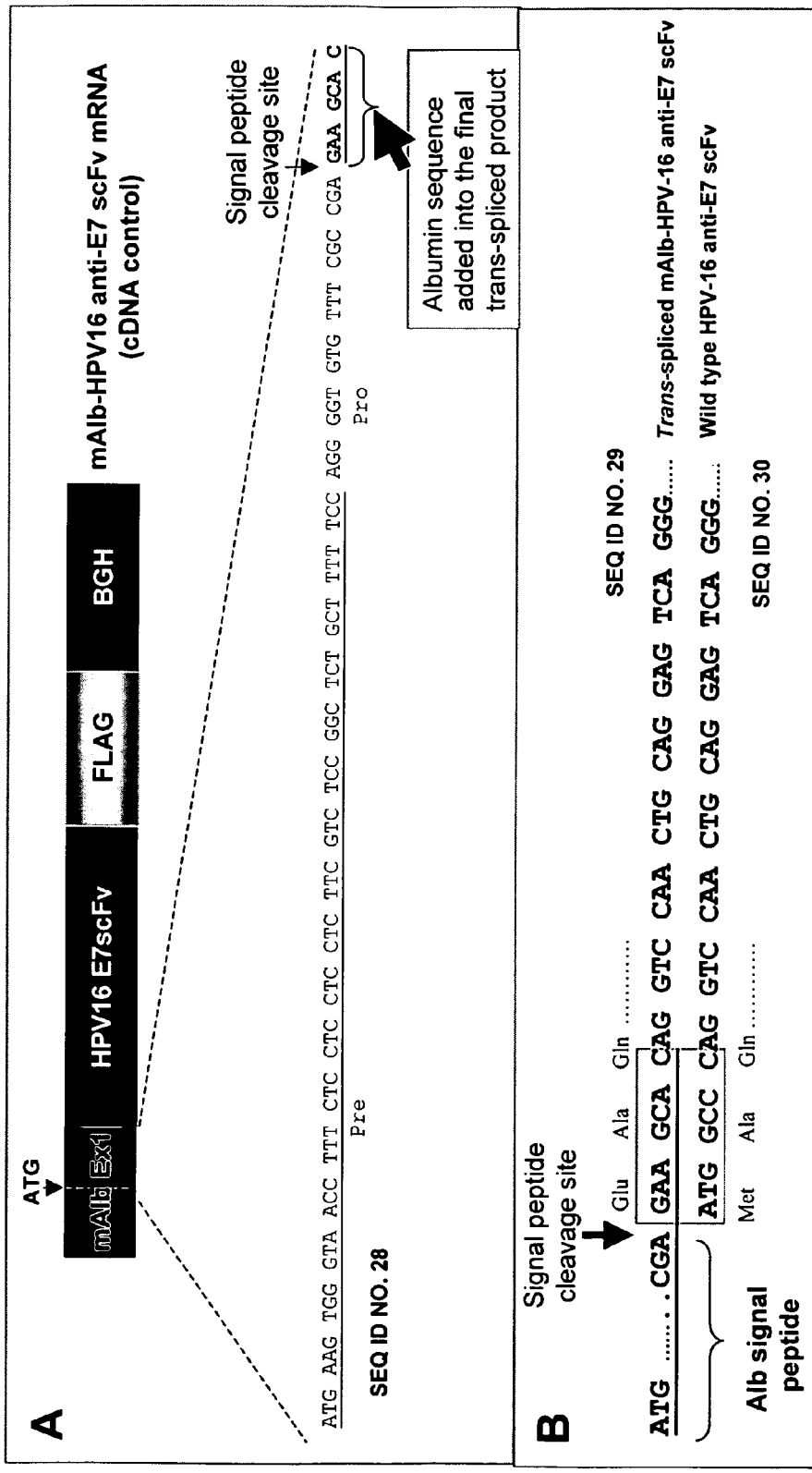
FIG. 9 shows a schematic illustration of mouse albumin exon 1-HPV16 anti-E7 scFv cDNA.

The mouse albumin-HPV-16 anti-E7 scFv (mAlb-HPV16 anti-E7 scFv) positive control cDNA (FIG. 9) was constructed to imitate the final trans-spliced product and tested for expression, processing and secretion in Cos-7 and Hepa1-6 (mouse hepatoma cells) cells. The trans-spliced cDNA expression plasmid was constructed using long synthetic complementary oligonucleotides and PCR product consisting of coding albumin exon 1 and HPV-16 anti-E7 scFv sequence. The coding sequence of mouse albumin exon 1 was assembled using the following long oligonucleotides: forward primer (SEQ ID NO:9):

GCTAGCATGAAGTGGGTAACCTTTCTCCTCCTCCTCTTCGTCTCCGGCTC

TGCTTTTTCCAGGGGTGTGTTTCGCCGAGAAGCACAGGTCCAACTGCAGG

AGTCAGGG GCTGAGC, and reverse primer (SEQ ID NO:10):

GCTCAGCCCCTGACTCCTGCAGTTGGACCTGTGCTTCTCGGCGAAACACA

CCCCTGGAAAAAGCAGAGCCGGAGACGAAGAGGAGGAGGAGAAAGGTTAC

CCACTTCATGCTA

GC. (The nucleotides in bold include NheI and BlpI restriction sites used for cloning; underlined nucleotides include the mouse albumin exon 1 sequence, in which the majority codes for signal peptide; and the italicized nucleotides include partial HPV-16 anti-E7 scFv sequence).

HPV-16 anti-E7 scFv coding sequence was PCR amplified using a cDNA clone and primers: Sca1 (5'-GCTAGCATG-GCCCAGGTCCAACTGCAGG) (SEQ ID NO:11) and Sca5 (5'-AAGCTT TCA CTTGTCGTCATCGTCTTTGTAGTCCCGTTTTATTTCC GCTTG GTCCCAGC) (SEQ ID NO:12) (nucleotides in bold, NheI and Hind III restriction sites for cloning; italicized nucleotides, stop codon; and the underlined nucleotides, FLAG tag). The PCR product was digested with BlpI and HindIII restriction enzymes. The resulting product was first ligated with the annealed oligo fragment and then ligated into pcDNA3.1 expression vector (Invitrogen). The authenticity of the PTM cassette sequence was verified by sequencing (FIG. 10).

Example 2

Production, Expression and Secretion of Albumin-HPV-16 Anti-E7 scFv Antibody in Hepa1-6 and Cos-7 Cells The effect of the albumin exon 1 sequence (7 nucleotides) on expression and processing of HPV-16 anti-E7 scFv was evaluated by transfecting the trans-spliced cDNA plasmid along with a control plasmid (similar to the trans-spliced cDNA without the FLAG tag) into mouse hepatoma, Hepa1-6 and Cos-7 cells. 48 hrs post-transfection, medium was collected, passed through FLAG affinity column (Sigma, Cat #FLAGIPT-1) and analyzed by Western blot for the expression of HPV-16 anti-E7 scFv using anti-FLAG M2 monoclonal antibody (Sigma, Cat #F 3165).

Figure 11:
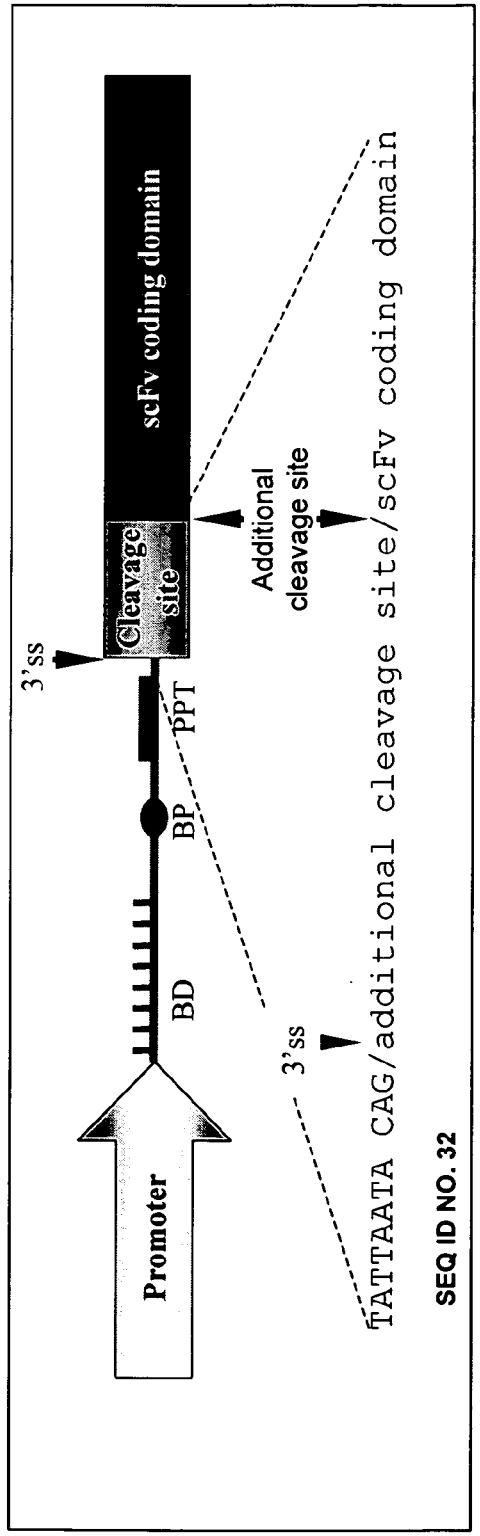
FIG. 11 shows a schematic illustration of PTM containing additional endopeptidase cleavage site. The PTM structure is similar to scFv PTM except that it has an additional endopeptidase cleavage site or a native "Pro"-peptide sequence.
Figure 12:
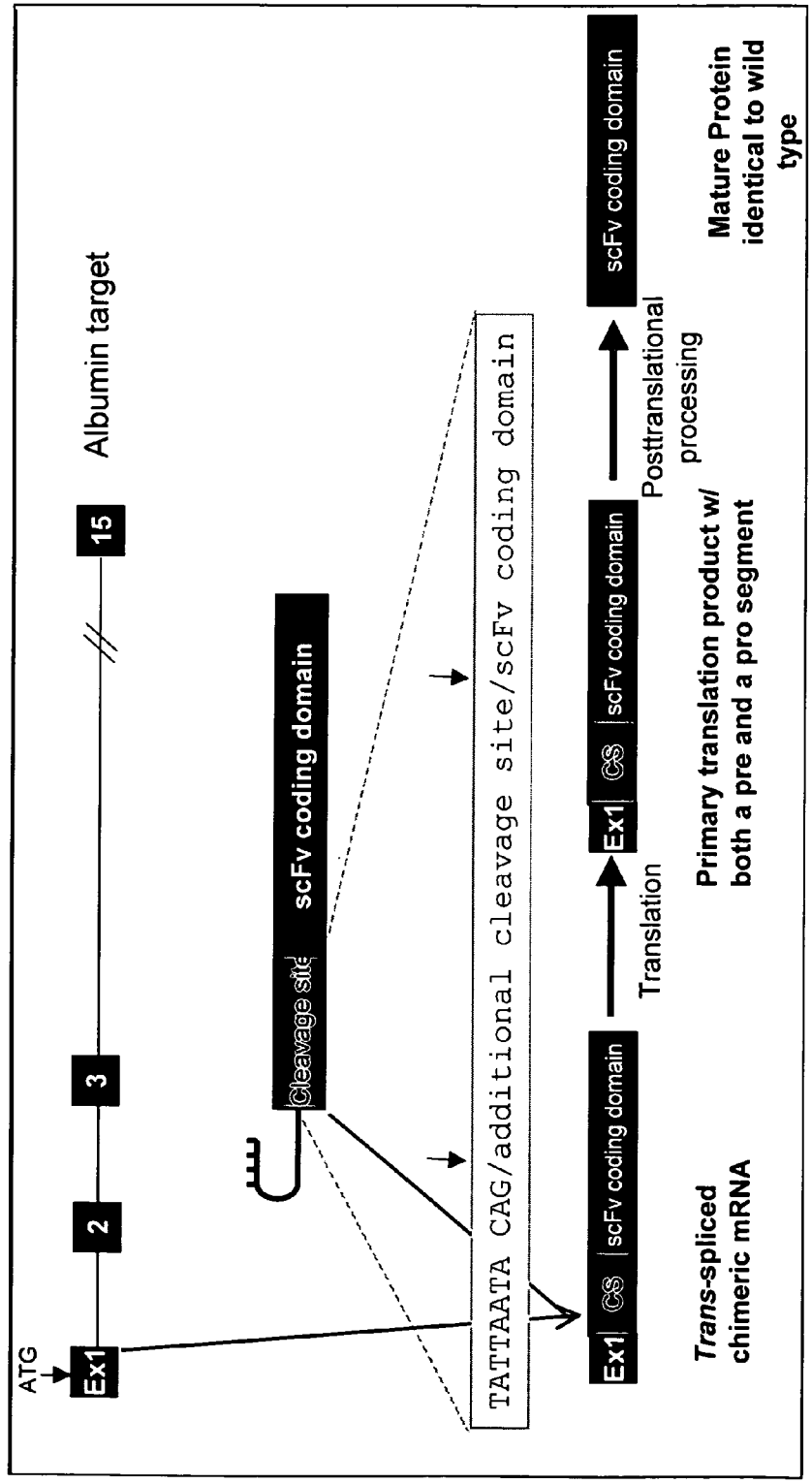
FIG. 12 shows a schematic illustration of trans-splicing strategy to eliminate albumin sequence in the final product. Ex1, exon 1 of albumin; CS, additional cleavage site.

The current albumin trans-splicing strategy results in the production of chimeric mRNA and protein. The final trans-spliced product contains 7 nucleotides or 2 amino acids from albumin target mRNA. For human applications it may be desirable to eliminate the albumin sequence in the final product to preclude immunological reactions. In one exemplary strategy, illustrated in FIG. 11, the PTM will be engineered to encode "Furin" like endopeptidase (or proprotein convertase) cleavage site which has been used to express proteins in vivo (Fuller R S, Brake A J, Thorner J, Science, 246: 482-486, 1989; Bresnahan P A, Leduc R, Thomas L, Thorner J, Gibson H L, Brake A J, Barr P J, Thomas G., J Cell Biol. 111:2851-2859, 1990; van de Ven W J, Voorberg J, Fontijn R, Pannekoek H, van den Ouweland A M, van Duijnhoven H L, Roebroek A J, Siezen R J, Mol Biol Rep. 14:265-75, 1990; Duckert P, Brunak S, Blom N. Protein Eng Design & Selection. 17:107-112, 2004). In another example, the PTM will be designed to include the protein's own native secretion signal, i.e., "pre-pro" signal (if it has one). This strategy was designed to take advantage of the endogenous native cellular machinery to enhance recognition, processing and secretion of the final trans-spliced protein to the site of action similar to wild type protein. For example, trans-splicing of PTM into albumin pre-mRNA target produces a chimeric mRNA and pre-pro-protein that in addition to signal peptide cleavage in rough endoplasmic reticulum undergoes several post-translational modifications in other cellular compartments and, finally, endopeptidase cleavage resulting in the release of a mature, fully processed biologically active protein that is identical to the wild type (FIG. 12).

Figure 13:
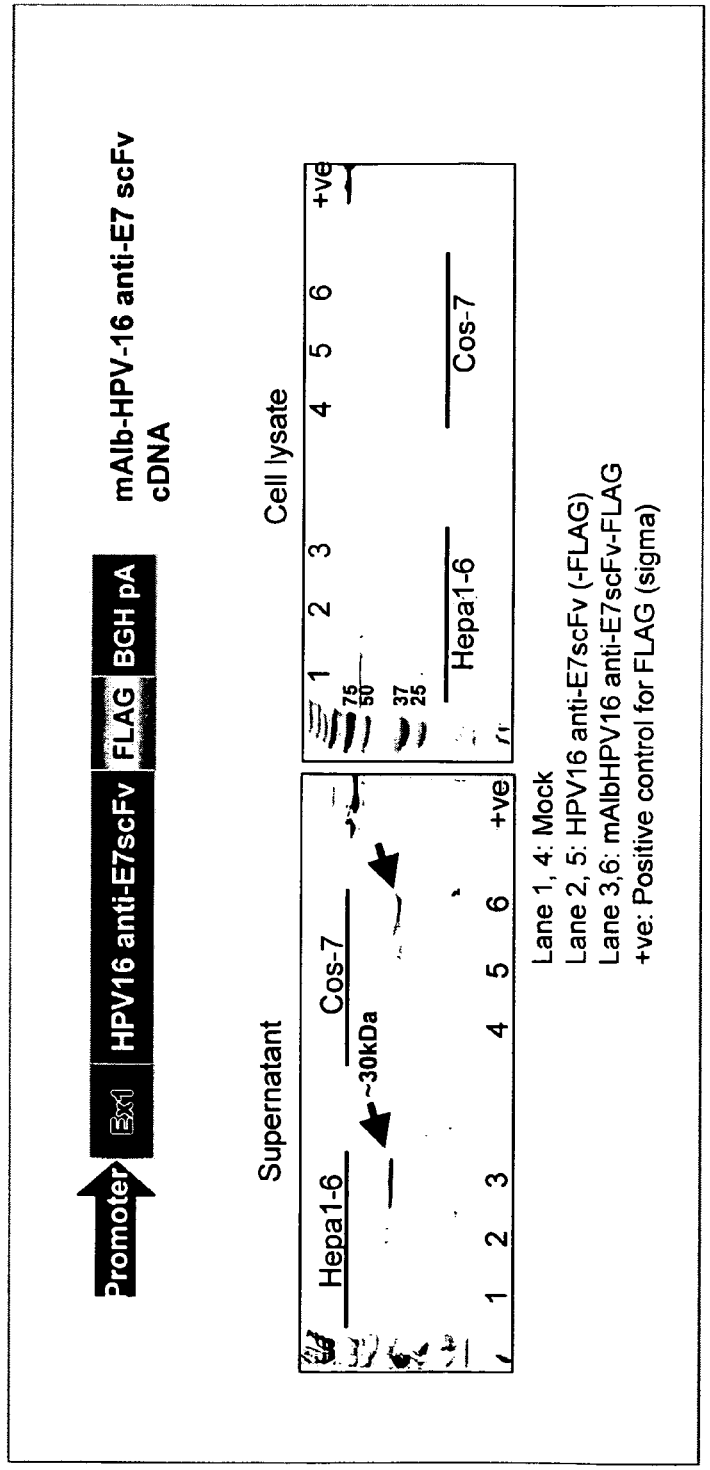
FIG. 13 shows a SDS gel showing the production of HPV16 anti-E7 scFv in Hepa1-6 cells. Mouse albumin-HPV16 anti-E7 scFv cDNA (identical to the trans-spliced mRNA) was transfected into Hepa1-6 and Cos-7 cells. 48 hrs post-transfection, supernatant and cell lysate was prepared and analyzed by Western blot using anti-FLAG M2 monoclonal antibody. Arrows indicate the expected ~30 kDa mouse albumin—HPV16 anti-E7 scFv.

About 10 µg of total protein from the supernatant or the total cell lysate from cells transfected with cDNA expression plasmids was analyzed on a 12% SDS-PAGE and transferred onto nylon membrane and probed with anti-FLAG antibody. Western results confirmed the production of HPV-16 anti-E7 scFv, 30 kDa in size predicted for the mature protein in cells that were transfected with FLAG-tagged cDNA expression plasmid in both Hepa1-6 and Cos-7 cells (FIG. 13 lanes 3 & 6, left panel). On the other hand, no such product was detected in mock and in cells that received the cDNA construct without the FLAG tag (FIG. 13 lanes 1-2 and 5-6, left panel). In addition, no protein was detected in the cell lysate (FIG. 13) indicating that the majority of the protein processed and secreted normally.

Example 3

Trans-Spliced Albumin HPV-16 Anti-E7 scFv Protein is Functionally Active

The effect of the albumin sequence on HPV-16 anti-E7 scFv function was evaluated by its ability to down regulate HPV-16 E7 expression in cervical cancer cells. Cervical cancer cells, SiHa, (ATCC #HTB-35) that are HPV-16 E7 oncoprotein positive was transfected with mAlb-HPV-16 anti-E7 scFv cDNA expression plasmid. The matching control cells, C-33A (ATCC #HTB-31) that do not express E7 oncoprotein was also transfected with the mAlb-HPV-16 anti-E7 scFv cDNA expression plasmid. Cells were grown for 5 days and the number of relative viable cells was determined by colorimetric (MTT) assay.

Figure 14:
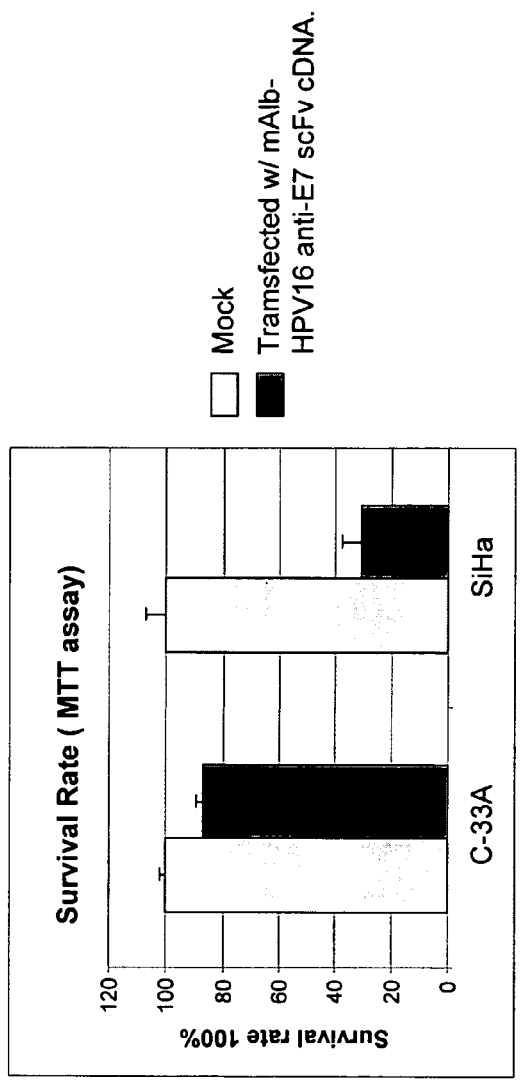
FIG. 14 shows the trans-spliced mAlb-HPV16 anti-E7 scFv function in cells. HPV-positive cervical cancer cells, SiHa, or the matching HPV-negative cells were transfected with mAlb-HPV16 anti-E7 scFv expression cDNA plasmid. Cells were grown for 5 days and assayed for cell survival using MTT assay.

In the case of HPV-16 positive cervical cancer cells, SiHa, mAlb-HPV-16 anti-E7 scFv inhibited cell proliferation by ~75% compared to about <10% inhibition in C-33A HPV-negative cells and thereby demonstrated the functionality of the trans-spliced albumin HPV-16 anti-E7 scFv antibody (FIG. 14). These results not only confirmed the absence of any major adverse effects due to albumin sequence in the final trans-spliced product on HPV-16 anti-E7 scFv function, but also provide evidence of the effectiveness of the compositions of the present invention for the production of functional antibody polypeptides and/or therapeutic proteins in vivo.

Figure 15:
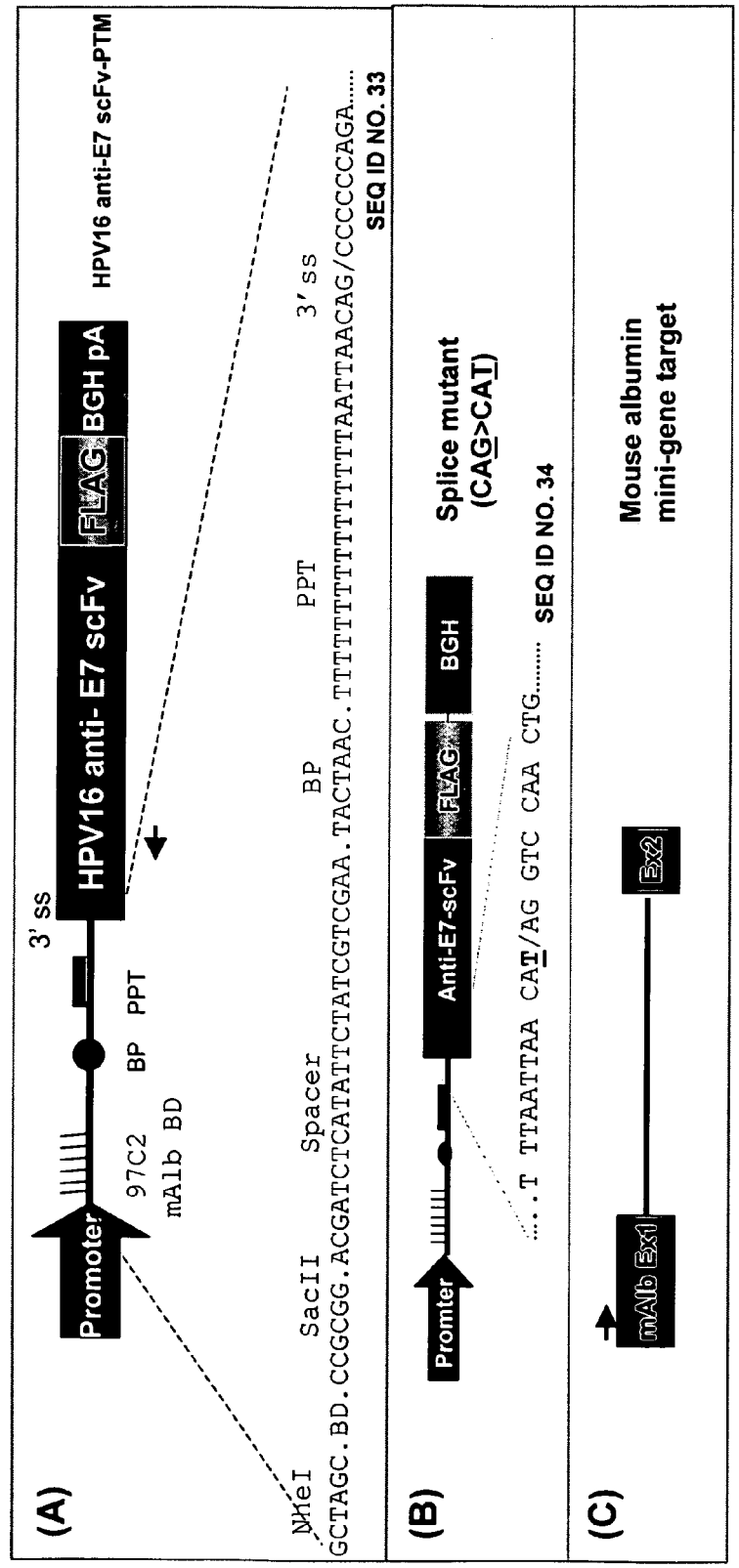
FIG. 15 shows a schematic of HPV16 anti-E7 scFv PTM (A), splice mutant (B) and mouse albumin mini-gene target (C), used for in vitro POP studies. PTM cassette consists of a trans-splicing domain which includes mouse albumin intron 1 specific binding domain (BD), short spacer, consensus sequence branch point (BP), optimized polypyrimidne tract (PPT), 3' acceptor site (CAG) followed by the majority of the coding sequence of HPV16 anti-E7 scFv sequence. PTM Expression is driven by CMV promoter. At the 3' end, the PTM also it contains FLAG epitope followed by bovine growth hormone polyadenylation signal (BGH pA). Splice mutant is identical to the functional PTM but has a point mutation at the acceptor site (CA$\underline{G}$>CA$\underline{T}$). ss, 3' splice site; arrows indicate primers used for trans-splicing assays.

The structure of HPV-16 anti-E7 scFv PTM expression cassette used for the proof-of-principle study is illustrated in FIG. 15A. The PTM cassette consists of a trans-splicing domain (TSD) that includes 279 nts binding domain complementary to mouse albumin intron 1, 24 nucleotide spacer region, strong 3' splice elements such as the consensus yeast branch point (BP), an optimized polypyrimidine tract, a splice acceptor site (CAG dinucleotide) followed by the majority of the coding sequence for HPV-16 anti-E7 scFv (FIG. 13). The PTM cassette also contains bovine growth hormone polyadenylation signal and FLAG tag to assist in the detection of trans-spliced protein. The entire cassette was cloned into the pcDNA3.1 vector backbone, which contains the cytomegalovirus (CMV) promoter (Invitrogen). In addition, the vector backbone was further modified to include the Maz4 (transcriptional pause site) sequence to reduce cryptic cis-splicing between vector ampicillin gene and the PTM 3' splice site.

A splice mutant (splice incompetent) was also constructed that was identical to the functional PTM described above but had a point mutation at the acceptor site (CA<u>G</u>>CA<u>T</u>) (FIGS. 15A and 15B). The splice mutant was used as a negative control. For in vitro proof-of-principle studies, a mouse albumin mini-gene target pre-mRNA was used that consisted of exon 1, intron 1 and exon 2. A schematic diagram of the pre-mRNA target is illustrated in FIG. 15C.

Figure 16:
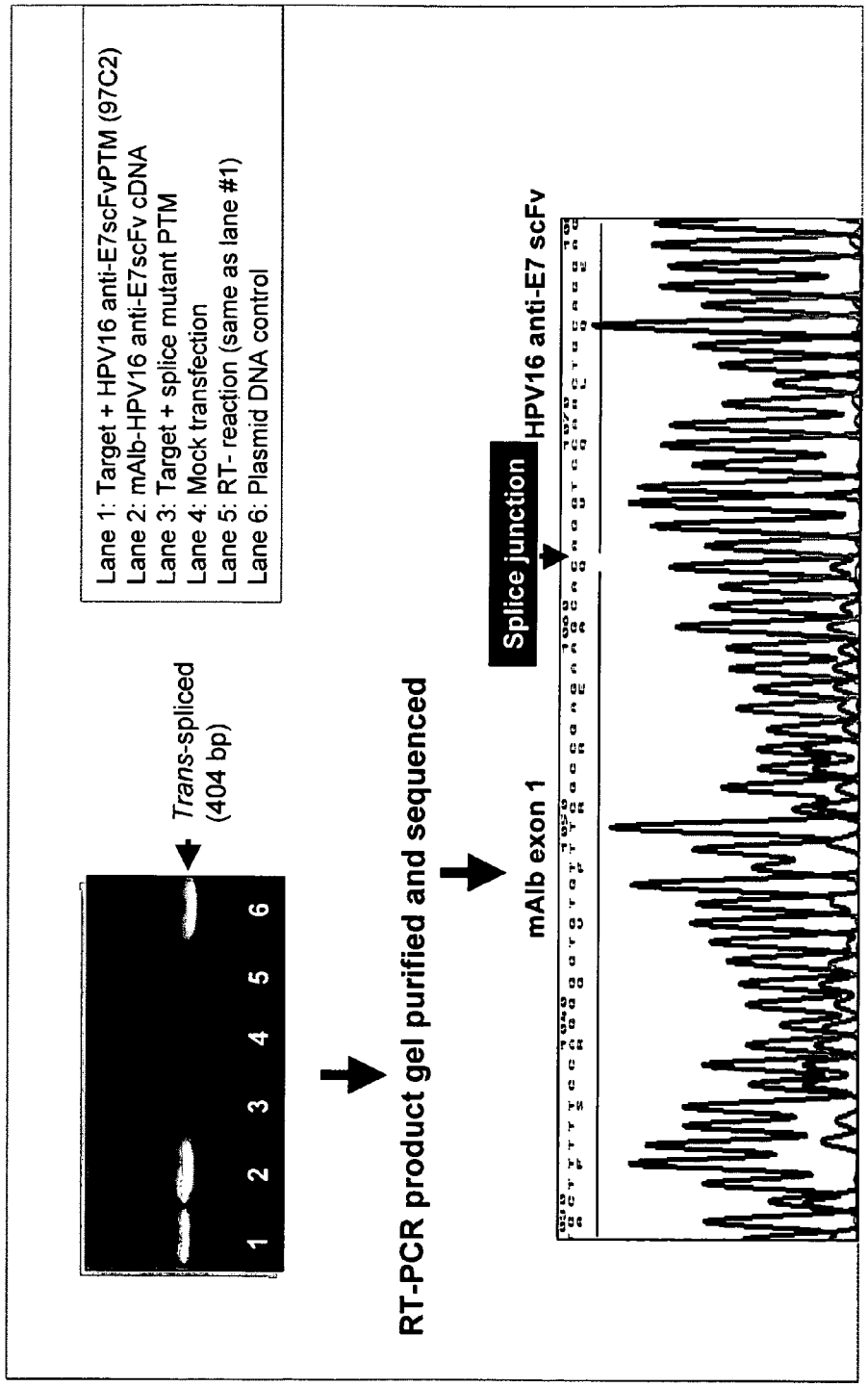
FIG. 16 shows the precise trans-splicing of HPV16 anti-E7 scFv PTM into mouse albumin exon 1 in cells.

PTM mediated trans-splicing and production of mouse albumin-HPV-16 anti-E7 scFv chimeric mRNA was evaluated by co-transfecting Hepa1-6 cells with mouse albumin mini-gene target plasmid along with HPV-16 anti-E7 scFv PTM (functional PTM) or with the splice mutant (splice incompetent PTM) and mock transfection. Total RNA isolated from these cells was analyzed by RT-PCR using mouse albumin exon 1 (AlbA1TSF2: ACCTTTCTCCTCCTC-CTCTTCGT) (SEQ ID NO:13) and HPV-16 anti-E7 scFv PTM (sca3: AGTAAGCAAACCAGTAGCCGTC) (SEQ ID NO:14) specific primers (primer binding sites indicated in FIGS. 15A and 15C). These primers produced the predicted 404 bp product only in cells that received both target and functional PTM (FIG. 16, lane 1) which co-migrated along with a similar size band observed with cDNA control (FIG. 16, lane 2) and plasmid DNA (FIG. 16, lane 6). No RT-PCR product was detected in cells transfected with the splice mutant (FIG. 16, lane 3) or in mock transfection (FIG. 16, lane 4). The PCR product was purified and was directly sequenced, confirming the precise trans-splicing to the predicted splice sites of the PTM and the target pre-mRNA in these cells (FIG. 16, lower panel). Thus, the above results establish that the methods of the present invention may be used to provide efficient trans-splicing of HPV-16 anti-E7 scFv PTM in vitro.

Example 4

In Vivo Trans-Splicing to Endogenous Mouse Albumin Pre-mRNA Target and Production of HPV-16 Anti-E7 scFv in Mice To demonstrate trans-splicing of the PTM into an endogenous mouse albumin target and production of HPV-16 anti-E7 scFv protein, the following experiments were conducted. One hundred micrograms of mAlb-HPV16 anti-E797C2 (PTM only), 70 μg of PTM+35 μg of mini-gene target (additional target plasmid to increase pre-mRNA concentration) or 100 μg of the control cDNA (mAlb-HPV16 anti-E7scFv) plasmid that mimics trans-spliced mRNA were hydrodynamically injected via tail vein into normal C57BL/6 mice. Serum samples were collected at 8, 16 and 24 hrs time points and analyzed by Western blot. Approximately, 25-100 μl serum was passed through FLAG affinity column, samples were then separated on a 12% SDS-PAGE, transferred on to nitrocellulose membrane and probed with anti-FLAG M2 monoclonal antibody. Proteins were visualized using a chemiluminescence kit (Invitrogen, Cat #WB7103).

Figure 17A:
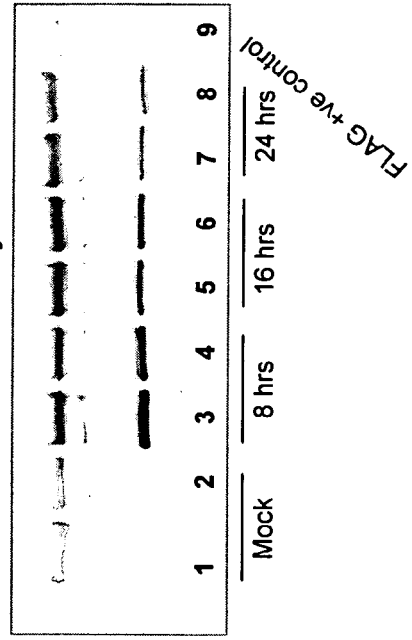
FIG. 17A shows Western blot analysis of serum samples from mice injected with mAlb-HPV16 anti-E7 scFv cDNA. 25 µl serum was passed through FLAG affinity column and analyzed by Western blot using anti-FLAG M2 monoclonal antibody.
Figures 17B, 17C:
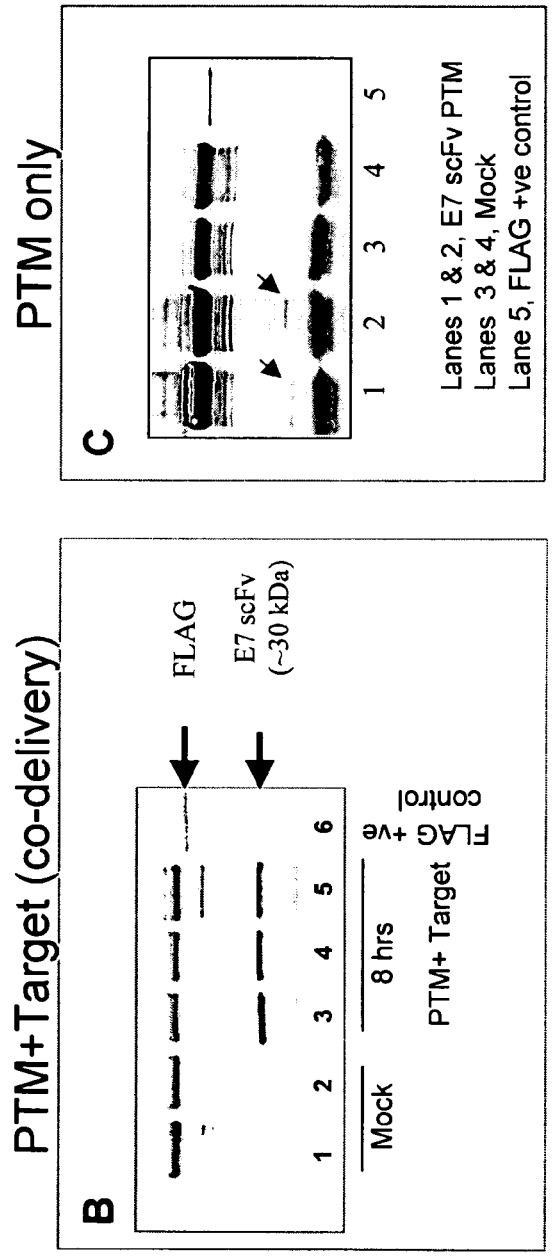
FIG. 17B shows Western blot analysis of serum from mice injected with HPV16 anti-E7 scFv PTM only. 50-100 µl serum was passed through FLAG affinity column and analyzed by Western blot using anti-FLAG M2 monoclonal antibody.
FIG. 17C shows Western blot analysis of serum from mice injected with HPV16 anti-E7 scFv PTM+target. 50-100 µl serum was passed through FLAG affinity column and analyzed by Western blot using anti-FLAG M2 monoclonal antibody.

Western blot results indicated the appearance of HPV-16 anti-E7 scFv in the circulation of the mice as early as 8 hrs post-injection with the cDNA control expression plasmid (FIG. 17A, lanes 3 and 4) and the levels dropped significantly at 24 hrs (FIG. 17A, lanes 7 and 8). Efficient trans-splicing and production of predicted 30 kDa HPV16 anti-E7 scFv was also detected in mice that received both the target and PTM (FIG. 17B, lanes 3-5, left panel). On the other hand, no such band was detected in mock treated mice (FIG. 17B, lanes 1-2, left panel). Finally, mice that received only the PTM (targeting endogenous target) also showed the presence of a 30 kDa HPV16 anti-E7 scFv (FIG. 17C, lanes 1-2). These results clearly show: (a) successful and accurate trans-splicing of mouse albumin PTM into a mouse albumin target pre-mRNA, (b) production of HPV16 anti-E7 scFv through trans-splicing. In addition, the above results further validate the targeting strategy of the present invention for the production of therapeutic antibody polypeptides and fragments thereof in vivo.

Example 5

Double Chain Antibody Production

Figure 18:
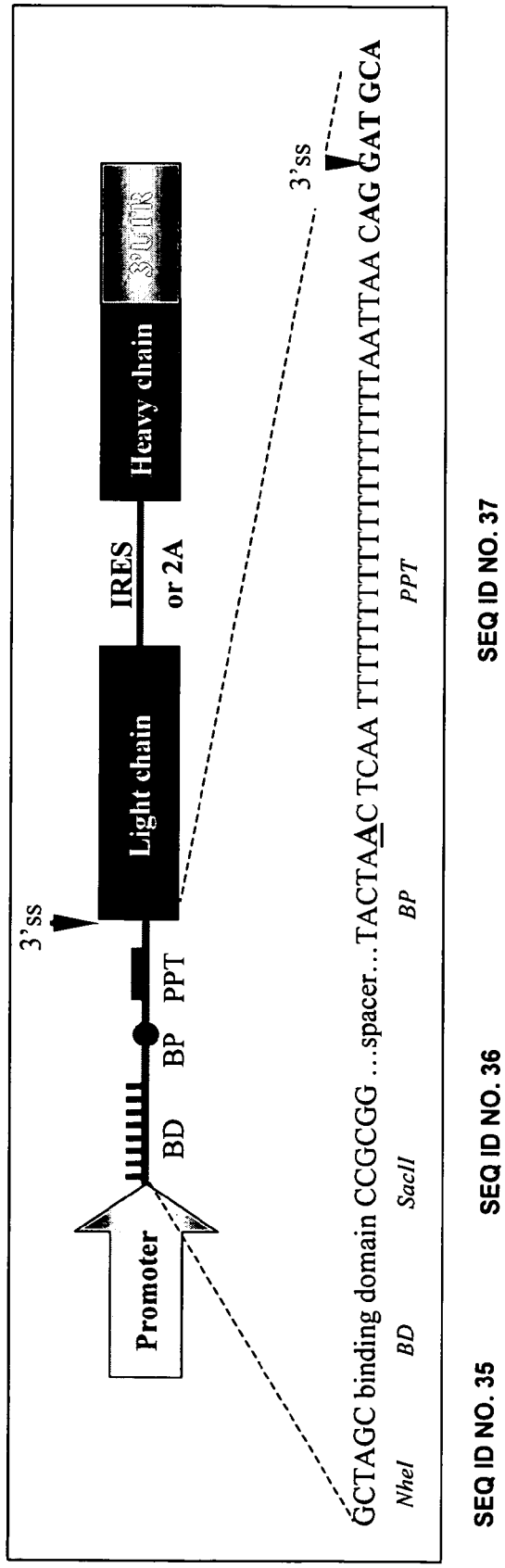
FIG. 18 shows a schematic representation of a bicistronic PTM for the production of whole antibodies, the PTM cassette consists of a trans-splice domain (TSD) including: binding domain, short spacer, BP, PPT, coding sequence for the entire light chain, 2A self-processing peptide from the foot and mouth disease virus (FMDV) or the encephlomayocardities (ECMV) internal ribosome entry site (IRES) followed by the full length coding sequence of heavy chain. Abbreviations: BD, binding domain; BP, branch point; PPT, polypyrimidine tract; 3'ss, splice site.

According to some embodiments, the PTM cassettes of the present invention may be modified to produce antibodies containing both the light and heavy chain. As illustrated in FIG. 18, the bicistronic PTM cassette is similar to the HPV-16 E7 scFv PTM shown in FIG. 15A, except that it may contain, after the coding domain for the single chain antibody sequence, 2A self-cleaving oligo peptide derived from Foot and Mouth Disease Virus (FMDV) (Fang et al., *Nature Biotechnol*, 23: 584, 2005, the disclosure of which is hereby incorporated by reference) or the encephlomayocarditties (ECMV) internal ribosome entry site (IRES) (Martienz-Salas, *Curr Opin Biotechnol*, 10:458, 1999, the disclosure of which is hereby incorporated by reference) sequence followed by the full length coding sequence to induce high levels of translation of the second chain. The use of the 2A oligo peptide and/or the IRES sequence to express the second transgene has been well documented (Fang et al., *Nature Biotechnol*, 23: 584, 2005; Martienz-Salas, *Curr Opin Biotechnol*, 10:458, 1999). In addition, PTMs encoding single chain and the second chain (separate PTMs) could also be used for the production of double chain antibodies.

Example 6

Figure 19:
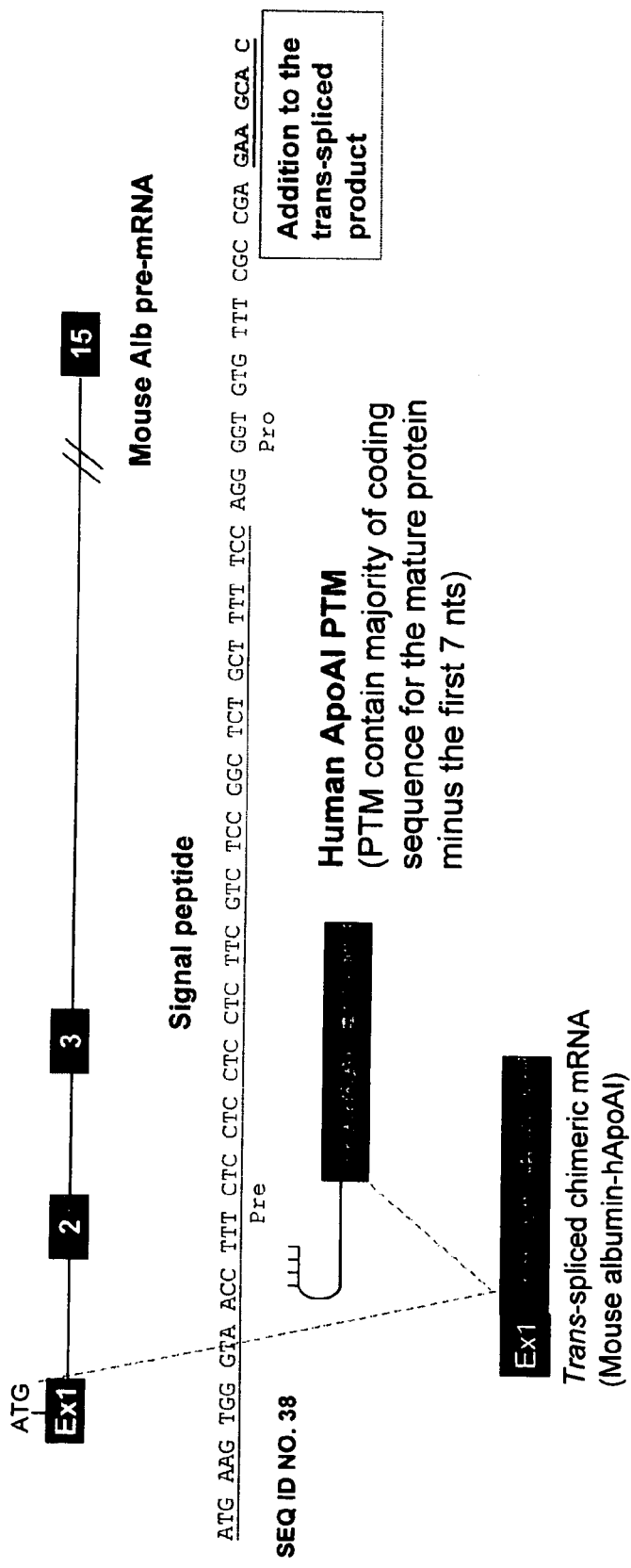
FIG. 19 Schematic of targeted trans-splicing of human ApoA-1 into albumin target pre-mRNA. Nucleotides in bold, indicate the human albumin sequence (7 nts) that are added to final trans-spliced product.

Expression of Human Apolipoprotein (APO A-1) Albumin-Human APO A-1 Fusion Proteins The present study was undertaken to evaluate albumin targeting strategy (FIG. 19) for the production of human Apo A-1 protein, major component of high density lipoprotein (HDL) or other variants and subsequently increase HDL concentration as a treatment for individuals having or at risk for cardio vascular disease (CHD). The rationale for selecting albumin as a target is because of its elevated expression in liver. High albumin pre-mRNA concentration results in abundant targets for trans-splicing. The concept involves targeted trans-splicing of wild type human Apo A-1 or Apo A-1 analogues into albumin pre-mRNA target; and the goal is to increase Apo A-1 expression. This study evaluates the effect of albumin sequence human Apo A-1 protein expression, secretion and function.

Figure 20:
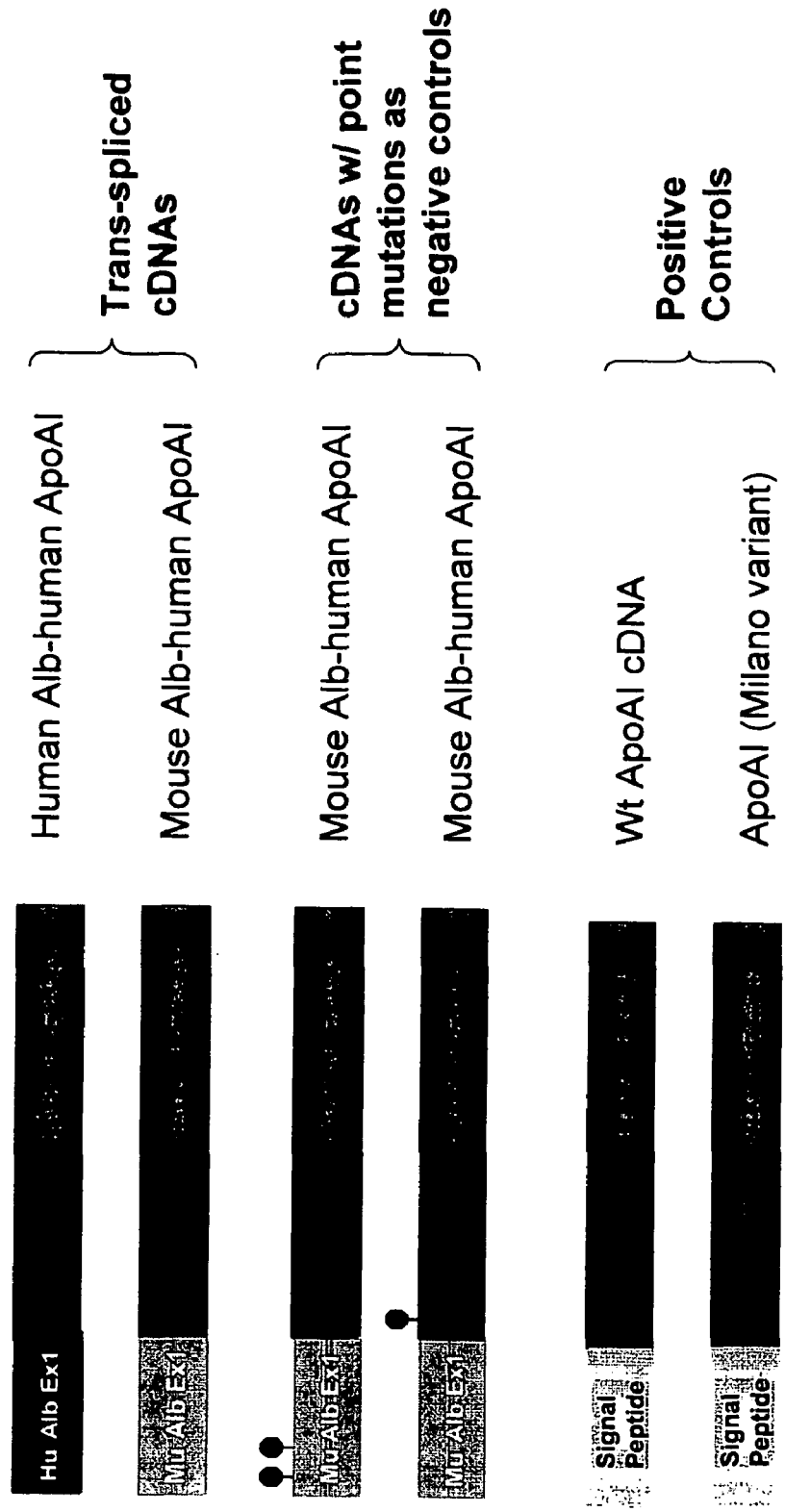
FIG. 20 Schematic of human and mouse albumin-human Apo A-I cDNA constructs (test constructs), similar constructs with point (deletion) mutants (negative controls) and wild type human Apo A-I and milano variants (positive controls).

The fusion (albumin-Apo A-1) function in vivo was evaluated. Human and mouse versions of the albumin-human Apo A-1 cDNA controls (FIG. 20) were constructed to mimic the final trans-spliced product for expression, processing and function in 293 and hepatoma cells (HepG2). The fusion cDNA constructs were constructed using long complementary oligonucleotides and PCR products consisting of albumin exon 1 and human Apo A-1 exon 3 and 4. Briefly, the coding sequence of mouse and human albumin exon 1 were assembled using the following long oligos:

```
mouse Alb forward primer (SEQ ID NO: 15):
ATGAAGTGGGTAACCTTTCTCCTCCTCCTCTTCGTCTCCGGCTCTGCTTT
TTCCAGGGGTGTGTTTCGCCGAGAAGCACCC, reverse primer (SEQ ID NO: 16):
GGGTGCTTCTCGGCGAAACACACCCCTGGAAAAAGCAGAGCCGGAGACGA
AGAGGAGGAGGAGAAAGGTTACCCACTTCATG,
and human Alb forward primer (SEQ ID NO: 17)::
ATGAAGTGGGTAACCTTTATTTCCCTTCTTTTTCTCTTTAGCTCGGCTTA
TTCCAGGGGTGTGTTTCGTCGAGATGCACCC,
``` reverse primer (SEQ ID NO:18):: GGGTGCATCTCGAC-GAAACACACCCCTGGAATAAGC-CGAGCTAAAGAGAAAAAGA AGGGAAATAAAGGT-TACCCACTTCATG. The underlined nucleotides indicate the end of albumin exon 1 sequence and 2 "C"s at the 3' end of the forward primers overlap to human Apo A-1.

Human Apo A-1 coding sequence was PCR amplified using a cDNA clone (ATCC: clone #MGC-1249) and primers: Apo23 (SEQ ID NO:19) (5'-CCCCAGAGCCCCTGG-GATCGAGTG) and Apo5 (SEQ ID NO:20) (5'-CTAG AAGCTT CCCACTTTGGAAACGTTTAT TCTGAG-CACC GG). The PCR product was blunted at the 5' end and then digested with Hind III (indicated in bold) restriction enzyme. The resulting product was first ligated with mouse or human albumin exon 1 and then cloned into pcDNA3.1 expression vector (Invitrogen). Expression plasmids containing the entire coding sequence of human Apo A-1 including the signal peptide into pcDNA3.1 to generate wild type human Apo A-1, and the Milano variant which contains an Arg to Cys substitution at position 173 (R173C) expression plasmids were also constructed as positive controls. The final constructs were verified by sequencing.

Production, Expression and Secretion of Albumin Apo A-1 Fusion Proteins in 293 Cells The effect of albumin exon 1 sequence on expression and processing of human Apo A-1 protein was evaluated by transfecting human and mouse fusion cDNA plasmids along with a negative (deletion mutant) and a positive control cDNAs (wt Apo A-1) into 293 cells. After transfection, cells were rinsed 2× with serum free DMEM and incubated with serum free advanced DMEM media (Invitrogen). After 48 hrs post-transfection, media was collected, concentrated, analyzed for the expression of human Apo A-1 protein.

Coomassie Blue staining of the gel revealed that both the mouse and the human fusion cDNAs produced the predicted ~28 kDa protein band which co-migrated with that of wt Apo A-1 demonstrating good expression, processing and secretion in 293 cells (FIG. 21, lanes 2-3, 6-7). In addition, these data also showed that the level of expression was similar to that of wt Apo A-1 (FIG. 21, lane 4, 8) indicating no adverse effects of albumin sequence on human Apo A-1 expression and processing. On the other hand, no such band was detected in mock and in cells that received mouse fusion cDNA with 2 nucleotide deletion in the signal peptide (FIG. 21, lane 1 and 5).

The identity of the band that was observed in SDS gel as human Apo A-1 was confirmed by Western analysis using a monoclonal human Apo A-1 antibody (Biodesign, Cat. #H45625). About ~5-10 μg total protein from the supernatant or the total cell lysate from cells transfected with fusion cDNA constructs, wt Apo A-1 and Milano variant was analyzed on a 12% SDS gel and transferred onto nylon membrane and incubated with human anti-Apo A-1 antibody. Western results confirmed the production of human Apo A-1 protein with an apparent molecular mass of 28 kDa predicted for the mature protein. Western data also indicated the presence of >90% of the mature human Apo A-1 protein from the fusions or wt Apo A-1 in the supernatant compared to cell lysate demonstrating normal processing and secretion in 293 cells (FIG. 22, compare lanes 1 & 2 with 3). Similar results were also observed with hepatoma (HepG2) cells transfected with fusion cDNA constructs.

Albumin Apo A-1 Fusion Protein is Functionally Active

The effect of albumin sequence on human Apo A-1 function was evaluated by measuring ATP-binding cassette transporter protein (ABC1) mediated transfer of cellular cholesterol into Apo A-1 acceptor. The release of radio-labeled cellular cholesterol to lipid free human Apo A-1 was quantified and the efflux values obtained with fusion proteins was compared with those from wt Apo A-1 and negative control samples. Control HeLa and HeLa cells stably transfected with ABC1 plasmid were grown to near confluency. Cells were then loaded with 1 μCi/ml $^3$H cholesterol. After equilibrating for 24 hrs, cells were washed 3× with serum free media and incubated with a serial dilution of the media containing the fusion proteins (supernatant from 293 cells transfected w/fusion cDNA constructs, normalized for Apo A-1 protein concentration) or with 10 μg/wild type Apo A-1 protein as positive control. Cells were allowed to efflux for 18 hrs. After the efflux period, media was collected and an aliquot of the medium was then counted by liquid scintillation counting. The remaining counts in the cell fraction were determined after an over night extraction with isopropanol. The percent efflux was calculated by dividing the counts in the efflux media by the sum of the counts in the media plus the cell fraction. DMEM/BSA media was used as a blank and was subtracted from the radioactive counts obtained in the presence of an acceptor in the efflux media.

The amount of ABC1 mediated efflux observed with fusion proteins (mouse and human fusion proteins) was similar to that of wt Apo A-1 (FIG. 23). The efflux data also demonstrated that the absolute efflux activity observed with the fusion proteins were comparable or slightly better than the wt Apo A-1 protein across the concentration range tested indicating the absence of any major adverse effects due to albumin sequence in the final trans-spliced product on Apo A-1 function. These results provide strong evidence about the effectiveness of the compositions of the present invention for the production of functional biologically active proteins in vivo.

Example 7

High Capacity Screens for Isolation of Optimal Binding Domains for Albumin Targets A high capacity screen (HCS) to identify optimal binding domains for mouse albumin pre-mRNA target was performed as described before (U.S. patent application Ser. No. 10/693,192, filed Oct. 24, 2003) (FIG. 24A) with various modifications (FIG. 24B).

High Capacity Screen Pre-mRNA Target

Mouse albumin intron 1 and exon 2 comprising of nucleotides 114 through 877 total of 763 bp (Ref. seq. NC_000071) (FIG. 25) was PCR amplified using the genomic DNA and

```
primers mAlb15
                                      (SEQ ID NO: 21)
(5'- CTAG GGATCC GTTTTATGTTTTTTCATCTCTG)
and mAlb8
                                      (SEQ ID NO: 22)
(5'- CTAG GCGGCCGC AGGCCTTTGAAATGTTGTTCTCC).
```

The PCR product was then digested with Bam HI and Not I (indicated in bold) and cloned into an existing HCS target plasmid to generate pc5'zsG-mIn1-Ex2 plasmid (FIG. 26). Stable cells expressing the 5' half of the coding sequence for the green fluorescent protein (GFP) (zsGreen from Clontech) coupled to intron 1 and exon 2 of mouse albumin gene was established in 293 cells by transfecting the target plasmid followed by hygromycin selection. After 2 weeks of selection, hygromycin resistant clones were pooled, characterized by RT-PCR and used for HCS.

Mouse Albumin PTM Binding Domain Library

The mouse albumin sequence comprising intron 1 and exon 2 was PCR amplified using genomic DNA and primers as described above, digested with Bam HI and Not I and ligated to generate a large concatemerized fragment (~10 kb). This step was introduced to increase BD complexity. The concatemerized DNA was then fragmented into small pieces by sonication and fractionated on a 3% agarose gel. Fragment size ranging from 50-250 nucleotides were gel purified, ends were repaired using Klenow enzyme and cloned into PTM cassette described before (U.S. patent application Ser. No. 10/693,192, filed Oct. 24, 2003) (FIG. 27).

PCR analysis of the library colonies showed >87% recombination efficiency and produced a complex library with >$10^6$ independent clones with BDs varying in size from 50-250 nts (FIG. 28). The primary library was amplified in bacteria and used for screening the optimal BDs by HCS.

PTM Selection Strategy

Following the FACS-based PTM selection strategy described before (U.S. patent application Ser. No. 10/693,192, filed Oct. 24, 2003), a mAlb binding domain (BD) library using the assay cells expressing the 5'zsG-mIn1-Ex2 pre-mRNA target was tested. (See FIG. 24B)

Briefly, on day 1, COS-7 cells were plated and transfected with 5'zsG-mIn1-Ex2 target plasmid using Lipo2000 reagent. On day 2, ~$10^6$ independent PTM clones were delivered to assay cells expressing 5'zsG-mIn1-Ex2 pre-mRNA as protoplasts. As illustrated in the FIG. 29, cells were sorted after 24 hr by FACS, and cells expressing high GFP and proportionate RFP were collected in 2 fractions i.e., high green (HG) and low green (LG) fractions, instead of a single fraction as previously described. PTMs from the collected cells were rescued by HIRT DNA extraction followed by EcoR V digestion to reduce target plasmid contamination in the final HIRT DNA preparation. About 40 binding domain containing PTMs from LG and HG fractions were initially tested by parallel transfection. Trans-splicing efficiency of these PTMs was assessed by FACS analysis.

As predicted, the percent GFP positive (GFP$^+$) cells and the mean GFP fluorescence was higher in PTMs from HG fraction compared to LG fraction with a 2:1 ratio (FIG. 29).

A hundred more BD containing clones from HG fraction was isolated and tested by parallel transfection and the results are summarized in FIG. 30. GFP mean fluorescence was used as an indicator for assessing trans-splicing efficiency of the individual PTMs. Based on the GFP mean fluorescence, the trans-splicing efficiency of the majority of the PTMs selected from the HCS were either similar or slightly higher than the rationally designed model PTM (FIG. 30). However, several PTMs with considerably higher (1.5 to 2-fold) trans-splicing compared with the model PTM were present. In the current screen, a ratio of 1:20 of superior PTMs vs. the rest was obtained.

From this step, the top 20 PTMs were selected for further characterization by parallel transfection followed by molecular analysis using reverse transcription (RT) real time quantitative PCR (RT-qPCR) for specific trans-splicing and the results are summarized in FIG. 31. Total RNA was isolated and trans-splicing efficiency was measured by RT-qPCR. Target and PTM specific primers were used for measuring specific trans-splicing, and total splicing was measured using primers specific for the 5'zsG exon as previously described. Based on the qPCR or GFP mean fluorescence values up to ~5-10 fold enrichment (after normalization) for trans-splicing efficiency was detected with PTMs selected from the HCS compared to a rationally designed model PTM (FIG. 31). Similar results, i.e. enhancement in trans-splicing efficiency, was observed with the enriched library (LG and HG samples) compared with the starting library, which is consistent with previous screen.

The effect of BD orientation and sequence position on trans-splicing efficiency and specificity was also analyzed. The sequence of random clones from the starting PTM library were compared with the enriched library i.e., PTMs selected after one round of enrichment.

Sequence analysis of the PTMs from the starting library revealed that ~51% of the BDs were in correct (antisense) orientation compared to 49% incorrect orientation. The BD size varied from 40 nt and up to 336 nt and also showed good distribution indicating the complexity of the mAlb BD library. In contrast, sequence analysis of the PTMs selected from the enriched library, as expected, showed an increase in correct orientation BDs (88%) and the mean BD length was significantly higher than the starting library, which is consistent with previous work demonstrating that longer BDs are more efficient (Puttaraju et al., 2001).

Example 8

Trans-Splicing of Human Apolipoprotein Apo A-1 in Cells Human Apolipoprotein (Apo A-1) PTM Detailed structure of a human Apolipoprotein A1 (Apo A-1) PTM used in this example to show proof of principle is shown in FIG. 32. The PTM cassette consists of a trans-splicing domain (TSD) that include unique restriction sites, NheI and SacII, for cloning the lead binding domains (BDs), a 24 nucleotide spacer region, a strong 3' splice site including the consensus yeast branch point (BP), an extended polypyrimidine tract (19 nucleotides long), a splice acceptor site (CAG dinucleotide) followed by the majority of the coding sequence for wild type human Apo A-1 mRNA from nt 118 through nt 842 (Ref seq. NM_000039 and as shown in FIG. 34). The PTM cassette also contains the SV40 polyadenylation site and woodchuck hepatitis post-transcriptional regulatory element (WPRE) to enhance the stability of trans-spliced message. The entire cassette is cloned into pcDNA3.1 vector backbone, which contains cytomegalovirus promoter (Invitrogen). In addition, the vector backbone was further modified to include Maz4 (transcriptional pause site) sequence to reduce cryptic cis-splicing between vector ampicillin gene and PTM 3' splice site. PTMs used for functional studies mAlbPTM97C2 and mAlbPTM158 were generated by cloning 279 bp and 149 bp BD sequence into the PTM cassette between NheI and SacII sites and were verified by sequencing.

Mouse Albumin Minigene Target Pre-mRNA

For demonstrating in vitro Apo A-1 function, a mouse albumin mini-gene target consisting of exon 1, intron 1 and exon 2 was used. A schematic diagram of the pre-mRNA target is shown in FIG. 33. The mouse albumin coordinates are as described in Ref Seq. NC_000071. The mouse albumin Ex1-In1-Ex2 pre-mRNA target (mAlbEx1-In1-Ex2) constructed as follows: 877 bp fragment corresponding to nucleotides 1 through 877 was PCR amplified using the following mouse genomic DNA and primers: mAlb-Ex1F (SEQ ID NO:23) (5'-ctagGCTAGC ACCTTT CCTATCAAC-CCCACTAGC) and mAlb8 (SEQ ID NO:24) (5'-ctagGCG-GCCGC AGGCCTTTGAAATGTTGTTCTCC). These primers contain unique restriction sites at the end of the fragment (indicated in bold). The PCR product was digested with Nhe I and Not I and cloned into inducible expression vector pcDNA5/FRT/TO designed to use with Flip-In T-Rex system (Invitrogen). The final construct (pcDNATOfrt-mAlbEx1-In1-Ex2) contains the following features: CMV promoter, Tet operator, SV40 polyadenylation site and hygromycin selection marker for establishing stable cell lines.

Generation of a Stable Cell Line Expressing Albumin Target

Using the target plasmid described above, a stable target cell line that expressed the mouse albumin mini-gene target consist of exon 1, intron 1 and exon 2 was generated. Analysis of total RNA from cells transfected with target plasmid (pcD-NATOfrt-mAlbEx1-In1-Ex2) by RT-PCR produced the expected cis-spliced product, but no albumin protein. Upon confirming the splicing pattern of mouse albumin mini-gene target pre-mRNA, a stable cell line in Flip-In T-Rex 293 cells was established by transfecting the target plasmid followed by hygromycin selection. After selecting for a period of ~2 weeks, hygromycin resistant clones were pooled and maintained in hygromycin until used.

Efficient Trans-Splicing of Human Apo A1 PTMs

Human Apo A-1 PTMs selected from the HCS shows efficient and accurate trans-splicing to mouse albumin pre-mRNA in stable cells. PTM mediated trans-splicing and production of mouse albumin-human Apo A-1 chimeric mRNA was evaluated by transfecting stable cells with mAlbPTM97C2 and mAlbPTM158, along with a splice mutant lacking the TSD (splice incompetent PTM) and mock transfection. Total RNA isolated from these cells was analyzed by RT-PCR using mouse albumin target and human Apo A-1 PTM specific primers. These primers produced the predicted 390 bp product only in cells that received functional PTMs (FIG. 35, lanes 2-4 and 6). No such product was detected in cells transfected with the splice mutant or in mock transfection (FIG. 35, lane 1 and 5). The PCR product was purified and was directly sequenced, confirming the precise trans-splicing to the predicted splice sites of the PTM and the target pre-mRNA in stable cells (FIG. 35).

Real-time quantitative RT-PCR was used to quantify the fraction of mouse albumin pre-mRNA transcripts converted into chimeric mRNAs by PTMs. Primers for real-time qPCR were designed to discriminate between target exon 1 and trans-spliced mRNAs. Using the protocols described previously, trans-splicing efficiency of mAlbPTM97C2 and mAlbPTM158 was quantified.

Mouse albumin specific PTMs 97C2 and 158 showed a trans-splicing efficiency of 5.6% and 3.45%, respectively. These data confirmed robust trans-splicing between mouse albumin mini-gene target pre-mRNA and PTMs in stable cells.

Trans-Splicing and Production of Full-Length Protein

The PTM-mediated trans-splicing was assessed for the ability to produce full-length mouse albumin-human Apo A-1 fusion protein in stable cells. Briefly, assay cells expressing the mouse albumin mini-gene pre-mRNA was transfected with mAlbPTMs (97C2 and 158), human albumin-Apo A-1 fusion as a positive control, and splice mutant with a point mutation (G>T) at splice junction as a negative control. Cells were washed after 5 hrs with serum free media and incubated with advanced DMEM serum free media. After 48 hrs, the media was collected, concentrated and analyzed by Western blot. Production of full-length human Apo A-1 protein was demonstrated using anti-human Apo A-1 antibody as described above.

Accurate trans-splicing between mouse albumin exon 1 and PTM would result in a 28 kDa albumin-human Apo A-1 fusion protein. Trans-splicing mediated production of full-length mature human Apo A-1 protein is evident in cells transfected with functional PTMs (97C2 and 158) (FIG. 36, lanes 2-3) but not in controls i.e., cells transfected with a splice mutant or in mock (FIG. 36, lanes 4-5) and it also co-migrated with the albumin-Apo A-1 fusion protein produced using cDNA control plasmid (FIG. 36, lane 1-3). These studies again confirmed precise trans-splicing between the mouse albumin exon 1 and human Apo A-1 PTMs, resulting in the production of fusion albumin-human Apo A-1 protein in stable cells.

Example 9

Trans-Splicing to Endogenous Mouse Albumin Pre-mRNA in Mice

The efficacy of the lead PTMs selected from the high capacity screen (HCS) were evaluated in vivo. Fifty micrograms of mAlbPTM97C2 (PTM only) or 20 µg of mouse albumin mini-gene target plus 30 µg of mAlbPTM97C2 plasmids were mixed with jet-PEI-Gal (Q-Biogen) reagent and injected via tail vein into normal C57BL/6 mice. Liver and serum samples were collected at 24 and 48 hrs time points. Total and poly A mRNA was isolated and analyzed by RT-PCR using mouse albumin exon 1 specific and human Apo A-1 PTM specific primers.

Trans-splicing was detected in a single round in mice that received both mini-gene target plus PTM plasmids, as well as in mice that received PTM only (FIG. 37, lane 3, 8 & 9). Each positive RT-PCR product was purified and sequenced demonstrating the precise trans-splicing of mouse albumin exon 1 into human Apo A-1 coding sequence at the predicted splice sites (FIG. 37, lower panel). These results demonstrated accurate trans-splicing between the PTM and the endogenous albumin pre-mRNA target in mice and further validated albumin targeting strategy in vivo.

FIG. 38 describes a strategy to increase ApoA1 expression by targeting to human albumin sequences. FIG. 39 describes various means of eliminating albumin sequences in the final trans-spliced product, i.e. to produce a trans-spliced product that is identical to the wild type human ApoA1 without any albumin sequence.

For example, the current albumin trans-splicing strategy results in the production of chimeric mRNA and protein. The final trans-spliced product contains 7 nucleotides or 2 amino acids from albumin target mRNA. For human applications it may be desirable to eliminate the albumin sequence in the final product to preclude immunological reactions. In one exemplary strategy, illustrated in FIG. 40, the PTM will be engineered to encode "Furin" like endopeptidase (or proprotein convertase) cleavage site which has been used to express proteins in vivo (Fuller R S, Brake A J, Thorner J, *Science,* 246: 482-486, 1989; Bresnahan P A, Leduc R, Thomas L, Thorner J, Gibson H L, Brake A J, Barr P J, Thomas G., *J Cell Biol.* 111:2851-2859, 1990; van de Ven W J, Voorberg J, Fontijn R, Pannekoek H, van den Ouweland A M, van Duijnhoven H L, Roebroek A J, Siezen R J, *Mol Biol Rep.* 14:265-75, 1990; Duckert P, Brunak S, Blom N. *Protein Eng Design & Selection.* 17:107-112, 2004). In another example, the PTM will be designed to include the protein's own native secretion signal, i.e., "pre-pro" signal (if it has one). This strategy was designed to take advantage of the endogenous native cellular machinery to enhance recognition, processing and secretion of the final trans-spliced protein to the site of action similar to wild type protein. For example, trans-splicing of PTM into albumin pre-mRNA target produces a chimeric mRNA and pre-pro-protein that in addition to signal peptide cleavage in rough endoplasmic reticulum undergoes several post-translational modifications in other cellular compartments and, finally, endopeptidase cleavage resulting in the release of a mature, fully processed biologically active protein that is identical to the wild type. (FIG. 41).

Example 10

In Vitro and In Vivo Production of Recombinant Proteins by Trans-Splicing into Highly Abundant Transcripts Three examples of in vivo protein production as a result of trans-splicing into albumin pre-mRNA have been demonstrated. The first is production of human ApoA-I. These studies have shown that human ApoA-I was produced in mice as evidenced by gene expression and secretion (FIG. 42), identification of ApoA-I by Western blot analysis (FIG. 43), and functionality as determined by cholesterol efflux assays (FIG. 44). More appropriately, this in vivo production of human ApoA-I resulted in an increase of HDL in three separate experiments, each experiment increasing HDL by 20-25 mg (FIG. 45).

As a second example, gene sequences for a single chain antibody were encoded in the PTM and delivered by plasmid. In these studies, a single chain monoclonal antibody directed against E7 of human papillomavirus (HPV) was utilized. Results showed that the antibody was expressed and secreted (FIG. 49). In addition, this in vivo trans-spliced product was effective in inhibiting the growth of HPV-infected cells (FIG. 50). This study effectively reproduced the results of Wang-Johanning et al. (Cancer Research 58:1893-1900, 1998). These results address the challenge of monoclonal antibody commercialization: cost of production and achieving therapeutic levels on antibodies in the plasma, on the order of 3-30 ug/ml, as reviewed by Bakker et al. (J. Mol. Ther. 10:411-416, 2004).

In a third example, a PTM targeting intron one of mouse albumin and encoding mouse Factor VIII was administered intravenously to Factor VIII knockout mice as shown in FIG. 46. These mice have essentially zero Factor VIII levels in their plasma. Results of initial studies are shown in FIG. 47 and demonstrate significant production of Factor VIII. Uninoculated controls as well as animals that received a PTM that were defective in splicing showed no Factor VIII. (See FIG. 47) In subsequent studies, animals were inoculated with both albumin minigene target and the PTM encoding Factor VIII and these animals demonstrated significant plasma levels of Factor VIII (FIG. 48). As a control, the Factor VIII minigene was used. Use of the albumin pre-mRNA was significantly better than the Factor VIII target.

Additionally, the relative levels of mouse Factor VIII pre-mRNA and mouse albumin pre-mRNA were determined. The results are shown in FIG. 51 and illustrate that the levels of albumin pre-mRNA are 270× more abundant than Factor VIII transcript, demonstrating the validity of trans-splicing into a highly abundant transcript. In each of these three studies, the PTM utilized the same binding domain, that of mouse albumin. The PTMs utilized three respective coding domains: human ApoA-I, mouse Factor VIII and a single chain monoclonal antibody against HPV. It has also been shown that the PTM encoding the single chain monoclonal antibody trans-splices specifically into the precise nucleotide sequence in mouse albumin pre-mRNA (FIG. 52). It has also been separately shown that the same binding domain that encodes human ApoA-I also specifically trans-splices into the same nucleotide of the target (not shown).

This data demonstrate that PTMs targeting a highly abundant pre-mRNA can produce significant and therapeutic levels of recombinant proteins in vitro and in vivo and, as shown in the case of Factor VIII, can produce significantly higher plasma levels of protein than trans-splicing into homologous targets.

Example 11

In Vitro Trans-Splicing of Human apoAI into Mouse Albumin Pre-mRNA: Functionality of the Product The function of the human apoAI protein produced through trans-splicing of human apoAI into mouse albumin pre-mRNA has been evaluated in vitro. This was assessed by measuring, ATP-binding cassette transporter protein (ABC1) mediated, transfer of cellular cholesterol into apoAI acceptor. The release of radio-labeled cellular cholesterol to lipid free human apoAI was quantified and the efflux values obtained with trans-spliced protein were compared with that from wild type human apoAI protein. Human embryonic kidney cells (HEK293) were transfected with mouse albumin PTM (mAlbPTM97C2) containing either: the apoAI natural 3'UTR+bovine growth hormone poly A signal (BGH pA); or WPRE 3'UTR+SV40 poly A signal (SV40 pA) along with mouse albumin mini-gene targets (FIG. 53). 48 hrs post-transfection, supernatant was collected, concentrated and assayed for cholesterol efflux. HeLa cells transfected with ABC1 plasmid and HeLa control cells were grown to near confluency. Cells were then loaded with 1 µCi/ml $^3$H cholesterol. After equilibrating for 24 hrs, the cells were washed and incubated with media containing the trans-spliced human apoAI protein (supernatant from HEK293 cells transfected with PTM+target or cDNA control plasmid that mimics trans-splicing) or with different concentrations (2.5 µg, 5 µg, or 10 µg) of wild type purified apoAI protein as positive control. Cells were then allowed to efflux for 18 hrs. After the efflux period, medium was collected and an aliquot was then counted by liquid scintillation counting. The remaining counts in the cell fraction were determined after an over night extraction with isopropanol. The percent efflux was calculated by dividing the counts in the efflux media by the sum of the counts in the medium plus the cell fraction. DMEM/BSA medium was used as a blank and was subtracted from the radioactive counts obtained in the presence of an acceptor in the efflux media. As shown in FIG. 54, the amount of ABC1-mediated efflux observed with trans-spliced protein was significantly above the background and was similar to that of wt apoAI produced from control cDNA plasmid. The above described results indicate (a) that human apoAI protein produced through trans-splicing is functional and (b) the absence of adverse effects due to albumin sequence in the final trans-spliced mRNA on apoAI function.

Trans-splicing efficiency at the RNA level was quantified by real time RT-PCR (qRT-PCR) and the results are shown in FIG. 55. Based on qRT-PCR results it is clear that both PTMs, i.e., PTM with apoAI natural 3'UTR plus bovine growth hormone (BGH) poly A signal (new PTM) and the PTM with WPRE 3'UTR plus SV40 pA signal (old PTM), showed similar trans-splicing efficiency at the RNA level. The accuracy of trans-splicing was confirmed by direct sequencing of the RT-PCR product.

Example 12

In Vivo Trans-Splicing of Human apoAI into Mouse Albumin Pre-mRNA

Trans-splicing to an endogenous mouse albumin pre-mRNA target has been shown to produce human apoAI protein and HDL in mice. In particular, to verify the efficacy of the lead PTMs selected from high capacity screen (HCS) and to demonstrate trans-splicing of PTM into endogenous mouse albumin target followed by production of human apoAI protein, the following experiment has been performed. Fifty micrograms of: mAlbPTM97C2 (PTM only); 30 µg of PTM+ 15 µg of mini-gene target (additional target plasmid to increase pre-mRNA concentration); or 20 µg of control cDNA plasmid that mimic trans-spliced mRNA were hydrodynamically injected via the tail vein into normal C57BL/6 mice. Liver and serum samples were collected at 8, 16, 24 and 48 hrs time points. Total and polyA mRNA was isolated and analyzed by end point RT-PCR using mouse albumin exon 1 specific (SEQ ID NO:25) (ACCTTTCTCCTCCTCCTCT-TCGT) and human apoAI PTM specific primers (SEQ ID NO:26) (ACATAGTCTCTGCCGCTGTCTTT). As shown in FIG. 56A the presence of trans-spliced chimeric mRNA was detected in 11 out of 14 mice that were injected with cDNA control plasmid, indicating good delivery of the plasmid DNA. Next, PTM trans-splicing to endogenous mouse albumin pre-mRNA target was evaluated using the target and PTM specific primers as described above. Trans-splicing between mouse albumin target pre-mRNA and PTM was readily detected in a single round of PCR with 1 µg of total RNA and 25 cycles of amplification. All samples from mice that received both the mini-gene target and the PTM plasmids were positive for trans-splicing (FIG. 56B). In comparison, 10 out of 13 mice were positive for trans-splicing that received the PTM only (FIG. 56C). Each positive RT-PCR product was purified and sequenced demonstrating precise trans-splicing of human apoAI coding sequence into mouse albumin exon 1 at the predicted splice sites. These results demonstrate accurate trans-splicing between the PTM and the endogenous albumin pre-mRNA target in mice and further validate albumin targeting strategy for the production of therapeutic proteins in vivo.

In addition, accurate trans-splicing to the endogenous mouse albumin pre-mRNA target to produce human apoAI protein in mice was demonstrated. Serum samples were collected from mice injected with PTM only, PTM+target and cDNA for the production of human apoAI protein were tested by Western blot. Approximately, 20-50 µl serum was passed through ProteoPrep™Blue affinity column (Sigma-Aldrich, Product Code PROT BA). This step was introduced to eliminate albumin and IgGs which make up greater than 70% of the proteins in serum and to increase sample loads to better visualize lower abundant proteins. Samples separated by 12% SDS-PAGE were transferred to nitrocellulose membranes and probed with a human specific apoAI monoclonal antibody (Biodesign International, Cat #H45625M). Proteins were visualized by a chemiluminescence kit (Invitrogen, Cat #WB7103). Western blot results indicated the appearance of human apoAI protein as early as 16 hrs post-injection in mice injected with cDNA control plasmids. In this group, 7 out of 14 samples were positive for human apoAI protein. (FIG. 57A). In mice that received both target and PTM, 5 out of 6 samples were positive for human apoAI protein. In mice that received the PTM only (targeting endogenous target), 4 out of 10 samples were positive for human apoAI protein. These results demonstrate the accurate trans-splicing of human apoAI sequence into endogenous mouse albumin exon 1 leading to the production of human apoAI protein (FIG. 57B).

Example 13

In Vivo Trans-Splicing of Minicircle Vector DNA for Expression of Human apoAI Protein Minicircles are DNA vectors that lack the bacterial DNA sequence that is implicated in the silencing of gene expression in vivo. See, for example, Chen Z Y, He C Y, Ehrhardt A, Kay M A. (2003) DNA vectors devoid of bacterial DNA result in persistent and high-level transgene expression in vivo. *Mol Ther.* 8:495-500; Chen Z Y, He C Y, Meuse L, Kay M A. (2004) Silencing of episomal transgene expression by plasmid bacterial DNA elements in vivo. *Gene Ther.* 11:856-864 the disclosures of which are hereby incorporated by reference.

Minicircles were tested by cloning the mAlbPTM97C2 expression cassette into minicircle vector. Fifty to seventy five micrograms of mAlbPTM97C2 (functional PTM), mAlbPTM97C2-splice mutant (defective PTM) or control cDNA (mimics trans-spliced mRNA) in the form of minicircles were hydrodynamically injected via tail vein into normal C57BL/6 mice. Liver and serum samples were collected at 48 hrs through 4 week time points. RNA analysis by qRT-PCR using mouse albumin exon 1 specific forward primer and human apoAI specific reverse primer confirmed the trans-splicing of mouse albumin PTM into endogenous mouse albumin pre-mRNA target. As shown in Table 1, the results obtained with a splice mutant PTM were similar to background observed in the mock group. The presence of trans-spliced mRNA was readily detected at 4 week post-injection indicating minicircles can be used as a non-viral PTM delivery system.

Western blot analysis of serum samples from mice injected with minicircles encoding the PTM confirmed the production of human apoAI protein through trans-splicing. Ten to fifty micro liter serum samples were immunoprecipitated using human specific apoAI antibody. After elution, samples were concentrated, analyzed on a 12% SDS-PAGE and probed with the same antibody (human specific apoAI antibody) that was used for immunoprecipitation. The blot was developed using an ECL kit (Invitrogen, Cat #WB7104). Western results clearly showed the presence of a 28 kDa protein band that co-migrated with the positive control purified apoAI protein (FIG. 58A). The presence of human apoAI protein was also detected in 4 week serum samples (FIG. 58B). These results not only confirmed the production of human apoAI protein through trans-splicing of PTM into endogenous mouse albumin pre-mRNA target in mice, but also demonstrated the utility of minicircles as a non-viral PTM delivery system.

TABLE 1

Trans-splicing in mice - qRT-PCR Results

| Group | Mouse ID | Weight | Injection remarks | time | nor-TS |
|---|---|---|---|---|---|
| A. Mock | 4 | 21.9 | ok | 48 h | 1.18E+00 |
| B. SM, 50 ug | 6 | 19.2 | 1.8 ml | 48 h | 1.48E+00 |
|  | 9 | 18.6 | 1.7 ml |  | 2.07E+00 |
|  | 10 | 19.6 | 1.7 ml |  | 5.70E+00 |
| B. SM, 50 ug | 1 | 19.4 | 1.8 ml, slow recovery | 4 wk | 1.48 |
|  | 2 | 18.5 | 1.8 ml, B |  | 2.07 |
|  | 7 | 18.3 | 1.8 ml |  | 5.70 |
| C. PTM, 75 ug | 11 | 22.1 | 1.8 ml, B | 48 h | 1.89E+00 |
|  | 12 | 19.7 | 1.7 ml, Brett tried, Jun completed |  | 9.42E+01 |
|  | 13 | 21.8 | 1.8 ml, B |  |  |
|  | 15 | 16.9 | 1.6 ml |  | 1.35E+03 |
|  | 16 | 20.2 | 1.8 ml |  | 1.29E+02 |
| C. PTM, 75 ug | 17 | 18.3 | 1 ml | 1 wk | 2.18 |
|  | 18 | 18.5 | 1.8 ml, B |  | 1.09 |
|  | 19 | 18.6 | 1.6 ml |  | 31.50 |
|  | 20 | 20.1 | 1.7 ml |  | 188.71 |
|  | 25 | 20.9 | 1.8 ml |  | 44.55 |

TABLE 1-continued

Trans-splicing in mice - qRT-PCR Results

| Group | Mouse ID | Weight | Injection remarks | time | nor-TS |
|---|---|---|---|---|---|
| C. PTM, 75 ug | 21 | 18.9 | 1.7 ml | 2 wk | 47.84 |
|  | 22 | 17.4 | 1.6 ml |  | 64.03 |
|  | 23 | 19.9 | 1.7 ml |  |  |
|  | 24 | 20.1 | 1.7 ml, B several attemps |  | 1.40 |
|  | 28 | 18.6 | 1.7 ml, B |  |  |
| C. PTM, 75 ug | 26 | 18.2 | 1.7 ml, B | 4 wk | 0.19 |
|  | 27 | 19.6 | 1.7 ml |  | 25.92 |
|  | 29 | 21.3 | 1.8 ml, B |  | 1.33 |
|  | 30 | 16.5 | 1.5 ml |  | 3.93 |
|  | 35 | 19.4 | 1.7 ml |  | 7.25 |
| D. mAlb-hAI cDNA, 50 ug | 42 | 18.9 | 1.7 ml | 48 h | 1.53E+05 |
|  | 43 | 18.4 | 1.7 ml, B |  | 1.25E+05 |
|  | 44 | 15.4 | 1.5 ml |  | 8.56E+05 |
|  | 46 | 20.2 | 1.8 ml, B | 4 wk | 9.2E+03 |
|  | 47 | 22.2 | 1.8 ml, B 3 hrs later |  | 4.6E+03 |
|  | 48 | 18.1 | 1.7 ml |  | 9.8E+01 |

Example 14

In Vivo Trans-Splicing of Human apoAI PTM into Mouse Albumin Pre-mRNA Increases High-Density Lipoprotein (HDL)

One of the main objectives of the current study is to determine whether production of human apoAI protein through trans-splicing contributes to HDL increase in vivo. To test this, mice were injected with mouse albumin PTM (PTM only) and control cDNA plasmid (mimics trans-spliced mRNA), as described above. Serum samples were collected at different time points (48 hrs through 4 weeks) and total HDL-cholesterol was determined by dextran sulfate precipitation method and the results were compared with controls. Specifically, 12 μl of serum was mixed with 4 μl dextran sulfate precipitation reagent plus 30 μl saline and, after 10 min at room temperature, was centrifuged for 30 min (4° C.) at 12,000 rpm. The clear supernatant (40 μl) was mixed with 169 μl saline and total cholesterol was measured using FPLC. The baseline total HDL-cholesterol in the control group averaged to about 60 mg/dL. At 48 hrs time point, ~25% increase in total HDL-cholesterol was observed in the control cDNA group that expresses an mRNA that is identical to trans-spliced mRNA. In contrast, no significant increase was observed in the PTM group at 48 hrs. However, as shown in FIG. 59, significant increases (25-50%) in total HDL-cholesterol was observed in serum samples collected at 1, 2 and 4 week time points in mice treated with PTM only and also mice treated with cDNA. Accordingly, the results presented in this application clearly show: (a) successful and accurate trans-splicing of mouse albumin PTM into mouse albumin target pre-mRNA, (b) production of human apoAI protein through trans-splicing and, most importantly, (c) production of human apoAI protein through trans-splicing in mice leads to significant (25-50%) increase in HDL level over the baseline. Increases in HDL blood levels are associated with reduced risk of cardiovascular disease. Numerous reports have indicated that "increasing the HDL cholesterol level by 1 mg may reduce cardiovascular risk by 2-3 percent (Castelli W P. Cholesterol and lipids in the risk of coronary artery disease—the Framingham Study. Can J Cardiol 1988; 4 [Suppl A]:5-10A; Third Report of the National Cholesterol Education Program [NCEP] Expert Panel on Detection, Evaluation and Treatment of High Blood Cholesterol in Adults [Adult Treatment Panel III]. Final Report. Bethesda [Md.]: National Cholesterol Education Program, National Heart, Lung, and Blood Institute, National Institutes of Health; September 2002. NIH Publication 02-5215. Brewer B H, 2004, *Am Heart J,* 148, S14-S18; Brewer B H, 2004, *N Engl J Med,* 350, 1491-1494)

The present invention also provides a pack or kit comprising one or more containers filled with one or more of the ingredients of the compositions of the invention. The pack or kit may include a notice in the form prescribed by a governmental agency regulating the manufacture, use or sale of pharmaceuticals or biological products, which notice reflects approval by the agency of manufacture, use or sale for human administration.

The present invention is not to be limited in scope by the specific embodiments or examples described herein. Indeed, various modifications of the invention in addition to those described herein will become apparent to those skilled in the art from the foregoing description and accompanying Figures. Such modifications are intended to fall within the scope of the appended claims. Various references are cited herein, the disclosure of which are all hereby incorporated by reference in their entireties.

We claim:

1. An isolated cell comprising a nucleic acid molecule that encodes a protein or polypeptide of interest wherein said nucleic acid molecule comprises:
   a) one or more target binding domains that target binding of the nucleic acid molecule that encodes the protein or polypeptide of interest to an abundantly expressed target pre-mRNA within the cell, wherein said nucleic acid molecule is recognized by nuclear splicing components within the cell and wherein the abundantly expressed target pre-mRNA is selected from the group consisting of pre-mRNAs encoding albumin, casein, myosin and fibroin;
   b) a splice region;
   c) a spacer region that separates the splice region from the target binding domain; and
   d) a nucleotide sequence encoding the a protein or polypeptide of interest to be trans-spliced to the target pre-mRNA;
   wherein said nucleic acid molecule encodes a polypeptide of interest heterologous to the target pre-mRNA.

2. The isolated cell of claim 1 wherein the protein or polypeptide of interest is selected from the group consisting of cytokines, growth factors, insulin, hormones, enzymes and antibody polypeptides.

3. The isolated cell of claim 1 wherein the protein or polypeptide of interest is selected from the group consisting of ApoA1 and ApoA1 milano variant.

4. The isolated cell of claim 1 wherein the protein or polypeptide of interest comprises a single chain antibody polypeptide.

5. The isolated cell of claim 1 wherein the protein or polypeptide of interest comprises Factor VIII protein.

6. An isolated nucleic acid molecule that encodes a protein or polypeptide of interest wherein said nucleic acid molecule comprises:
   a) one or more target binding domains that target binding of the nucleic acid molecule that encodes the protein or polypeptide of interest to an abundantly expressed target pre-mRNA within the cell, wherein said nucleic acid molecule is recognized by nuclear splicing components within the cell and wherein the abundantly expressed target pre-mRNA is selected from the group consisting of pre-mRNAs encoding albumin, casein, myosin and fibroin;
   b) a splice region;
   c) a spacer region that separates the splice region from the target binding domain; and
   d) a nucleotide sequence encoding the protein or polypeptide of interest to be trans-spliced to the target pre-mRNA;
   wherein said isolated nucleic acid molecule encodes a polypeptide of interest heterologous to the target pre-mRNA.

7. The isolated nucleic acid molecule of claim 6 wherein the protein or polypeptide of interest is selected from the group consisting of cytokines, growth factors, insulin, hormones, enzymes and antibody polypeptides.

8. The isolated nucleic acid molecule of claim 6 wherein the protein or polypeptide of interest is selected from the group consisting of ApoA1 and ApoA1 milano variant.

9. The isolated nucleic acid molecule of claim 6 wherein the protein or polypeptide of interest comprises a single chain antibody polypeptide.

10. The isolated nucleic acid molecule of claim 6 wherein the protein or polypeptide of interest comprises Factor VIII protein.

* * * * *

SEQUENCE LISTING

```
<160> NUMBER OF SEQ ID NOS: 46

<210> SEQ ID NO 1
<211> LENGTH: 8
<212> TYPE: RNA
<213> ORGANISM: Artificial
<220> FEATURE:
<223> OTHER INFORMATION: Chemically Synthesized

<400> SEQUENCE: 1 agguragu                                                               8

<210> SEQ ID NO 2
<211> LENGTH: 7
<212> TYPE: RNA
<213> ORGANISM: Artificial
<220> FEATURE:
<223> OTHER INFORMATION: Chemically Synthesized
<220> FEATURE:
<221> NAME/KEY: misc_feature
<222> LOCATION: (2)..(2)
<223> OTHER INFORMATION: n is a, c, g, or u

<400> SEQUENCE: 2 ynyurac                                                                7

<210> SEQ ID NO 3
<211> LENGTH: 258
<212> TYPE: DNA
<213> ORGANISM: Artificial
<220> FEATURE:
<223> OTHER INFORMATION: Chemically Synthesized

<400> SEQUENCE: 3
gtagttcttt tgttcttcac tattaagaac ttaatttggt gtccatgtct ctttttttt      60 ctagtttgta gtgctggaag gtattttgg agaaattctt acatgagcat taggagaatg    120
tatgggtgta gtgtcttgta taatagaaat tgttccactg ataatttact ctagtttttt   180
atttcctcat attattttca gtggcttttt cttccacatc tttatatttt gcaccacatt   240
caacactgta gcggccgc                                                  258

<210> SEQ ID NO 4
<211> LENGTH: 270
<212> TYPE: DNA
<213> ORGANISM: Artificial
<220> FEATURE:
<223> OTHER INFORMATION: Chemically Synthesized

<400> SEQUENCE: 4
```

```
ccaactatct gaatcatgtg ccccttctct gtgaacctct atcataatac ttgtcacact      60
gtattgtaat tgtctctttt actttcccct gtatcttttg tgcatagcag agtacctgaa     120
acaggaagta ttttaaatat tttgaatcaa atgagttaat agaatcttta caaataagaa     180
tatacacttc tgcttaggat gataattgga ggcaagtgaa tcctgagcgt gatttgataa     240
tgacctaata atgatgggtt ttatttccag                                      270
```

```
<210> SEQ ID NO 5
<211> LENGTH: 18
<212> TYPE: RNA
<213> ORGANISM: Artificial
<220> FEATURE:
<223> OTHER INFORMATION: Chemically Synthesized

<400> SEQUENCE: 5
gggcugauuu uuccaugu                                                    18

<210> SEQ ID NO 6
<211> LENGTH: 23
<212> TYPE: DNA
<213> ORGANISM: Artificial
<220> FEATURE:
<223> OTHER INFORMATION: Chemically Synthesized

<400> SEQUENCE: 6
taatacgact cactataggg aga                                              23

<210> SEQ ID NO 7
<211> LENGTH: 23
<212> TYPE: DNA
<213> ORGANISM: Artificial
<220> FEATURE:
<223> OTHER INFORMATION: Chemically Synthesized
<220> FEATURE:
<221> NAME/KEY: misc_feature
<222> LOCATION: (22)..(22)
<223> OTHER INFORMATION: n is a, c, g, or t

<400> SEQUENCE: 7
atttaggtga cactatagaa gng                                              23

<210> SEQ ID NO 8
<211> LENGTH: 23
<212> TYPE: DNA
<213> ORGANISM: Artificial
<220> FEATURE:
<223> OTHER INFORMATION: Chemically Synthesized

<400> SEQUENCE: 8
aattaaccct cactaaaggg aga                                              23

<210> SEQ ID NO 9
<211> LENGTH: 115
<212> TYPE: DNA
<213> ORGANISM: Artificial
<220> FEATURE:
<223> OTHER INFORMATION: Chemically Synthesized

<400> SEQUENCE: 9
gctagcatga agtgggtaac ctttctcctc ctcctcttcg tctccggctc tgcttttcc       60 aggggtgtgt ttcgccgaga agcacaggtc caactgcagg agtcaggggc tgagc          115

<210> SEQ ID NO 10
<211> LENGTH: 115
```

```
<212> TYPE: DNA
<213> ORGANISM: Artificial
<220> FEATURE:
<223> OTHER INFORMATION: Chemically Synthesized

<400> SEQUENCE: 10
gctcagcccc tgactcctgc agttggacct gtgcttctcg gcgaaacaca cccctggaaa    60
aagcagagcc ggagacgaag aggaggagga gaaaggttac ccacttcatg ctagc        115

<210> SEQ ID NO 11
<211> LENGTH: 28
<212> TYPE: DNA
<213> ORGANISM: Artificial
<220> FEATURE:
<223> OTHER INFORMATION: Chemically Synthesized

<400> SEQUENCE: 11
gctagcatgg cccaggtcca actgcagg                                       28

<210> SEQ ID NO 12
<211> LENGTH: 59
<212> TYPE: DNA
<213> ORGANISM: Artificial
<220> FEATURE:
<223> OTHER INFORMATION: Chemically Synthesized

<400> SEQUENCE: 12
aagctttcac ttgtcgtcat cgtctttgta gtcccgtttt atttccgctt ggtcccagc     59

<210> SEQ ID NO 13
<211> LENGTH: 23
<212> TYPE: DNA
<213> ORGANISM: Artificial
<220> FEATURE:
<223> OTHER INFORMATION: Chemically Synthesized

<400> SEQUENCE: 13
acctttctcc tcctcctctt cgt                                            23

<210> SEQ ID NO 14
<211> LENGTH: 22
<212> TYPE: DNA
<213> ORGANISM: Artificial
<220> FEATURE:
<223> OTHER INFORMATION: Chemically Synthesized

<400> SEQUENCE: 14
agtaagcaaa ccagtagccg tc                                             22

<210> SEQ ID NO 15
<211> LENGTH: 81
<212> TYPE: DNA
<213> ORGANISM: Artificial
<220> FEATURE:
<223> OTHER INFORMATION: Chemically Synthesized

<400> SEQUENCE: 15
atgaagtggg taacctttct cctcctcctc ttcgtctccg gctctgcttt ttccaggggt    60
gtgtttcgcc gagaagcacc c                                              81

<210> SEQ ID NO 16
<211> LENGTH: 82
<212> TYPE: DNA
<213> ORGANISM: Artificial
<220> FEATURE:
```

<223> OTHER INFORMATION: Chemically Synthesized

<400> SEQUENCE: 16
gggtgcttct cggcgaaaca caccccggga aaaagcagag ccggagacga agaggaggag    60
gagaaaggtt acccacttca tg                                            82

<210> SEQ ID NO 17
<211> LENGTH: 81
<212> TYPE: DNA
<213> ORGANISM: Artificial
<220> FEATURE:
<223> OTHER INFORMATION: Chemically Synthesized

<400> SEQUENCE: 17
atgaagtggg taacctttat ttccttctt tttctcttta gctcggctta ttccaggggt    60
gtgtttcgtc gagatgcacc c                                             81

<210> SEQ ID NO 18
<211> LENGTH: 82
<212> TYPE: DNA
<213> ORGANISM: Artificial
<220> FEATURE:
<223> OTHER INFORMATION: Chemically Synthesized

<400> SEQUENCE: 18
gggtgcatct cgacgaaaca caccccggga ataagccgag ctaaagagaa aagaaggga    60 aataaaggtt acccacttca tg                                            82

<210> SEQ ID NO 19
<211> LENGTH: 24
<212> TYPE: DNA
<213> ORGANISM: Artificial
<220> FEATURE:
<223> OTHER INFORMATION: Chemically Synthesized

<400> SEQUENCE: 19
ccccagagcc cctgggatcg agtg                                          24

<210> SEQ ID NO 20
<211> LENGTH: 42
<212> TYPE: DNA
<213> ORGANISM: Artificial
<220> FEATURE:
<223> OTHER INFORMATION: Chemically Synthesized

<400> SEQUENCE: 20
ctagaagctt cccactttgg aaacgtttat tctgagcacc gg                      42

<210> SEQ ID NO 21
<211> LENGTH: 32
<212> TYPE: DNA
<213> ORGANISM: Artificial
<220> FEATURE:
<223> OTHER INFORMATION: Chemically Synthesized

<400> SEQUENCE: 21
ctagggatcc gttttatgtt ttttcatctc tg                                 32

<210> SEQ ID NO 22
<211> LENGTH: 35
<212> TYPE: DNA
<213> ORGANISM: Artificial
<220> FEATURE:
<223> OTHER INFORMATION: Chemically Synthesized

<400> SEQUENCE: 22
ctaggcggcc gcaggccttt gaaatgttgt tctcc					35

<210> SEQ ID NO 23
<211> LENGTH: 34
<212> TYPE: DNA
<213> ORGANISM: Artificial
<220> FEATURE:
<223> OTHER INFORMATION: Chemically Synthesized

<400> SEQUENCE: 23
ctaggctagc acctttccta tcaaccccac tagc					34

<210> SEQ ID NO 24
<211> LENGTH: 35
<212> TYPE: DNA
<213> ORGANISM: Artificial
<220> FEATURE:
<223> OTHER INFORMATION: Chemically Synthesized

<400> SEQUENCE: 24
ctaggcggcc gcaggccttt gaaatgttgt tctcc					35

<210> SEQ ID NO 25
<211> LENGTH: 23
<212> TYPE: DNA
<213> ORGANISM: Artificial
<220> FEATURE:
<223> OTHER INFORMATION: Chemically Synthesized

<400> SEQUENCE: 25 accttctcc tcctcctctt cgt					23

<210> SEQ ID NO 26
<211> LENGTH: 23
<212> TYPE: DNA
<213> ORGANISM: Artificial
<220> FEATURE:
<223> OTHER INFORMATION: Chemically Synthesized

<400> SEQUENCE: 26
acatagtctc tgccgctgtc ttt					23

<210> SEQ ID NO 27
<211> LENGTH: 79
<212> TYPE: DNA
<213> ORGANISM: Artificial
<220> FEATURE:
<223> OTHER INFORMATION: Chemically Synthesized

<400> SEQUENCE: 27
atgaagtggg taacctttct cctcctcctc ttcgtctccg gctctgcttt ttccaggggt					60 gtgtttcgcc gagaagcac					79

<210> SEQ ID NO 28
<211> LENGTH: 79
<212> TYPE: DNA
<213> ORGANISM: Artificial
<220> FEATURE:
<223> OTHER INFORMATION: Chemically Synthesized

<400> SEQUENCE: 28
atgaagtggg taacctttct cctcctcctc ttcgtctccg gctctgcttt ttccaggggt					60

-continued

```
gtgtttcgcc gagaagcac                                              79

<210> SEQ ID NO 29
<211> LENGTH: 36
<212> TYPE: DNA
<213> ORGANISM: Artificial
<220> FEATURE:
<223> OTHER INFORMATION: Chemically Synthesized

<400> SEQUENCE: 29
atgcgagaag cacaggtcca actgcaggag tcaggg                           36

<210> SEQ ID NO 30
<211> LENGTH: 30
<212> TYPE: DNA
<213> ORGANISM: Artificial
<220> FEATURE:
<223> OTHER INFORMATION: Chemically Synthesized

<400> SEQUENCE: 30
atggcccagg tccaactgca ggagtcaggg                                  30

<210> SEQ ID NO 31
<211> LENGTH: 831
<212> TYPE: DNA
<213> ORGANISM: Artificial
<220> FEATURE:
<223> OTHER INFORMATION: Chemically Synthesized

<400> SEQUENCE: 31
atgaagtggg taacctttct cctcctcctc ttcgtctccg gctctgcttt ttccaggggt  60
gtgtttcgcc gagaagcaca ggtccaactg caggagtcag ggctgagct tgtgaagcct  120 ggggcttcag tgaagctgtc ctgcaaggct tctggctaca ccttcaccag ctactggatg  180
cactgggtga acagaggcc tggacatggc cttgagtgga ttggagagat tttacctgga  240
agtggtagta ctaactacaa tgagaagttc aagggcaagg ccacattcac tgcagataca  300
tcctccaaca cagcctacat gcaactcagc agcctgacat ctgaggactc tgccgtctat  360
tactgtgcaa gaggacgga cggctactgg tttgcttact ggggccaagg gaccacggtc  420
accgtctcct caggtggagg cggttcaggc ggaggtggct ctggcggtgg cggatcggac  480
atcgagctca ctcagtctcc agcaatcatg gctgcatctc aggggagaa ggtcaccatc  540 acctgcagtg tcagctcaag tataagttcc agcaacttgc actggtacca gcagaagtca  600
gaaacctccc ccaaaccctg gatttatggc acatccaacc tggcttctgg agtccctgtt  660
cgcttcagtg gcagtggatc tgggacctct tattctctca caatcagcag catggaggct  720
gaagatgctg ccacttatta ctgtcaacag tggagtagtt acccactcac gttcggtgct  780
gggaccaagc tggaaataaa acgggactac aaagacgatg acgacaagtg a           831

<210> SEQ ID NO 32
<211> LENGTH: 11
<212> TYPE: DNA
<213> ORGANISM: Artificial
<220> FEATURE:
<223> OTHER INFORMATION: Chemically Synthesized

<400> SEQUENCE: 32
tattaataca g                                                      11

<210> SEQ ID NO 33
<211> LENGTH: 77
```

```
<212> TYPE: DNA
<213> ORGANISM: Artificial
<220> FEATURE:
<223> OTHER INFORMATION: Chemically Synthesized

<400> SEQUENCE: 33
gctagcccgc ggacgatctc atattctatc gtcgaatact aacttttttt tttttttta      60 attaacagcc ccccaga                                                    77

<210> SEQ ID NO 34
<211> LENGTH: 23
<212> TYPE: DNA
<213> ORGANISM: Artificial
<220> FEATURE:
<223> OTHER INFORMATION: Chemically Synthesized

<400> SEQUENCE: 34
tttaattaac ataggtccaa ctg                                             23

<210> SEQ ID NO 35
<211> LENGTH: 6
<212> TYPE: DNA
<213> ORGANISM: Artificial
<220> FEATURE:
<223> OTHER INFORMATION: Chemically Synthesized

<400> SEQUENCE: 35 gctagc                                                                6

<210> SEQ ID NO 36
<211> LENGTH: 6
<212> TYPE: DNA
<213> ORGANISM: Artificial
<220> FEATURE:
<223> OTHER INFORMATION: Chemically Synthesized

<400> SEQUENCE: 36 ccgcgg                                                                6

<210> SEQ ID NO 37
<211> LENGTH: 45
<212> TYPE: DNA
<213> ORGANISM: Artificial
<220> FEATURE:
<223> OTHER INFORMATION: Chemically Synthesized

<400> SEQUENCE: 37
tactaactca attttttttt tttttttttt aattaacagg atgca                     45

<210> SEQ ID NO 38
<211> LENGTH: 79
<212> TYPE: DNA
<213> ORGANISM: Artificial
<220> FEATURE:
<223> OTHER INFORMATION: Chemically Synthesized

<400> SEQUENCE: 38
atgaagtggg taacctttct cctcctcctc ttcgtctccg gctctgcttt ttccaggggt     60
gtgtttcgcc gacaagcac                                                  79

<210> SEQ ID NO 39
<211> LENGTH: 209
<212> TYPE: DNA
<213> ORGANISM: Artificial
<220> FEATURE:
```

<223> OTHER INFORMATION: Chemically Synthesized

<400> SEQUENCE: 39

```
atggctcagt caaagcacgg tctaacaaaa gaaatgacaa tgaaataccg tatggaaggg      60
tgcgtcgatg gacataaatt tgtgatcacg ggagagggca ttggatatcc gttcaaaggg     120
aaacaggcta ttaatctgtg tgtggtcgaa ggtggaccat tgccatttgc cgaagacata    180
ttgtcagctg cctttatgta cggaaacag                                       209
```

<210> SEQ ID NO 40
<211> LENGTH: 703
<212> TYPE: DNA
<213> ORGANISM: Artificial
<220> FEATURE:
<223> OTHER INFORMATION: Chemically Synthesized

<400> SEQUENCE: 40

```
gtaagaaatc cattttctc ttgttcaact tttattctat tttcccagta aaataaagtt      60
ttagtaaact ctgcatcttt aaagaattat tttggcattt atttctaaaa tggcatagta    120
ttttgtattt tgtgaagtct tacaaggtta tcttattaat aaaattcaaa catcctaggt    180
aaaaaaaaaa aaaggtcaga attgtttagt gactgtaatt ttcttttgcg cactaaggaa    240
agtgcaaagt aacttagagt gactgaaact tcacagaata gggttgaaga ttgaattcat    300
aactatccca aagacctatt ccattgcact atgctttatt taaaaaccac aaaacctgtg    360
ctgttgatct cataaataga acttgtattt atatttattt tcattttagt ctgtcttctt    420
ggttgctgtt gatagacact aaaagagtat tagatattat ctaagttttg aatataaggc    480
tataaatatt taataatttt taaaatagta ttccttggtaa ttgaattatt cttctgttta    540
aaggcagaag aaataattga acatcatcct gagttttct gtaggaatca gagcccaata     600
ttttgaaaca aatgcataat ctaagtcaaa tggaaagaaa tataaaaagt aacattatta    660
cttcttgttt tcttcagtat ttaacaatcc tttttttct tcc                       703
```

<210> SEQ ID NO 41
<211> LENGTH: 67
<212> TYPE: DNA
<213> ORGANISM: Artificial
<220> FEATURE:
<223> OTHER INFORMATION: Chemically Synthesized

<400> SEQUENCE: 41

```
cttgcccaga caagagtgag gttgctcatc ggtttaaaga tttgggagaa gaaaatttca     60
aagcctt                                                               67
```

<210> SEQ ID NO 42
<211> LENGTH: 89
<212> TYPE: DNA
<213> ORGANISM: Artificial
<220> FEATURE:
<223> OTHER INFORMATION: Chemically Synthesized

<400> SEQUENCE: 42

```
gctagcccgc ggacgatctc atattctatc gtcgaatact aactcaattt tttttttttt     60 tttttaatt aacagccccc cagagcccc                                        89
```

<210> SEQ ID NO 43
<211> LENGTH: 897
<212> TYPE: DNA
<213> ORGANISM: Artificial

```
<220> FEATURE:
<223> OTHER INFORMATION: Chemically Synthesized

<400> SEQUENCE: 43
agagactgcg agaaggaggt cccccacggc ccttcaggat gaaagctgcg gtgctgacct      60
tggccgtgct cttcctgacg gggagccagg ctcggcattt ctggcagcaa gatgaacccc     120
cccagagccc ctgggatcga gtgaaggacc tggccactgt gtacgtggat gtgctcaaag     180
acagcggcag agactatgtg tcccagtttg aaggctccgc cttgggaaaa cagctaaacc     240
taaagctcct tgacaactgg gacagcgtga cctccaccct cagcaagctg cgcgaacagc     300
tcggccctgt gacccaggag ttctgggata acctggaaaa ggagacagag ggcctgaggc     360
aggagatgag caaggatctg gaggaggtga aggccaaggt gcagccctac ctggacgact     420
tccagaagaa gtggcaggag gagatggagc tctaccgcca aaggtggag ccgctgcgcg      480 cagagctcca agagggcgcg cgccagaagc tgcacgagct gcaagagaag ctgagcccac     540
tgggcgagga gatgcgcgac cgcgcgcgcg cccatgtgga cgcgctgcgc acgcatctgg     600 cccctacag cgacgagctg cgccagcgct tggccgcgcg ccttgaggct ctcaaggaga     660
acggcggcgc cagactggcc gagtaccacg ccaaggccac cgagcatctg agcacgctca     720
gcgagaaggc caagcccgcg ctcgaggacc tccgccaagg cctgctgccc gtgctggaga     780
gcttcaaggt cagcttcctg agcgctctcg aggagtacac taagaagctc aacacccagt     840
gaggcgcccg ccgccgcccc ccttcccggt gctcagaata aacgtttcca aagtggg        897

<210> SEQ ID NO 44
<211> LENGTH: 52
<212> TYPE: DNA
<213> ORGANISM: Artificial
<220> FEATURE:
<223> OTHER INFORMATION: Chemically Synthesized

<400> SEQUENCE: 44
gggtgtgttt cgccgagaag caccccccca gagcccctgg gatcgagtga ag             52

<210> SEQ ID NO 45
<211> LENGTH: 54
<212> TYPE: DNA
<213> ORGANISM: Artificial
<220> FEATURE:
<223> OTHER INFORMATION: Chemically Synthesized

<400> SEQUENCE: 45
aggggtgtgt ttcgccgaga agcacccccc cagagcccct gggatcgagt gaag            54

<210> SEQ ID NO 46
<211> LENGTH: 79
<212> TYPE: DNA
<213> ORGANISM: Artificial
<220> FEATURE:
<223> OTHER INFORMATION: Chemically Synthesized

<400> SEQUENCE: 46
atgaagtggg taacctttat ttcccttctt tttctcttta gctcggctta ttccaggggt      60
gtgtttcgtc gagatgcac                                                  79
```